US011926671B2

(12) United States Patent
Poirier et al.

(10) Patent No.: US 11,926,671 B2
(45) Date of Patent: Mar. 12, 2024

(54) ANTIBODIES AND POLYPEPTIDES DIRECTED AGAINST CD127

(71) Applicant: OSE IMMUNOTHERAPEUTICS, Nantes (FR)

(72) Inventors: Nicolas Poirier, Treillieres (FR); Caroline Mary, Sainte-Pazanne (FR); Bernard Vanhove, Reze (FR); Virginie Thepenier, Sainte-Pazanne (FR)

(73) Assignee: OSE IMMUNOTHERAPEUTICS, Nantes (FR)

( * ) Notice: Subject to any disclaimer, the term of this patent is extended or adjusted under 35 U.S.C. 154(b) by 100 days.

(21) Appl. No.: 17/363,260

(22) Filed: Jun. 30, 2021

(65) Prior Publication Data

US 2021/0395376 A1 Dec. 23, 2021
US 2022/0332834 A2 Oct. 20, 2022

Related U.S. Application Data

(62) Division of application No. 16/467,284, filed as application No. PCT/EP2017/081911 on Dec. 7, 2017, now Pat. No. 11,098,128.

(30) Foreign Application Priority Data

Dec. 9, 2016 (EP) .................... 16306655

(51) Int. Cl.
*C07K 16/24* (2006.01)
*C07K 16/28* (2006.01)

(52) U.S. Cl.
CPC ........ *C07K 16/2866* (2013.01); *C07K 16/244* (2013.01); *C07K 2317/14* (2013.01); *C07K 2317/24* (2013.01); *C07K 2317/76* (2013.01); *C07K 2317/92* (2013.01)

(58) Field of Classification Search
CPC .................................................. A61K 39/395
See application file for complete search history.

(56) References Cited

U.S. PATENT DOCUMENTS 10,428,152 B2  10/2019  Poirier et al.

FOREIGN PATENT DOCUMENTS

| WO | 2010/017468 A1 | 2/2010 |
| WO | 2011/094259 A2 | 8/2011 |
| WO | 2011/104687 A1 | 9/2011 |
| WO | 2013056984 A1 | 4/2013 |
| WO | 2015/189302 A1 | 12/2015 |

OTHER PUBLICATIONS

Abraham et al., "Inflammatory Bowel Disease", The New England Journal of Medicine, 2009, pp. 2066-2078, vol. 361, No. 21.
Adams et al., "Aberrant Homing of Mucosal T Cells and Extra-Intestinal Manifestations of Inflammatory Bowel Disease", Nature Reviews Immunology, 2006, pp. 244-251, vol. 6.
Agace, "Tissue-Tropic Effector T Cells: Generation and Targeting Opportunities", Nature Reviews Immunology, 2006, pp. 682-692, vol. 6.
Albuquerque et al., "Rate of Increase in Circulating IL-7 and Loss of IL-7R a Expression Differ in HIV-1 and HIV-2 Infections: Two Lymphopenic Diseases with Similar Hyperimmune Activation but Distinct Outcomes", The Journal of Immunology, 2007, pp. 3252-3259, vol. 178.
Baumgart et al., "Crohn's Disease", Lancet, 2012, pp. 1590-1605, vol. 380.
Broux et al., "Haplotype 4 of the Multiple Sclerosis-Associated Interleukin-7 Receptor Alpha Gene Influences the Frequency of Recent Thymic Emigrants", Genes and Immunity, 2010, pp. 326-333, vol. 11.
Chothia et al., "Canonical Structures for the Hypervariable Regions of Immunoglobulins", J. Mol. Biol., 1987, pp. 901-917, vol. 196.
Chothia et al., "Structural Repertoire of the Human VH Segments", J. Mol. Biol., 1992, pp. 799-817, vol. 227.
Clark et al., "Influence of Canonical Structure Determining Residues on Antibody Affinity and Stability", Journal of Structural Biology, 2014, pp. 2223-2227, vol. 185.
Danese et al., "Ulcerative Colitis", The New England Journal of Medicine, 2011, pp. 1713-1725, vol. 365.
Denucci et al., "Integrin Function in T Cell Homing to Lymphoid and Non-Lymphoid Sites: Getting There and Staying There", Crit. Rev. Immunol., 2009, pp. 87-109, vol. 29, No. 2.
Deshpande et al., "IL-7- and IL-15-Mediated TCR Sensitization Enables T Cell Responses to Self-Antigens", J. Immunol., 2013, pp. 1416-1423, vol. 190, No. 4.
Dunham et al., "Blockade of CD127 Exerts a Dichotomous Clinical Effect in Marmoset Experimental Autoimmune Encephalomyelitis", J. Neuroimmune Pharmacol., 2016, pp. 73-83, vol. 11, No. 1.
Feagan et al., "Vedolizumab as Induction and Maintenance Therapy for Ulcerative Colitis", The New England Journal of Medicine, 2013, pp. 699-710, vol. 369, No. 8.
Fleming et al., "Pre-B Cell Receptor Signaling Mediates Selective Response to IL-7 at the Pro-B to Pre-B Cell Transition via an ERK/MAP Kinase-Dependent Pathway", Immunity, 2001, pp. 521-531, vol. 15.
Gorfu et al., "Role of b7 Integrins in Intestinal Lympocyte Homing and Retention", Curr. Mol. Med., 2009, pp. 836-850, vol. 9, No. 7.
Haas et al., "The Interleukin-7 Receptor a Chain Contributes to Altered Homeostatis of Regulatory T Cells in Multiple Sclerosis", Eur. J. Immunology, 2011, pp. 845-853, vol. 41.
Haudebourg et al., "Depleting T-Cell Subpopulations in Organ Transplantation", European Society for Organ Transplantation, 2009, pp. 509-518, vol. 22.
He et al., "Thymic Stromal Lymphopoietin", Ann N Y Acad. Sci., 2010, pp. 13-24, vol. 1183.
Henriques et al., "IL-7 Induces Rapid Clathrin-Mediated Internalization and JAK3-Dependent Degradation of IL-7Ra in T Cells", Blood, 2010, pp. 3269-3277, vol. 115, No. 16.
International Preliminary Report on Patentability dated Nov. 20, 2018 and Chapter II Demand dated Oct. 8, 2018 for PCT/EP2017/081911.

(Continued)

*Primary Examiner* — Prema M Mertz
(74) *Attorney, Agent, or Firm* — Thompson Coburn LLP; William A. Holtz

(57) ABSTRACT

The invention is in the field of antibodies useful in therapeutic and diagnostics applications targeting CD127, the alpha chain of the IL7 receptor, and provides in particular humanized monoclonal antibodies against CD127, particularly human CD127, therapeutic uses thereof, and diagnostics applications.

17 Claims, 13 Drawing Sheets

Specification includes a Sequence Listing.

(56) References Cited

OTHER PUBLICATIONS

International Search Report and Written Opinion for PCT/EP2017/081911 dated May 3, 2018.
Kern et al., "Receptor Occupancy and Blocking of STAT5 Signaling by an Anti-IL-7 Receptor a Antibody in Cynomolgus Monkeys", Cytometry Part B, 2016, pp. 191-198, vol. 90B.
Kern et al., "Receptor Occupancy and Internalization of an Anti-IL-7 Receptor Antibody", Cytokine Abstract, 2013, pp. 276-277, vol. 63.
Khor et al., "Genetics and Pathogenesis of Inflmmatory Bowel Disease", Nature, 2011, pp. 307-317, vol. 474, No. 7351.
Lei et al., "TSLP Interferes with Airway Tolerance by Suppressing the Generation of Antigen-Specific Regulatory T Cells", J. Immunol., 2011, pp. 2254-2261, vol. 186, No. 4.
Mazzucchelli et al., "Development of Regulatory T Cells Requires IL-7Ra Stimulation by IL-7 or TSLP", Blood, 2008, pp. 3283-3292, vol. 112, No. 8.
McElroy et al., "Structural and Biophysical Studies of the Human IL-7/IL-7Ra Complex", Structure, 2009, pp. 54-65, vol. 17.
McElroy et al., "Structural Reorganization of the Interleukin-7 Signaling Complex", PNAS, 2012, pp. 2503-2508, vol. 109, No. 7.
Michel et al., "Patients with Relapsing-Remitting Multiple Sclerosis have Normal Treg Function when Cells Expressing IL-7 Receptor a-Chain are Excluded from the Analysis", The Journal of Clinical Investigation, 2008, pp. 3411-3419, vol. 118, No. 10.
Planell et al., "Transcriptional Analysis of the Intestinal Mucosa of Patients with ulcerative Colitis in Remission Reveals Lasting Epithelial Cell Alterations", Gut, 2013, pp. 967-976, vol. 62.
Racape et al., "Interleukin 7 Receptor a as a Potential Therapeutic Target in Transplantation", Arch. Immunol. Ther. Exp., 2009, pp. 253-261, vol. 57.
Reche et al., "Human Thymic Stromal Lymphopoietin Preferentially Stimulates Myeloid Cells", J. Immunol., 2001, pp. 336-343, vol. 167.
Roan et al., "The Multiple Facets of Thymic Stromal Lymphopoietin (TSLP) During Allergic Inflammation and Beyond", J. Leukoc. Biol., 2012, pp. 877-886, vol. 91, No. 6.
Rochman et al., "Thymic Stromal Lymphopoietin-Mediated STAT5 Phosphorylation via Kinases JAK1 and JAK2 Reveals a Key Difference from IL-7-Induced Signaling", PNAS, 2010, pp. 19455-19460, vol. 107, No. 45.
Sandborn et al., "Vedolizumab as Induction and Maintenance Therapy for Crohn's Disease", The New Englend Journal of Medicine, 2013, pp. 711-721, vol. 369, No. 8.
Shochat et al., "Gain-of-Function Mutations in Interleukin-7 Receptor-a (IL7R) in Childhood Acute Lymphoblastic Leukemias", J. Exp. Med., 2011, pp. 901-908, vol. 208, No. 5.
Taylor et al., TSLP Regulates Intestinal immunity and Inflammation in Mouse Models of Helminth Infection and Colitis, JEM, 2008, pp. 655-667, vol. 206, No. 3.
Van Bodegom et al., "Differences in Signaling Through the B-Cell Leukemia Oncoprotein CRLF2 in Response to TSLP and Through Mutant JAK2", Blood, 2012, pp. 2853-2863, vol. 120, No. 14.
Verstraete et al., "Structure and Antagonism of the Receptor Complex Mediated by Human TSLP in Allergy and Asthma", Nature Communications, 2017, 17 pages.
Walsh, "Structureal Insights into the Common Y-Chain Family of Cytokines and Receptors from the interleukin-7 Pathway", Immunol. Rev., 2012, pp. 303-316, vol. 250, No. 1.
Watanabe et al., "Hassall's Corpuscles Instruct Dendritic Cells to Induce CD4+CD25+ Regulatory T Cells in Human Thymus", Nature, 2005, pp. 1181-1185, vol. 436.
Watanabe et al., "Interleukin 7 Transgenic Mice Develop Chronic Colitis with Decreased Interleukin 7 Protein Accumulation in the Colonic Mucosa", JEM, 1998, pp. 389-408, vol. 187, No. 3.
Wong et al., "Reproducibility and Correlations of Multiplex Cytokine Levels in Asymptomatic Persons", Cancer Epidemiol., Biomarkers and Prevention, 2008, pp. 3450-3456, vol. 17, No. 12.
Ying et al., "Expression and Cellular Provenance of Thymic Stromal Lymphopoietin and Chemokines in Patients with Severe Asthma and Chronic Obstructive Pulmonar Disease", J. Immunol., 2008, pp. 2790-2798, vol. 181.
Zhi et al., "a4b7 Integrin (LPAM-1) is Upregulated at Atherosclerotic Lesions and is Involved in Atherosclerosis Progression", Cell. Physiol. Biochem., 2014, pp. 1887-1887, vol. 33.
Zhong et al., "TSLP Signaling Pathway Map: A Platform for Analysis of TSLP-Mediated Signaling", Database, 2014, 8 pages.

A

N13B2-VH (SEQ ID No: 7)

QVQLVESGGGLVKPGGSLRLSCAVSGFTLSDYYMAWIRQAPGKGL
EWVSTISASGLRTYYPDSVKGRFTISRDNAKNSLYLQMNSLRAEDTA
VYYCARPLSAHYGFNYFDYWGQGTLVTVSS

B

N13B2-hVL3 (SEQ ID No: 9)

DIQMTQSPSSLSASVGDRVTITCRTSEDIYQGLAWYQQKPGKAPKL
LVYSANTLHIGVPSRFSGSGSGTDYTLTISSLQPEDFATYF**CQQYYDY
PLA**FGGGTKVEIK

N13B2-hVL4-V48L (SEQ ID No: 10)

DIQMTQSPSSLSASVGDRVTITCRTSEDIYQGLAWYQQKPGKAPKL
LLYSANTLHIGVPSRFSGSGSGTDYTLTISSLQPEDFATYF**CQQYYDYP
LA**FGGGTKVEIK

N13B2-hVL5-F87Y (SEQ ID No: 11)

DIQMTQSPSSLSASVGDRVTITCRTSEDIYQGLAWYQQKPGKAPKL
LVYSANTLHIGVPSRFSGSGSGTDYTLTISSLQPEDFATYY**CQQYYDY
PLA**FGGGTKVEIK

N13B2-hVL6-V48L-F87Y (SEQ ID No: 12)

DIQMTQSPSSLSASVGDRVTITCRTSEDIYQGLAWYQQKPGKAPKL
LLYSANTLHIGVPSRFSGSGSGTDYTLTISSLQPEDFATYY**CQQYYDYP
LA**FGGGTKVEIK

Fig. 1A,B

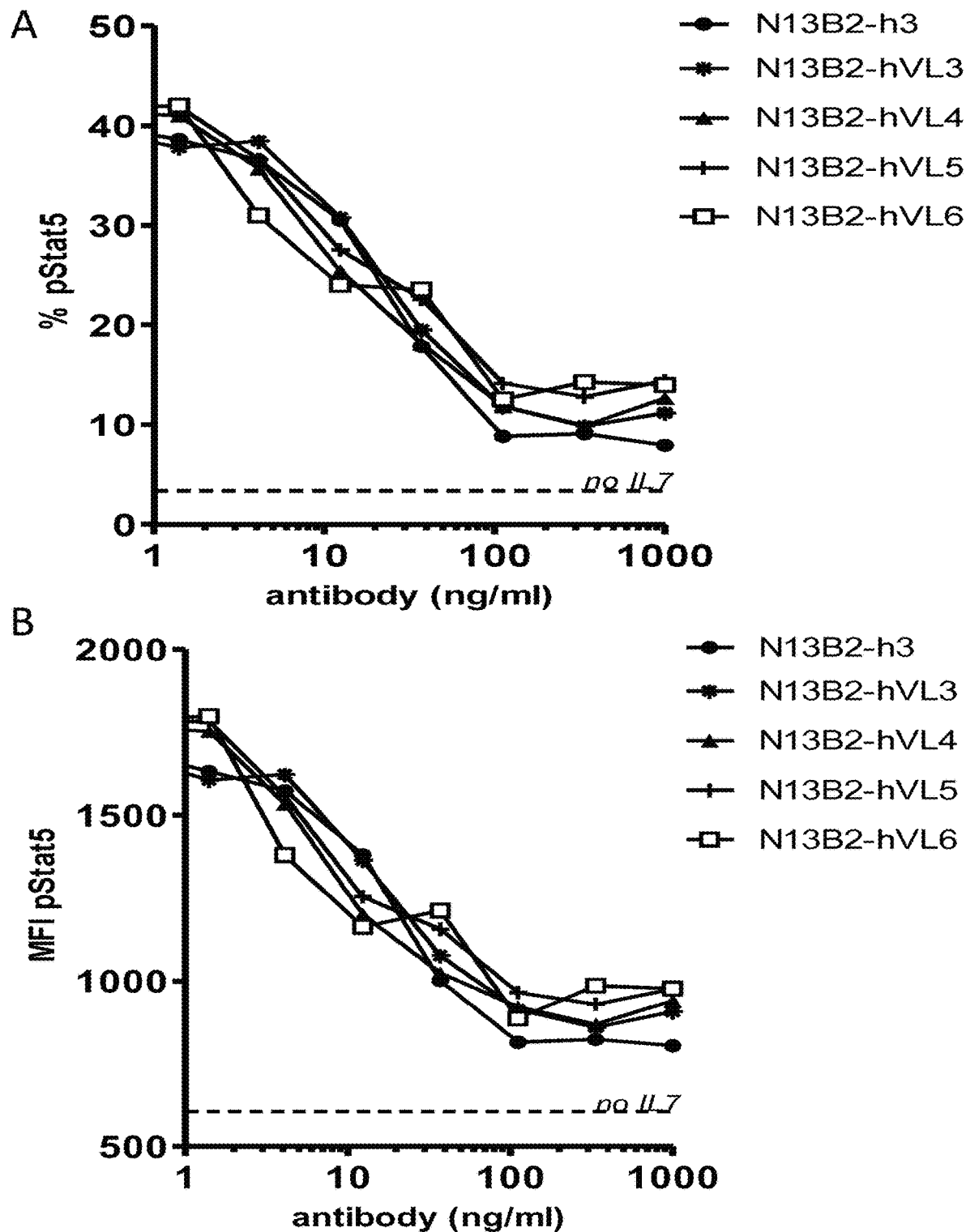
Fig. 4A,B

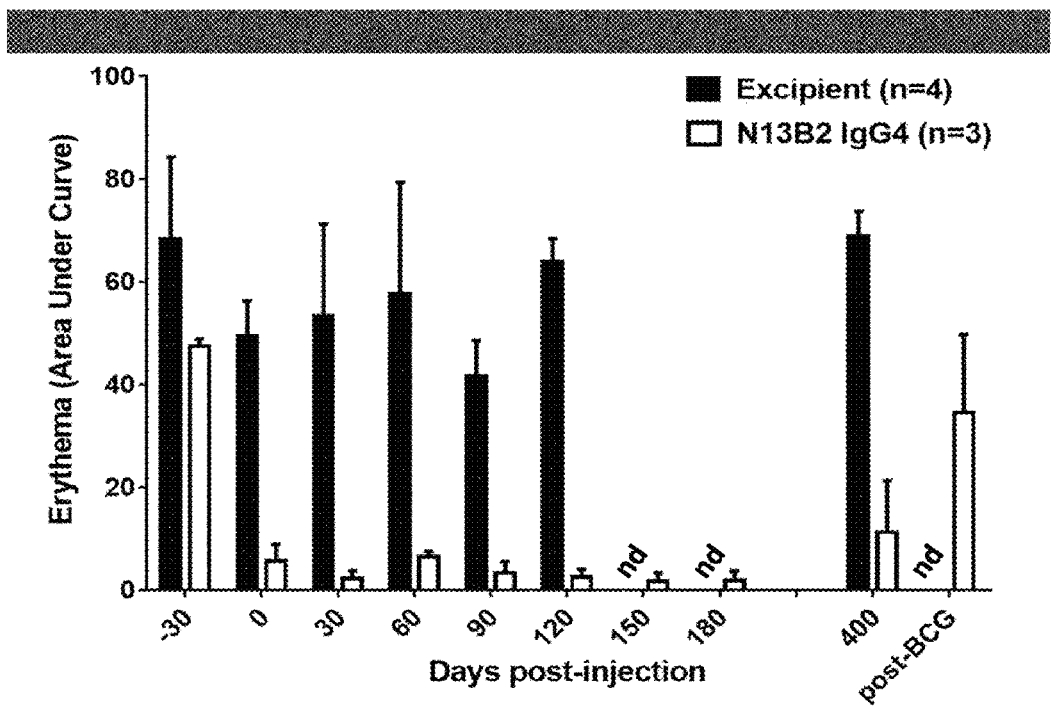
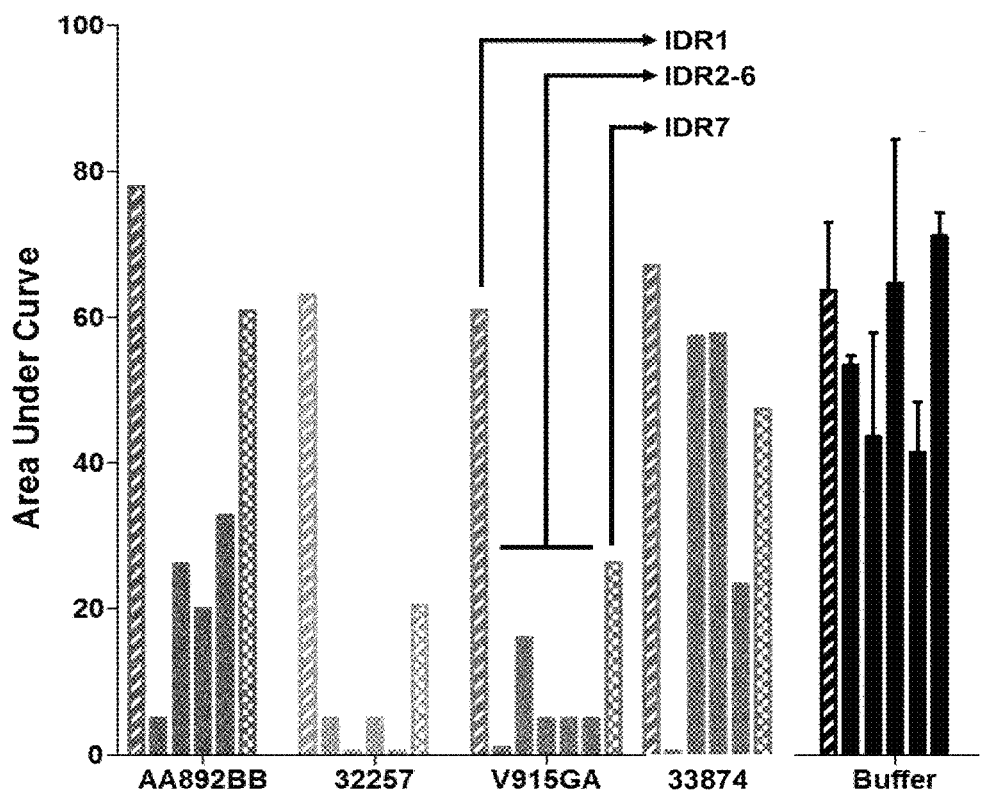
Fig. 5A,B

C
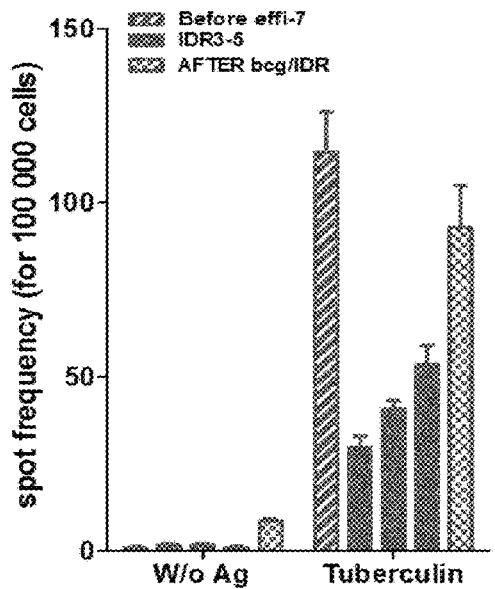
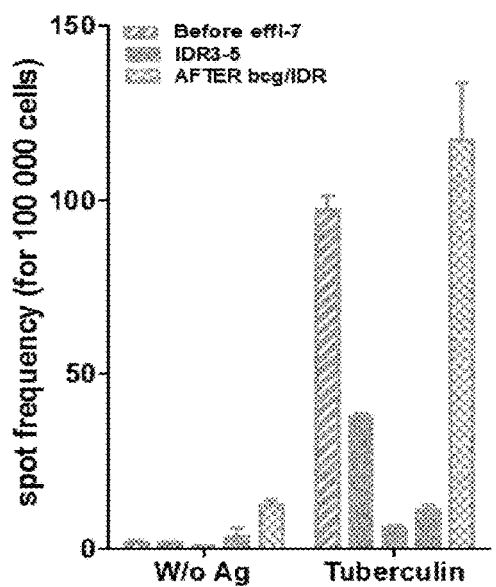
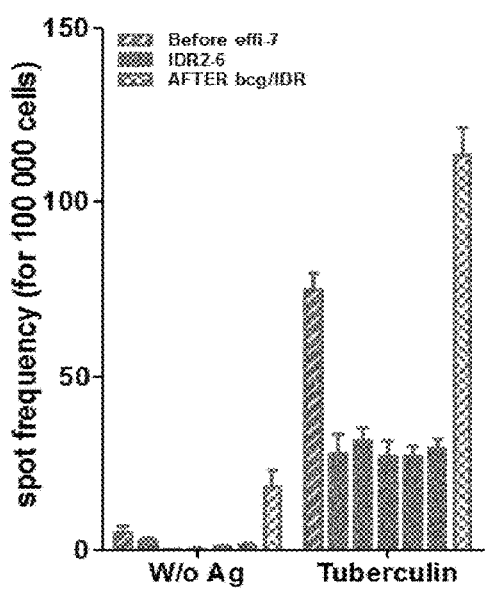
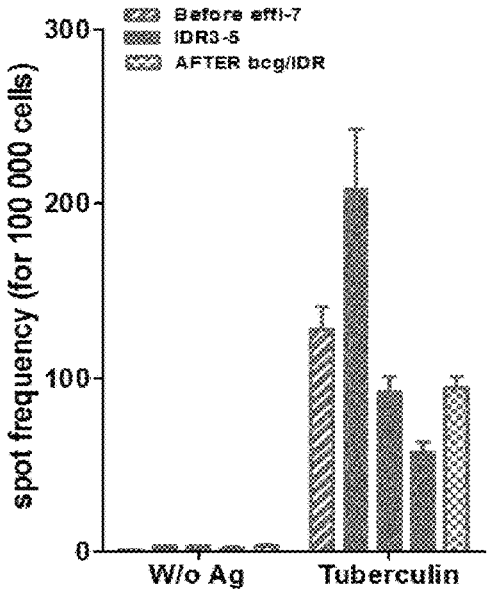
Fig. 5 (Continued)

A
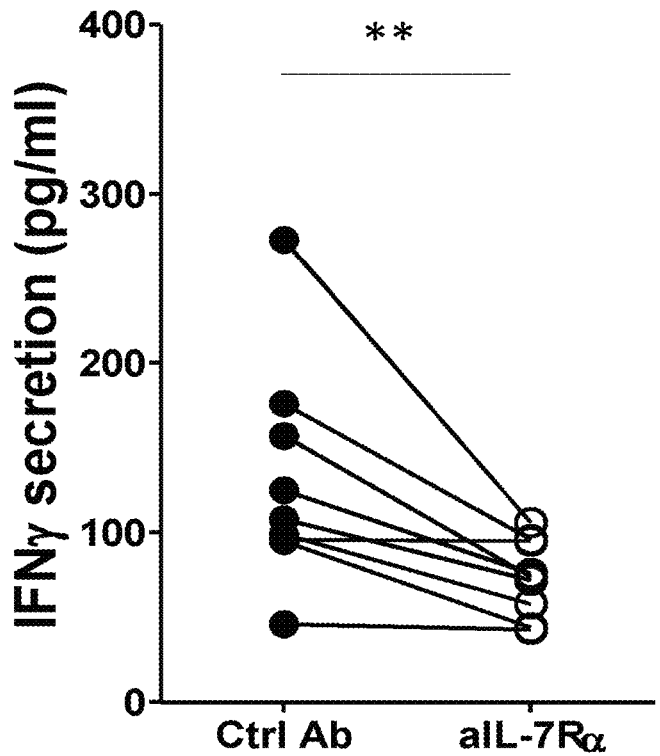
B
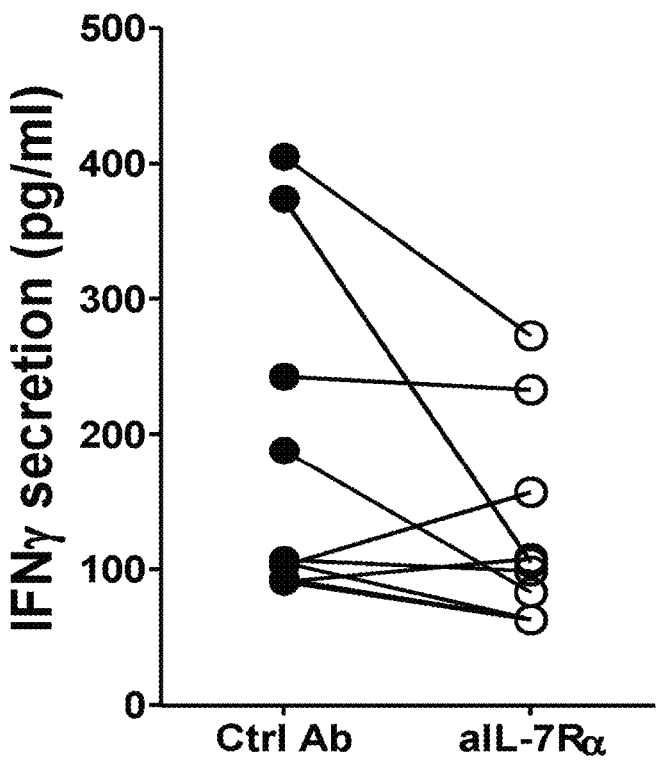
Fig. 8A,B

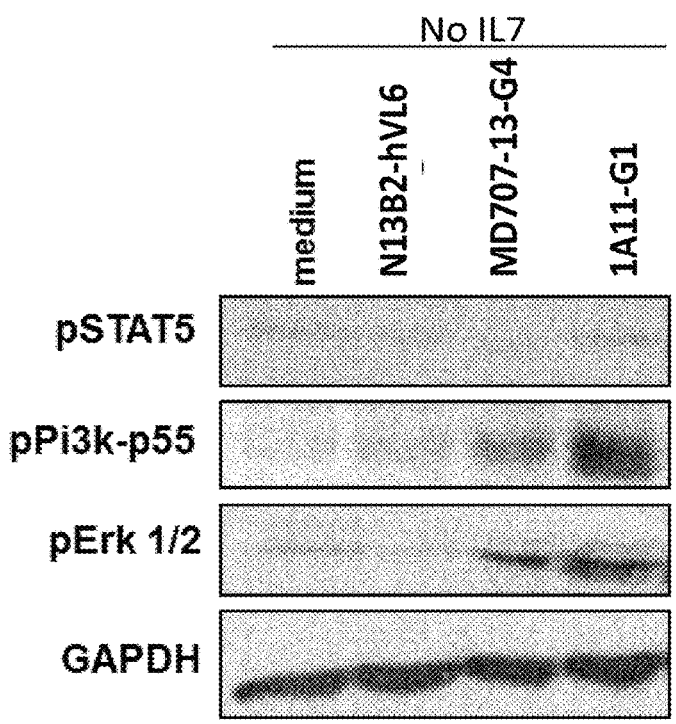
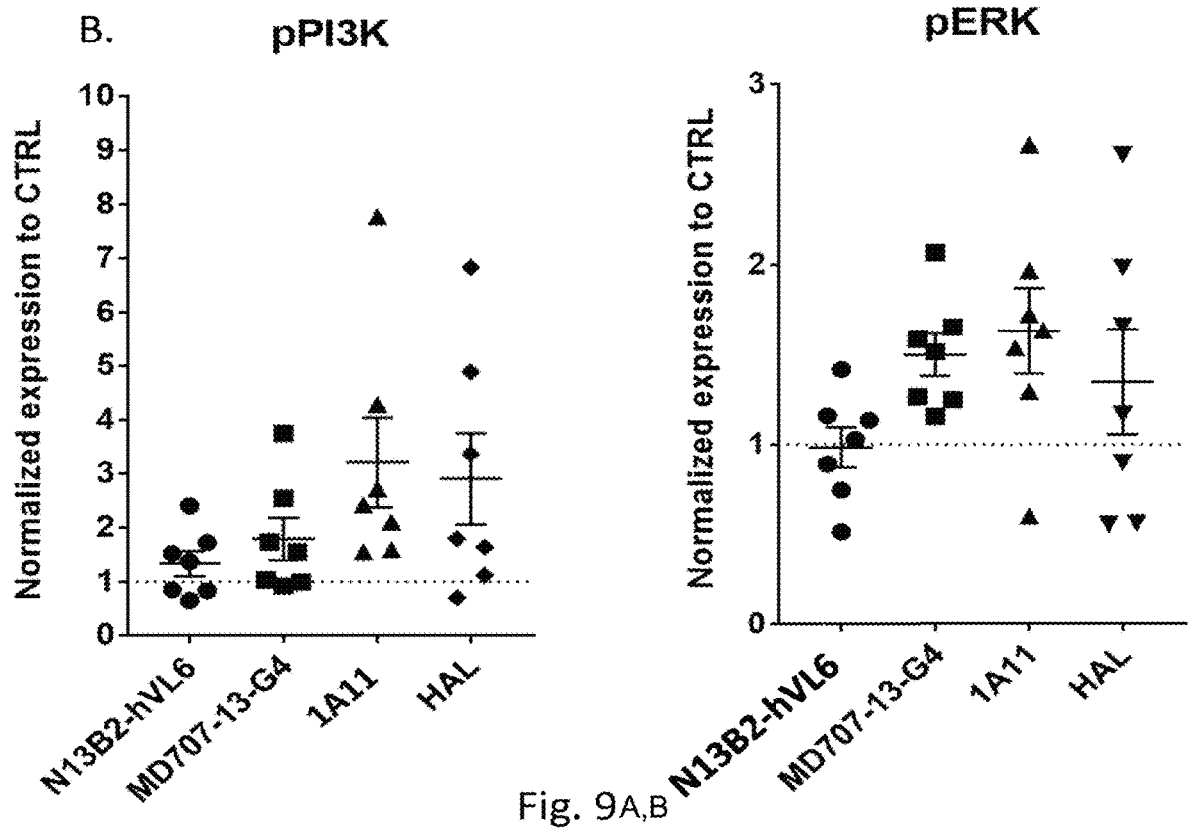
Fig. 9A,B

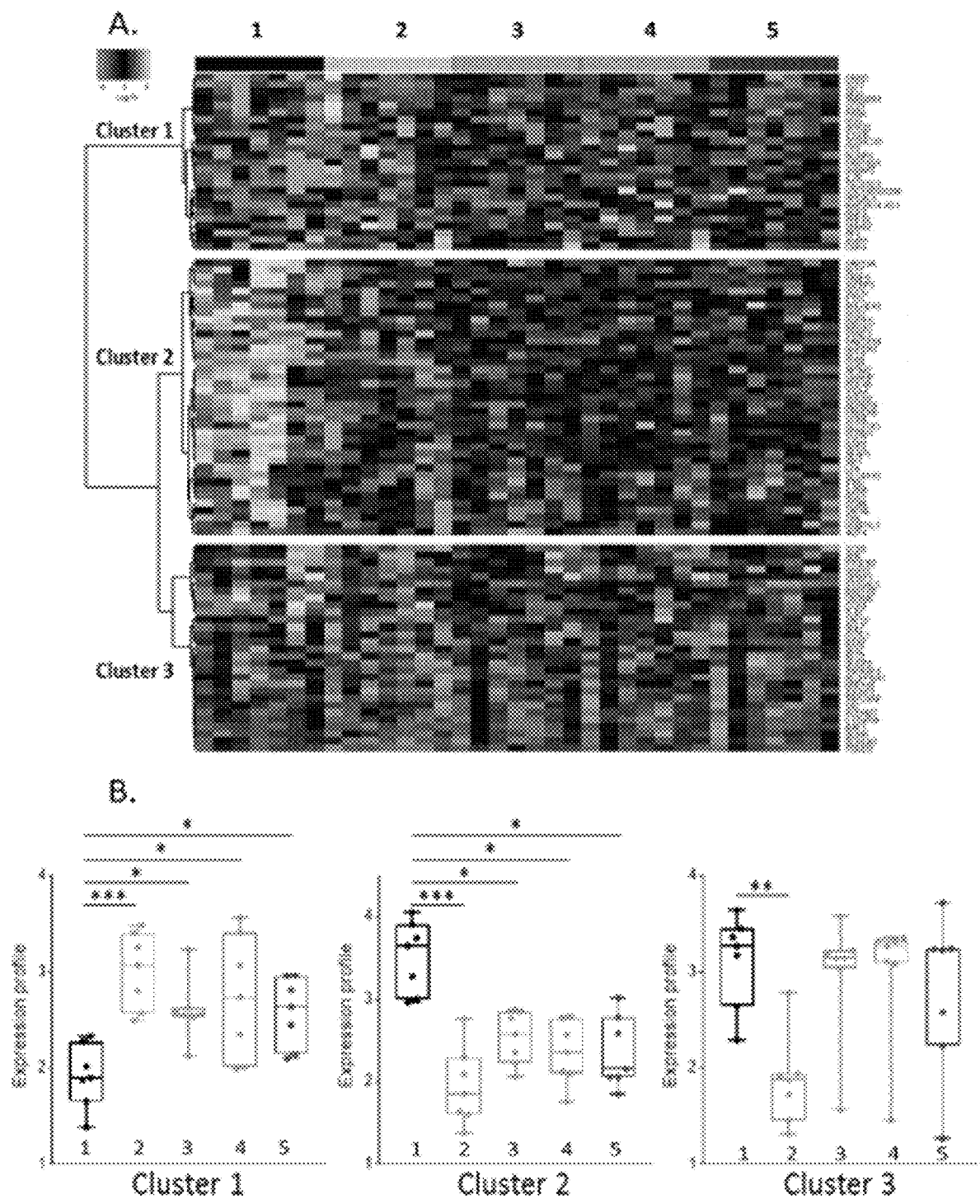
Fig. 11A,B

SEQUENCE LISTING

```
<160> NUMBER OF SEQ ID NOS: 96

<210> SEQ ID NO 1
<211> LENGTH: 9
<212> TYPE: PRT
<213> ORGANISM: Artificial Sequence
<220> FEATURE:
<223> OTHER INFORMATION: Synthetic sequence

<400> SEQUENCE: 1

Phe Thr Leu Ser Asp Tyr Tyr Met Ala
1               5

<210> SEQ ID NO 2
<211> LENGTH: 17
<212> TYPE: PRT
<213> ORGANISM: Artificial Sequence
<220> FEATURE:
<223> OTHER INFORMATION: Synthetic sequence

<400> SEQUENCE: 2

Thr Ile Ser Ala Ser Gly Leu Arg Thr Tyr Tyr Pro Asp Ser Val Lys
1               5                   10                  15

Gly

<210> SEQ ID NO 3
<211> LENGTH: 13
<212> TYPE: PRT
<213> ORGANISM: Artificial Sequence
<220> FEATURE:
<223> OTHER INFORMATION: Synthetic sequence

<400> SEQUENCE: 3

Pro Leu Ser Ala His Tyr Gly Phe Asn Tyr Phe Asp Tyr
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Synthetic sequence
```

```
<400> SEQUENCE: 4

Arg Thr Ser Glu Asp Ile Tyr Gln Gly Leu Ala
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Synthetic sequence

<400> SEQUENCE: 5

Ser Ala Asn Thr Leu His Ile
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic sequence

<400> SEQUENCE: 6

Gln Gln Tyr Tyr Asp Tyr Pro Leu Ala
1               5

<210> SEQ ID NO 7
<211> LENGTH: 122
<212> TYPE: PRT
<213> ORGANISM: Artificial Sequence
<220> FEATURE:
<223> OTHER INFORMATION: Synthetic sequence

<400> SEQUENCE: 7

Gln Val Gln Leu Val Glu Ser Gly Gly Gly Leu Val Lys Pro Gly Gly
1               5                   10                  15

Ser Leu Arg Leu Ser Cys Ala Val Ser Gly Phe Thr Leu Ser Asp Tyr
            20                  25                  30

Tyr Met Ala Trp Ile Arg Gln Ala Pro Gly Lys Gly Leu Glu Trp Val
        35                  40                  45

Ser Thr Ile Ser Ala Ser Gly Leu Arg Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Pro Leu Ser Ala His Tyr Gly Phe Asn Tyr Phe Asp Tyr Trp
            100                 105                 110

Gly Gln Gly Thr Leu Val Thr Val Ser Ser
        115                 120

<210> SEQ ID NO 8
<211> LENGTH: 107
<212> TYPE: PRT
<213> ORGANISM: Artificial Sequence
<220> FEATURE:
<223> OTHER INFORMATION: Synthetic sequence

<400> SEQUENCE: 8

Glu Ile Val Met Thr Gln Ser Pro Ala Thr Leu Ser Val Ser Pro Gly
1               5                   10                  15

Glu Arg Ala Thr Leu Ser Cys Arg Thr Ser Glu Asp Ile Tyr Gln Gly
```

```
                        20                  25                  30
Leu Ala Trp Tyr Gln Gln Lys Pro Gly Gln Ala Pro Arg Leu Leu Ile
            35                  40                  45

Tyr Ser Ala Asn Thr Leu His Ile Gly Ile Pro Ala Arg Phe Ser Gly
        50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Tyr Asp Tyr Pro Leu
                85                  90                  95

Ala Phe Gly Gly Gly Thr Lys Val Glu Ile Lys
            100                 105
```

<210> SEQ ID NO 9
<211> LENGTH: 107
<212> TYPE: PRT
<213> ORGANISM: Artificial Sequence
<220> FEATURE:
<223> OTHER INFORMATION: Synthetic sequence

<400> SEQUENCE: 9

```
Asp Ile Gln Met Thr Gln Ser Pro Ser Ser Leu Ser Ala Ser Val Gly
1               5                   10                  15

Asp Arg Val Thr Ile Thr Cys Arg Thr Ser Glu Asp Ile Tyr Gln Gly
            20                  25                  30

Leu Ala Trp Tyr Gln Gln Lys Pro Gly Lys Ala Pro Lys Leu Leu Val
            35                  40                  45

Tyr Ser Ala Asn Thr Leu His Ile Gly Val Pro Ser Arg Phe Ser Gly
        50                  55                  60

Ser Gly Ser Gly Thr Asp Tyr Thr Leu Thr Ile Ser Ser Leu Gln Pro
65                  70                  75                  80

Glu Asp Phe Ala Thr Tyr Phe Cys Gln Gln Tyr Tyr Asp Tyr Pro Leu
                85                  90                  95

Ala Phe Gly Gly Gly Thr Lys Val Glu Ile Lys
            100                 105
```

<210> SEQ ID NO 10
<211> LENGTH: 107
<212> TYPE: PRT
<213> ORGANISM: Artificial Sequence
<220> FEATURE:
<223> OTHER INFORMATION: Synthetic sequence

<400> SEQUENCE: 10

```
Asp Ile Gln Met Thr Gln Ser Pro Ser Ser Leu Ser Ala Ser Val Gly
1               5                   10                  15

Asp Arg Val Thr Ile Thr Cys Arg Thr Ser Glu Asp Ile Tyr Gln Gly
            20                  25                  30

Leu Ala Trp Tyr Gln Gln Lys Pro Gly Lys Ala Pro Lys Leu Leu Leu
            35                  40                  45

Tyr Ser Ala Asn Thr Leu His Ile Gly Val Pro Ser Arg Phe Ser Gly
        50                  55                  60

Ser Gly Ser Gly Thr Asp Tyr Thr Leu Thr Ile Ser Ser Leu Gln Pro
65                  70                  75                  80

Glu Asp Phe Ala Thr Tyr Phe Cys Gln Gln Tyr Tyr Asp Tyr Pro Leu
                85                  90                  95

Ala Phe Gly Gly Gly Thr Lys Val Glu Ile Lys
            100                 105
```

<210> SEQ ID NO 11
<211> LENGTH: 107
<212> TYPE: PRT
<213> ORGANISM: Artificial Sequence
<220> FEATURE:
<223> OTHER INFORMATION: Synthetic sequence

<400> SEQUENCE: 11

```
Asp Ile Gln Met Thr Gln Ser Pro Ser Ser Leu Ser Ala Ser Val Gly
1               5                   10                  15

Asp Arg Val Thr Ile Thr Cys Arg Thr Ser Glu Asp Ile Tyr Gln Gly
            20                  25                  30

Leu Ala Trp Tyr Gln Gln Lys Pro Gly Lys Ala Pro Lys Leu Leu Val
        35                  40                  45

Tyr Ser Ala Asn Thr Leu His Ile Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Tyr Tyr Asp Tyr Pro Leu
                85                  90                  95

Ala Phe Gly Gly Gly Thr Lys Val Glu Ile Lys
            100                 105
```

<210> SEQ ID NO 12
<211> LENGTH: 107
<212> TYPE: PRT
<213> ORGANISM: Artificial Sequence
<220> FEATURE:
<223> OTHER INFORMATION: Synthetic sequence

<400> SEQUENCE: 12

```
Asp Ile Gln Met Thr Gln Ser Pro Ser Ser Leu Ser Ala Ser Val Gly
1               5                   10                  15

Asp Arg Val Thr Ile Thr Cys Arg Thr Ser Glu Asp Ile Tyr Gln Gly
            20                  25                  30

Leu Ala Trp Tyr Gln Gln Lys Pro Gly Lys Ala Pro Lys Leu Leu Leu
        35                  40                  45

Tyr Ser Ala Asn Thr Leu His Ile Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Tyr Tyr Asp Tyr Pro Leu
                85                  90                  95

Ala Phe Gly Gly Gly Thr Lys Val Glu Ile Lys
            100                 105
```

<210> SEQ ID NO 13
<211> LENGTH: 366
<212> TYPE: DNA
<213> ORGANISM: Artificial Sequence
<220> FEATURE:
<223> OTHER INFORMATION: Synthetic sequence

<400> SEQUENCE: 13

```
caggtgcagc tggtcgaatc agggggggga ctggtcaaac ccggggggctc actgcgtctg     60 tcatgtgccg tctcaggctt cacactgagc gactactata tggcatggat ccgacaggca    120
ccaggcaagg gactggagtg ggtgtctact atttctgcca gtggcctgag gacctactat    180
cctgacagtg tcaagggaag gttcacaatc tcacgggata cgctaaaaa ttccctgtac    240
```
ctgcagatga acagcctgag agccgaagac accgctgtgt actattgcgc tcgcccactg    300
tccgcacact atggcttcaa ttactttgat tattgggggc agggtaccct ggtgacagtc    360
tccagc                                                                366

<210> SEQ ID NO 14
<211> LENGTH: 321
<212> TYPE: DNA
<213> ORGANISM: Artificial Sequence
<220> FEATURE:
<223> OTHER INFORMATION: Synthetic sequence

<400> SEQUENCE: 14
gagatcgtca tgacgcagtc ccccgcaacg ctctccgtct ccccggggga acgcgcgacc    60
ctgtcgtgca ggacctccga ggacatctac caaggcctcg cgtggtatca gcagaagccc    120
ggccaggccc cgcggctgtt gatctactcc gcgaacacct tgcacatcgg catcccggcg    180
cgcttctcgg ggtcagggag cggcaccgag ttcaccctga ccatctcgtc gctccagagc    240
gaggacttcg ccgtgtacta ctgccagcag tactacgact accccctggc gttcggggc    300 gggaccaagg tggagatcaa g                                               321

<210> SEQ ID NO 15
<211> LENGTH: 321
<212> TYPE: DNA
<213> ORGANISM: Artificial Sequence
<220> FEATURE:
<223> OTHER INFORMATION: Synthetic sequence

<400> SEQUENCE: 15
gacattcaga tgacccagtc cccctcgagc ctgagtgcga gtgtgggcga ccgcgtgacg    60
atcacctgcc ggacgtccga ggatatctac cagggcctcg cctggtacca gcagaagccg    120
ggcaaggccc ccaaactgct ggtctacagc gcgaacaccc tccacatcgg cgtccccagc    180
cggttcagcg gctccggctc gggaacggac tacaccctca cgatctcgtc cctgcagccg    240
gaagacttcg ccacctactt ctgccagcag tattacgact acccgctggc gttcggtggc    300
ggcaccaagg tcgagatcaa g                                               321

<210> SEQ ID NO 16
<211> LENGTH: 321
<212> TYPE: DNA
<213> ORGANISM: Artificial Sequence
<220> FEATURE:
<223> OTHER INFORMATION: Synthetic sequence

<400> SEQUENCE: 16
gacattcaga tgacccagtc cccctcgagc ctgagtgcga gtgtgggcga ccgcgtgacg    60
atcacctgcc ggacgtccga ggatatctac cagggcctcg cctggtacca gcagaagccg    120
ggcaaggccc ccaaactgct gctctacagc gcgaacaccc tccacatcgg cgtccccagc    180
cggttcagcg gctccggctc gggaacggac tacaccctca cgatctcgtc cctgcagccg    240
gaagacttcg ccacctactt ctgccagcag tattacgact acccgctggc gttcggtggc    300
ggcaccaagg tcgagatcaa g                                               321

<210> SEQ ID NO 17
<211> LENGTH: 321
<212> TYPE: DNA
<213> ORGANISM: Artificial Sequence
<220> FEATURE:

<223> OTHER INFORMATION: Synthetic sequence

<400> SEQUENCE: 17
gacattcaga tgacccagtc ccctcgagc ctgagtgcga gtgtgggcga ccgcgtgacg    60
atcacctgcc ggacgtccga ggatatctac cagggcctcg cctggtacca gcagaagccg   120
ggcaaggccc ccaaactgct ggtctacagc gcgaacaccc tccacatcgg cgtccccagc   180
cggttcagcg gctccggctc gggaacggac tacacccctc acgatctcgtc cctgcagccg   240 gaagacttcg ccacctacta ctgccagcag tattacgact accgctggc gttcggtggc   300 ggcaccaagg tcgagatcaa g                                              321

<210> SEQ ID NO 18
<211> LENGTH: 321
<212> TYPE: DNA
<213> ORGANISM: Artificial Sequence
<220> FEATURE:
<223> OTHER INFORMATION: Synthetic sequence

<400> SEQUENCE: 18
gacattcaga tgacccagtc ccctcgagc ctgagtgcga gtgtgggcga ccgcgtgacg    60
atcacctgcc ggacgtccga ggatatctac cagggcctcg cctggtacca gcagaagccg   120
ggcaaggccc ccaaactgct gctctacagc gcgaacaccc tccacatcgg cgtccccagc   180
cggttcagcg gctccggctc gggaacggac tacacccctc acgatctcgtc cctgcagccg   240 gaagacttcg ccacctacta ctgccagcag tattacgact accgctggc gttcggtggc   300 ggcaccaagg tcgagatcaa g                                              321

<210> SEQ ID NO 19
<211> LENGTH: 31
<212> TYPE: PRT
<213> ORGANISM: Artificial Sequence
<220> FEATURE:
<223> OTHER INFORMATION: Synthetic sequence

<400> SEQUENCE: 19

Lys Cys Leu Asn Phe Arg Lys Leu Gln Glu Ile Tyr Phe Ile Glu Thr
1               5                   10                  15

Lys Lys Phe Leu Leu Ile Gly Lys Ser Asn Ile Cys Val Lys Val
            20                  25                  30

<210> SEQ ID NO 20
<211> LENGTH: 31
<212> TYPE: PRT
<213> ORGANISM: Artificial Sequence
<220> FEATURE:
<223> OTHER INFORMATION: Synthetic sequence

<400> SEQUENCE: 20

Tyr Glu Ile Lys Val Arg Ser Ile Pro Asp His Tyr Phe Lys Gly Phe
1               5                   10                  15

Trp Ser Glu Trp Ser Pro Ser Tyr Tyr Phe Arg Thr Pro Glu Ile
            20                  25                  30

<210> SEQ ID NO 21
<211> LENGTH: 459
<212> TYPE: PRT
<213> ORGANISM: Homo sapiens

<400> SEQUENCE: 21

Met Thr Ile Leu Gly Thr Thr Phe Gly Met Val Phe Ser Leu Leu Gln

-continued

```
1               5                    10                   15
Val Val Ser Gly Glu Ser Gly Tyr Ala Gln Asn Gly Asp Leu Glu Asp
            20                  25                  30

Ala Glu Leu Asp Asp Tyr Ser Phe Ser Cys Tyr Ser Gln Leu Glu Val
            35                  40                  45

Asn Gly Ser Gln His Ser Leu Thr Cys Ala Phe Glu Asp Pro Asp Val
            50                  55                  60

Asn Thr Thr Asn Leu Glu Phe Glu Ile Cys Gly Ala Leu Val Glu Val
65                  70                  75                  80

Lys Cys Leu Asn Phe Arg Lys Leu Gln Glu Ile Tyr Phe Ile Glu Thr
                    85                  90                  95

Lys Lys Phe Leu Leu Ile Gly Lys Ser Asn Ile Cys Val Lys Val Gly
                100                 105                 110

Glu Lys Ser Leu Thr Cys Lys Lys Ile Asp Leu Thr Thr Ile Val Lys
                115                 120                 125

Pro Glu Ala Pro Phe Asp Leu Ser Val Ile Tyr Arg Glu Gly Ala Asn
            130                 135                 140

Asp Phe Val Val Thr Phe Asn Thr Ser His Leu Gln Lys Lys Tyr Val
145                 150                 155                 160

Lys Val Leu Met His Asp Val Ala Tyr Arg Gln Glu Lys Asp Glu Asn
                    165                 170                 175

Lys Trp Thr His Val Asn Leu Ser Ser Thr Lys Leu Thr Leu Leu Gln
                    180                 185                 190

Arg Lys Leu Gln Pro Ala Ala Met Tyr Glu Ile Lys Val Arg Ser Ile
                    195                 200                 205

Pro Asp His Tyr Phe Lys Gly Phe Trp Ser Glu Trp Ser Pro Ser Tyr
            210                 215                 220

Tyr Phe Arg Thr Pro Glu Ile Asn Asn Ser Ser Gly Glu Met Asp Pro
225                 230                 235                 240

Ile Leu Leu Thr Ile Ser Ile Leu Ser Phe Phe Ser Val Ala Leu Leu
                    245                 250                 255

Val Ile Leu Ala Cys Val Leu Trp Lys Lys Arg Ile Lys Pro Ile Val
                    260                 265                 270

Trp Pro Ser Leu Pro Asp His Lys Lys Thr Leu Glu His Leu Cys Lys
                    275                 280                 285

Lys Pro Arg Lys Asn Leu Asn Val Ser Phe Asn Pro Glu Ser Phe Leu
            290                 295                 300

Asp Cys Gln Ile His Arg Val Asp Asp Ile Gln Ala Arg Asp Glu Val
305                 310                 315                 320

Glu Gly Phe Leu Gln Asp Thr Phe Pro Gln Gln Leu Glu Glu Ser Glu
                    325                 330                 335

Lys Gln Arg Leu Gly Gly Asp Val Gln Ser Pro Asn Cys Pro Ser Glu
                    340                 345                 350

Asp Val Val Ile Thr Pro Glu Ser Phe Gly Arg Asp Ser Ser Leu Thr
            355                 360                 365

Cys Leu Ala Gly Asn Val Ser Ala Cys Asp Ala Pro Ile Leu Ser Ser
            370                 375                 380

Ser Arg Ser Leu Asp Cys Arg Glu Ser Gly Lys Asn Gly Pro His Val
385                 390                 395                 400

Tyr Gln Asp Leu Leu Leu Ser Leu Gly Thr Thr Asn Ser Thr Leu Pro
                    405                 410                 415

Pro Pro Phe Ser Leu Gln Ser Gly Ile Leu Thr Leu Asn Pro Val Ala
                    420                 425                 430
```

Gln Gly Gln Pro Ile Leu Thr Ser Leu Gly Ser Asn Gln Glu Glu Ala
            435                 440                 445

Tyr Val Thr Met Ser Ser Phe Tyr Gln Asn Gln
    450                 455

<210> SEQ ID NO 22
<211> LENGTH: 219
<212> TYPE: PRT
<213> ORGANISM: Artificial Sequence
<220> FEATURE:
<223> OTHER INFORMATION: Synthetic sequence

<400> SEQUENCE: 22

Glu Ser Gly Tyr Ala Gln Asn Gly Asp Leu Glu Asp Ala Glu Leu Asp
1               5                   10                  15

Asp Tyr Ser Phe Ser Cys Tyr Gln Leu Glu Val Asn Gly Ser Gln
                20                  25                  30

His Ser Leu Thr Cys Ala Phe Glu Asp Pro Asp Val Asn Thr Thr Asn
            35                  40                  45

Leu Glu Phe Glu Ile Cys Gly Ala Leu Val Glu Val Lys Cys Leu Asn
        50                  55                  60

Phe Arg Lys Leu Gln Glu Ile Tyr Phe Ile Glu Thr Lys Lys Phe Leu
65                  70                  75                  80

Leu Ile Gly Lys Ser Asn Ile Cys Val Lys Val Gly Glu Lys Ser Leu
                85                  90                  95

Thr Cys Lys Lys Ile Asp Leu Thr Thr Ile Val Lys Pro Glu Ala Pro
            100                 105                 110

Phe Asp Leu Ser Val Ile Tyr Arg Glu Gly Ala Asn Asp Phe Val Val
        115                 120                 125

Thr Phe Asn Thr Ser His Leu Gln Lys Lys Tyr Val Lys Val Leu Met
    130                 135                 140

His Asp Val Ala Tyr Arg Gln Glu Lys Asp Glu Asn Lys Trp Thr His
145                 150                 155                 160

Val Asn Leu Ser Ser Thr Lys Leu Thr Leu Leu Gln Arg Lys Leu Gln
                165                 170                 175

Pro Ala Ala Met Tyr Glu Ile Lys Val Arg Ser Ile Pro Asp His Tyr
            180                 185                 190

Phe Lys Gly Phe Trp Ser Glu Trp Ser Pro Ser Tyr Tyr Phe Arg Thr
        195                 200                 205

Pro Glu Ile Asn Asn Ser Ser Gly Glu Met Asp
    210                 215

<210> SEQ ID NO 23
<211> LENGTH: 7
<212> TYPE: PRT
<213> ORGANISM: Artificial Sequence
<220> FEATURE:
<223> OTHER INFORMATION: Synthetic sequence

<400> SEQUENCE: 23

Phe Ile Glu Thr Lys Lys Phe
1               5

<210> SEQ ID NO 24
<211> LENGTH: 6
<212> TYPE: PRT
<213> ORGANISM: Artificial Sequence
<220> FEATURE:
<223> OTHER INFORMATION: Synthetic sequence

<400> SEQUENCE: 24

Asp Leu Ser Val Ile Tyr
1               5

<210> SEQ ID NO 25
<211> LENGTH: 4
<212> TYPE: PRT
<213> ORGANISM: Artificial Sequence
<220> FEATURE:
<223> OTHER INFORMATION: Synthetic sequence

<400> SEQUENCE: 25

Phe Lys Gly Phe
1

<210> SEQ ID NO 26
<211> LENGTH: 327
<212> TYPE: PRT
<213> ORGANISM: Artificial Sequence
<220> FEATURE:
<223> OTHER INFORMATION: Synthetic sequence

<400> SEQUENCE: 26

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
        290                 295                 300

Cys Ser Val Met His Glu Ala Leu His Asn His Tyr Thr Gln Lys Ser
305                 310                 315                 320

Leu Ser Leu Ser Pro Gly Lys
                325

<210> SEQ ID NO 27
<211> LENGTH: 107
<212> TYPE: PRT
<213> ORGANISM: Artificial Sequence
<220> FEATURE:
<223> OTHER INFORMATION: Synthetic sequence

<400> SEQUENCE: 27

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 28
<211> LENGTH: 106
<212> TYPE: PRT
<213> ORGANISM: Artificial Sequence
<220> FEATURE:
<223> OTHER INFORMATION: Synthetic sequence

<400> SEQUENCE: 28

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 29
<211> LENGTH: 984
<212> TYPE: DNA

<213> ORGANISM: Artificial Sequence
<220> FEATURE:
<223> OTHER INFORMATION: Synthetic sequence

<400> SEQUENCE: 29

| | |
|---|---|
| gctagcacca agggcccatc ggtcttcccc ctggcgccct gctccaggag cacctccgag | 60 |
| agcacagccg ccctgggctg cctggtcaag gactacttcc ccgaaccggt gacggtgtcg | 120 |
| tggaactcag gcgccctgac cagcggcgtg cacaccttcc cggctgtcct acagtcctca | 180 |
| ggactctact ccctcagcag cgtggtgacc gtgccctcca gcagcttggg cacgaagacc | 240 |
| tacacctgca acgtagatca caagcccagc aacaccaagg tggacaagag agttgagtcc | 300 |
| aaatatggtc ccccatgccc accatgccca gcacctgagt tcctgggggg accatcagtc | 360 |
| ttcctgttcc ccccaaaacc caaggacact ctcatgatct cccggacccc tgaggtcacg | 420 |
| tgcgtggtgg tggacgtgag ccaggaagac cccgaggtcc agttcaactg gtacgtggat | 480 |
| ggcgtggagg tgcataatgc caagacaaag ccgcgggagg agcagttcaa cagcacgtac | 540 |
| cgtgtggtca gcgtcctcac cgtcctgcac caggactggc tgaacggcaa ggagtacaag | 600 |
| tgcaaggtct ccaacaaagg cctcccgtcc tccatcgaga aaaccatctc caaagccaaa | 660 |
| gggcagcccc gagagccaca ggtgtacacc ctgcccccat cccaggagga gatgaccaag | 720 |
| aaccaggtca gcctgacctg cctggtcaaa ggcttctacc ccagcgacat cgccgtggag | 780 |
| tgggagagca atgggcagcc ggagaacaac tacaagacca cgcctcccgt gctggactcc | 840 |
| gacggctcct tcttcctcta cagcaggcta accgtggaca gagcaggtg gcaggagggg | 900 |
| aatgtcttct catgctccgt gatgcatgag gctctgcaca accactacac acagaagagc | 960 |
| ctctccctgt ctccgggtaa atga | 984 |

<210> SEQ ID NO 30
<211> LENGTH: 325
<212> TYPE: DNA
<213> ORGANISM: Artificial Sequence
<220> FEATURE:
<223> OTHER INFORMATION: Synthetic sequence

<400> SEQUENCE: 30

| | |
|---|---|
| cgcacggtgg ccgcgccgtc ggtgttcata ttcccgccga gcgacgagca gttgaagtcc | 60 |
| ggcaccgcct ccgtcgtgtg cctgctcaac aacttctacc cccgcgaggc gaaggtgcag | 120 |
| tggaaggtgg acaacgccct ccagtcgggc aacagtcagg agagcgtcac ggagcaggac | 180 |
| tccaaggact cgacatactc cctgtcctcg acgctgacct tgagcaaagc cgattacgag | 240 |
| aagcacaagg tgtacgcgtg cgaggtgacc catcagggcc tgtcctcccc ggtgaccaag | 300 |
| tccttcaacc ggggcgaatg ctgat | 325 |

<210> SEQ ID NO 31
<211> LENGTH: 322
<212> TYPE: DNA
<213> ORGANISM: Artificial Sequence
<220> FEATURE:
<223> OTHER INFORMATION: Synthetic sequence

<400> SEQUENCE: 31

| | |
|---|---|
| acggtggccg cgccgtcggt gttcatattc cgccgagcg acgagcagtt gaagtccggc | 60 |
| accgcctccg tcgtgtgcct gctcaacaac ttctaccccc gcgaggcgaa ggtgcagtgg | 120 |
| aaggtggaca acgccctcca gtcgggcaac agtcaggaga gcgtcacgga gcaggactcc | 180 |
| aaggactcga catactccct gtcctcgacg ctgaccttga gcaaagccga ttacgagaag | 240 |

```
cacaaggtgt acgcgtgcga ggtgacccat cagggcctgt cctccccggt gaccaagtcc    300
ttcaaccggg gcgaatgctg at                                             322
```

<210> SEQ ID NO 32
<211> LENGTH: 9
<212> TYPE: PRT
<213> ORGANISM: Artificial Sequence
<220> FEATURE:
<223> OTHER INFORMATION: Synthetic sequence

<400> SEQUENCE: 32

```
Phe Asp Leu Ser Val Ile Tyr Arg Glu
1               5
```

<210> SEQ ID NO 33
<211> LENGTH: 10
<212> TYPE: PRT
<213> ORGANISM: Artificial Sequence
<220> FEATURE:
<223> OTHER INFORMATION: Synthetic sequence

<400> SEQUENCE: 33

```
Asn Asp Phe Val Val Thr Phe Asn Thr Ser
1               5                   10
```

<210> SEQ ID NO 34
<211> LENGTH: 8
<212> TYPE: PRT
<213> ORGANISM: Artificial Sequence
<220> FEATURE:
<223> OTHER INFORMATION: Synthetic sequence

<400> SEQUENCE: 34

```
Thr Lys Leu Thr Leu Leu Gln Arg
1               5
```

<210> SEQ ID NO 35
<211> LENGTH: 15
<212> TYPE: PRT
<213> ORGANISM: Artificial Sequence
<220> FEATURE:
<223> OTHER INFORMATION: Synthetic sequence

<400> SEQUENCE: 35

```
Thr Leu Leu Gln Arg Lys Leu Gln Pro Ala Ala Met Tyr Glu Ile
1               5                   10                  15
```

<210> SEQ ID NO 36
<211> LENGTH: 10
<212> TYPE: PRT
<213> ORGANISM: Artificial Sequence
<220> FEATURE:
<223> OTHER INFORMATION: Synthetic sequence

<400> SEQUENCE: 36

```
Leu Val Glu Val Lys Cys Leu Asn Phe Arg
1               5                   10
```

<210> SEQ ID NO 37
<211> LENGTH: 14
<212> TYPE: PRT
<213> ORGANISM: Artificial Sequence
<220> FEATURE:
<223> OTHER INFORMATION: Synthetic sequence

<400> SEQUENCE: 37

```
Ile Cys Gly Ala Leu Val Glu Val Lys Cys Leu Asn Phe Arg
1               5                   10
```

<210> SEQ ID NO 38
<211> LENGTH: 11
<212> TYPE: PRT
<213> ORGANISM: Artificial Sequence
<220> FEATURE:
<223> OTHER INFORMATION: Synthetic sequence

<400> SEQUENCE: 38

```
Leu Val Glu Val Lys Cys Leu Asn Phe Arg Lys
1               5                   10
```

<210> SEQ ID NO 39
<211> LENGTH: 7
<212> TYPE: PRT
<213> ORGANISM: Artificial Sequence
<220> FEATURE:
<223> OTHER INFORMATION: Synthetic sequence

<400> SEQUENCE: 39

```
Lys Lys Phe Leu Leu Ile Gly
1               5
```

<210> SEQ ID NO 40
<211> LENGTH: 11
<212> TYPE: PRT
<213> ORGANISM: Artificial Sequence
<220> FEATURE:
<223> OTHER INFORMATION: Synthetic sequence

<400> SEQUENCE: 40

```
Lys Lys Phe Leu Leu Ile Gly Lys Ser Asn Ile
1               5                   10
```

<210> SEQ ID NO 41
<211> LENGTH: 11
<212> TYPE: PRT
<213> ORGANISM: Artificial Sequence
<220> FEATURE:
<223> OTHER INFORMATION: Synthetic sequence

<400> SEQUENCE: 41

```
Phe Ile Glu Thr Lys Lys Phe Leu Leu Ile Gly
1               5                   10
```

<210> SEQ ID NO 42
<211> LENGTH: 5
<212> TYPE: PRT
<213> ORGANISM: Artificial Sequence
<220> FEATURE:
<223> OTHER INFORMATION: Synthetic sequence

<400> SEQUENCE: 42

```
Cys Leu Asn Phe Arg
1               5
```

<210> SEQ ID NO 43
<211> LENGTH: 7
<212> TYPE: PRT
<213> ORGANISM: Artificial Sequence
<220> FEATURE:
<223> OTHER INFORMATION: Synthetic sequence

<400> SEQUENCE: 43

```
Phe Ile Glu Thr Lys Lys Phe
1               5

<210> SEQ ID NO 44
<211> LENGTH: 15
<212> TYPE: PRT
<213> ORGANISM: Artificial Sequence
<220> FEATURE:
<223> OTHER INFORMATION: Synthetic sequence

<400> SEQUENCE: 44

Glu Ser Gly Tyr Ala Gln Asn Gly Asp Leu Glu Asp Ala Glu Leu
1               5                   10                  15

<210> SEQ ID NO 45
<211> LENGTH: 15
<212> TYPE: PRT
<213> ORGANISM: Artificial Sequence
<220> FEATURE:
<223> OTHER INFORMATION: Synthetic sequence

<400> SEQUENCE: 45

Ala Gln Asn Gly Asp Leu Glu Asp Ala Glu Leu Asp Asp Tyr Ser
1               5                   10                  15

<210> SEQ ID NO 46
<211> LENGTH: 15
<212> TYPE: PRT
<213> ORGANISM: Artificial Sequence
<220> FEATURE:
<223> OTHER INFORMATION: Synthetic sequence

<400> SEQUENCE: 46

Asp Leu Glu Asp Ala Glu Leu Asp Asp Tyr Ser Phe Ser Cys Tyr
1               5                   10                  15

<210> SEQ ID NO 47
<211> LENGTH: 15
<212> TYPE: PRT
<213> ORGANISM: Artificial Sequence
<220> FEATURE:
<223> OTHER INFORMATION: Synthetic sequence

<400> SEQUENCE: 47

Ala Glu Leu Asp Asp Tyr Ser Phe Ser Cys Tyr Ser Gln Leu Glu
1               5                   10                  15

<210> SEQ ID NO 48
<211> LENGTH: 15
<212> TYPE: PRT
<213> ORGANISM: Artificial Sequence
<220> FEATURE:
<223> OTHER INFORMATION: Synthetic sequence

<400> SEQUENCE: 48

Asp Tyr Ser Phe Ser Cys Tyr Ser Gln Leu Glu Val Asn Gly Ser
1               5                   10                  15

<210> SEQ ID NO 49
<211> LENGTH: 15
<212> TYPE: PRT
<213> ORGANISM: Artificial Sequence
<220> FEATURE:
<223> OTHER INFORMATION: Synthetic sequence

<400> SEQUENCE: 49

Ser Cys Tyr Ser Gln Leu Glu Val Asn Gly Ser Gln His Ser Leu
```

<210> SEQ ID NO 50
<211> LENGTH: 15
<212> TYPE: PRT
<213> ORGANISM: Artificial Sequence
<220> FEATURE:
<223> OTHER INFORMATION: Synthetic sequence

<400> SEQUENCE: 50

Gln Leu Glu Val Asn Gly Ser Gln His Ser Leu Thr Cys Ala Phe
1               5                   10                  15

<210> SEQ ID NO 51
<211> LENGTH: 15
<212> TYPE: PRT
<213> ORGANISM: Artificial Sequence
<220> FEATURE:
<223> OTHER INFORMATION: Synthetic sequence

<400> SEQUENCE: 51

Asn Gly Ser Gln His Ser Leu Thr Cys Ala Phe Glu Asp Pro Asp
1               5                   10                  15

<210> SEQ ID NO 52
<211> LENGTH: 15
<212> TYPE: PRT
<213> ORGANISM: Artificial Sequence
<220> FEATURE:
<223> OTHER INFORMATION: Synthetic sequence

<400> SEQUENCE: 52

His Ser Leu Thr Cys Ala Phe Glu Asp Pro Asp Val Asn Thr Thr
1               5                   10                  15

<210> SEQ ID NO 53
<211> LENGTH: 15
<212> TYPE: PRT
<213> ORGANISM: Artificial Sequence
<220> FEATURE:
<223> OTHER INFORMATION: Synthetic sequence

<400> SEQUENCE: 53

Cys Ala Phe Glu Asp Pro Asp Val Asn Thr Thr Asn Leu Glu Phe
1               5                   10                  15

<210> SEQ ID NO 54
<211> LENGTH: 15
<212> TYPE: PRT
<213> ORGANISM: Artificial Sequence
<220> FEATURE:
<223> OTHER INFORMATION: Synthetic sequence

<400> SEQUENCE: 54

Asp Pro Asp Val Asn Thr Thr Asn Leu Glu Phe Glu Ile Cys Gly
1               5                   10                  15

<210> SEQ ID NO 55
<211> LENGTH: 15
<212> TYPE: PRT
<213> ORGANISM: Artificial Sequence
<220> FEATURE:
<223> OTHER INFORMATION: Synthetic sequence

<400> SEQUENCE: 55

Asn Thr Thr Asn Leu Glu Phe Glu Ile Cys Gly Ala Leu Val Glu
1               5                   10                  15

<210> SEQ ID NO 56
<211> LENGTH: 15
<212> TYPE: PRT
<213> ORGANISM: Artificial Sequence
<220> FEATURE:
<223> OTHER INFORMATION: Synthetic sequence

<400> SEQUENCE: 56

Leu Glu Phe Glu Ile Cys Gly Ala Leu Val Glu Val Lys Cys Leu
1               5                   10                  15

<210> SEQ ID NO 57
<211> LENGTH: 15
<212> TYPE: PRT
<213> ORGANISM: Artificial Sequence
<220> FEATURE:
<223> OTHER INFORMATION: Synthetic sequence

<400> SEQUENCE: 57

Ile Cys Gly Ala Leu Val Glu Val Lys Cys Leu Asn Phe Arg Lys
1               5                   10                  15

<210> SEQ ID NO 58
<211> LENGTH: 15
<212> TYPE: PRT
<213> ORGANISM: Artificial Sequence
<220> FEATURE:
<223> OTHER INFORMATION: Synthetic sequence

<400> SEQUENCE: 58

Leu Val Glu Val Lys Cys Leu Asn Phe Arg Lys Leu Gln Glu Ile
1               5                   10                  15

<210> SEQ ID NO 59
<211> LENGTH: 15
<212> TYPE: PRT
<213> ORGANISM: Artificial Sequence
<220> FEATURE:
<223> OTHER INFORMATION: Synthetic sequence

<400> SEQUENCE: 59

Lys Cys Leu Asn Phe Arg Lys Leu Gln Glu Ile Tyr Phe Ile Glu
1               5                   10                  15

<210> SEQ ID NO 60
<211> LENGTH: 15
<212> TYPE: PRT
<213> ORGANISM: Artificial Sequence
<220> FEATURE:
<223> OTHER INFORMATION: Synthetic sequence

<400> SEQUENCE: 60

Phe Arg Lys Leu Gln Glu Ile Tyr Phe Ile Glu Thr Lys Lys Phe
1               5                   10                  15

<210> SEQ ID NO 61
<211> LENGTH: 15
<212> TYPE: PRT
<213> ORGANISM: Artificial Sequence
<220> FEATURE:
<223> OTHER INFORMATION: Synthetic sequence

<400> SEQUENCE: 61

Gln Glu Ile Tyr Phe Ile Glu Thr Lys Lys Phe Leu Leu Ile Gly
1               5                   10                  15

```
<210> SEQ ID NO 62
<211> LENGTH: 15
<212> TYPE: PRT
<213> ORGANISM: Artificial Sequence
<220> FEATURE:
<223> OTHER INFORMATION: Synthetic sequence

<400> SEQUENCE: 62

Phe Ile Glu Thr Lys Lys Phe Leu Leu Ile Gly Lys Ser Asn Ile
1               5                   10                  15

<210> SEQ ID NO 63
<211> LENGTH: 15
<212> TYPE: PRT
<213> ORGANISM: Artificial Sequence
<220> FEATURE:
<223> OTHER INFORMATION: Synthetic sequence

<400> SEQUENCE: 63

Lys Lys Phe Leu Leu Ile Gly Lys Ser Asn Ile Cys Val Lys Val
1               5                   10                  15

<210> SEQ ID NO 64
<211> LENGTH: 15
<212> TYPE: PRT
<213> ORGANISM: Artificial Sequence
<220> FEATURE:
<223> OTHER INFORMATION: Synthetic sequence

<400> SEQUENCE: 64

Leu Ile Gly Lys Ser Asn Ile Cys Val Lys Val Gly Glu Lys Ser
1               5                   10                  15

<210> SEQ ID NO 65
<211> LENGTH: 15
<212> TYPE: PRT
<213> ORGANISM: Artificial Sequence
<220> FEATURE:
<223> OTHER INFORMATION: Synthetic sequence

<400> SEQUENCE: 65

Ser Asn Ile Cys Val Lys Val Gly Glu Lys Ser Leu Thr Cys Lys
1               5                   10                  15

<210> SEQ ID NO 66
<211> LENGTH: 15
<212> TYPE: PRT
<213> ORGANISM: Artificial Sequence
<220> FEATURE:
<223> OTHER INFORMATION: Synthetic sequence

<400> SEQUENCE: 66

Val Lys Val Gly Glu Lys Ser Leu Thr Cys Lys Lys Ile Asp Leu
1               5                   10                  15

<210> SEQ ID NO 67
<211> LENGTH: 15
<212> TYPE: PRT
<213> ORGANISM: Artificial Sequence
<220> FEATURE:
<223> OTHER INFORMATION: Synthetic sequence

<400> SEQUENCE: 67

Glu Lys Ser Leu Thr Cys Lys Lys Ile Asp Leu Thr Thr Ile Val
1               5                   10                  15
```

```
<210> SEQ ID NO 68
<211> LENGTH: 15
<212> TYPE: PRT
<213> ORGANISM: Artificial Sequence
<220> FEATURE:
<223> OTHER INFORMATION: Synthetic sequence

<400> SEQUENCE: 68

Thr Cys Lys Lys Ile Asp Leu Thr Thr Ile Val Lys Pro Glu Ala
1               5                   10                  15

<210> SEQ ID NO 69
<211> LENGTH: 15
<212> TYPE: PRT
<213> ORGANISM: Artificial Sequence
<220> FEATURE:
<223> OTHER INFORMATION: Synthetic sequence

<400> SEQUENCE: 69

Ile Asp Leu Thr Thr Ile Val Lys Pro Glu Ala Pro Phe Asp Leu
1               5                   10                  15

<210> SEQ ID NO 70
<211> LENGTH: 15
<212> TYPE: PRT
<213> ORGANISM: Artificial Sequence
<220> FEATURE:
<223> OTHER INFORMATION: Synthetic sequence

<400> SEQUENCE: 70

Thr Ile Val Lys Pro Glu Ala Pro Phe Asp Leu Ser Val Ile Tyr
1               5                   10                  15

<210> SEQ ID NO 71
<211> LENGTH: 15
<212> TYPE: PRT
<213> ORGANISM: Artificial Sequence
<220> FEATURE:
<223> OTHER INFORMATION: Synthetic sequence

<400> SEQUENCE: 71

Pro Glu Ala Pro Phe Asp Leu Ser Val Ile Tyr Arg Glu Gly Ala
1               5                   10                  15

<210> SEQ ID NO 72
<211> LENGTH: 15
<212> TYPE: PRT
<213> ORGANISM: Artificial Sequence
<220> FEATURE:
<223> OTHER INFORMATION: Synthetic sequence

<400> SEQUENCE: 72

Phe Asp Leu Ser Val Ile Tyr Arg Glu Gly Ala Asn Asp Phe Val
1               5                   10                  15

<210> SEQ ID NO 73
<211> LENGTH: 15
<212> TYPE: PRT
<213> ORGANISM: Artificial Sequence
<220> FEATURE:
<223> OTHER INFORMATION: Synthetic sequence

<400> SEQUENCE: 73

Val Ile Tyr Arg Glu Gly Ala Asn Asp Phe Val Val Thr Phe Asn
1               5                   10                  15

<210> SEQ ID NO 74
```

```
<211> LENGTH: 15
<212> TYPE: PRT
<213> ORGANISM: Artificial Sequence
<220> FEATURE:
<223> OTHER INFORMATION: Synthetic sequence

<400> SEQUENCE: 74

Glu Gly Ala Asn Asp Phe Val Val Thr Phe Asn Thr Ser His Leu
1               5                   10                  15

<210> SEQ ID NO 75
<211> LENGTH: 15
<212> TYPE: PRT
<213> ORGANISM: Artificial Sequence
<220> FEATURE:
<223> OTHER INFORMATION: Synthetic sequence

<400> SEQUENCE: 75

Asp Phe Val Val Thr Phe Asn Thr Ser His Leu Gln Lys Lys Tyr
1               5                   10                  15

<210> SEQ ID NO 76
<211> LENGTH: 15
<212> TYPE: PRT
<213> ORGANISM: Artificial Sequence
<220> FEATURE:
<223> OTHER INFORMATION: Synthetic sequence

<400> SEQUENCE: 76

Thr Phe Asn Thr Ser His Leu Gln Lys Lys Tyr Val Lys Val Leu
1               5                   10                  15

<210> SEQ ID NO 77
<211> LENGTH: 15
<212> TYPE: PRT
<213> ORGANISM: Artificial Sequence
<220> FEATURE:
<223> OTHER INFORMATION: Synthetic sequence

<400> SEQUENCE: 77

Ser His Leu Gln Lys Lys Tyr Val Lys Val Leu Met His Asp Val
1               5                   10                  15

<210> SEQ ID NO 78
<211> LENGTH: 15
<212> TYPE: PRT
<213> ORGANISM: Artificial Sequence
<220> FEATURE:
<223> OTHER INFORMATION: Synthetic sequence

<400> SEQUENCE: 78

Lys Lys Tyr Val Lys Val Leu Met His Asp Val Ala Tyr Arg Gln
1               5                   10                  15

<210> SEQ ID NO 79
<211> LENGTH: 15
<212> TYPE: PRT
<213> ORGANISM: Artificial Sequence
<220> FEATURE:
<223> OTHER INFORMATION: Synthetic sequence

<400> SEQUENCE: 79

Lys Val Leu Met His Asp Val Ala Tyr Arg Gln Glu Lys Asp Glu
1               5                   10                  15

<210> SEQ ID NO 80
<211> LENGTH: 15
```

<212> TYPE: PRT
<213> ORGANISM: Artificial Sequence
<220> FEATURE:
<223> OTHER INFORMATION: Synthetic sequence

<400> SEQUENCE: 80

His Asp Val Ala Tyr Arg Gln Glu Lys Asp Glu Asn Lys Trp Thr
1               5                   10                  15

<210> SEQ ID NO 81
<211> LENGTH: 15
<212> TYPE: PRT
<213> ORGANISM: Artificial Sequence
<220> FEATURE:
<223> OTHER INFORMATION: Synthetic sequence

<400> SEQUENCE: 81

Tyr Arg Gln Glu Lys Asp Glu Asn Lys Trp Thr His Val Asn Leu
1               5                   10                  15

<210> SEQ ID NO 82
<211> LENGTH: 15
<212> TYPE: PRT
<213> ORGANISM: Artificial Sequence
<220> FEATURE:
<223> OTHER INFORMATION: Synthetic sequence

<400> SEQUENCE: 82

Lys Asp Glu Asn Lys Trp Thr His Val Asn Leu Ser Ser Thr Lys
1               5                   10                  15

<210> SEQ ID NO 83
<211> LENGTH: 15
<212> TYPE: PRT
<213> ORGANISM: Artificial Sequence
<220> FEATURE:
<223> OTHER INFORMATION: Synthetic sequence

<400> SEQUENCE: 83

Lys Trp Thr His Val Asn Leu Ser Ser Thr Lys Leu Thr Leu Leu
1               5                   10                  15

<210> SEQ ID NO 84
<211> LENGTH: 15
<212> TYPE: PRT
<213> ORGANISM: Artificial Sequence
<220> FEATURE:
<223> OTHER INFORMATION: Synthetic sequence

<400> SEQUENCE: 84

Val Asn Leu Ser Ser Thr Lys Leu Thr Leu Leu Gln Arg Lys Leu
1               5                   10                  15

<210> SEQ ID NO 85
<211> LENGTH: 15
<212> TYPE: PRT
<213> ORGANISM: Artificial Sequence
<220> FEATURE:
<223> OTHER INFORMATION: Synthetic sequence

<400> SEQUENCE: 85

Ser Thr Lys Leu Thr Leu Leu Gln Arg Lys Leu Gln Pro Ala Ala
1               5                   10                  15

<210> SEQ ID NO 86
<211> LENGTH: 15
<212> TYPE: PRT

-continued

<213> ORGANISM: Artificial Sequence
<220> FEATURE:
<223> OTHER INFORMATION: Synthetic sequence

<400> SEQUENCE: 86

Thr Leu Leu Gln Arg Lys Leu Gln Pro Ala Ala Met Tyr Glu Ile
1               5                   10                  15

<210> SEQ ID NO 87
<211> LENGTH: 15
<212> TYPE: PRT
<213> ORGANISM: Artificial Sequence
<220> FEATURE:
<223> OTHER INFORMATION: Synthetic sequence

<400> SEQUENCE: 87

Arg Lys Leu Gln Pro Ala Ala Met Tyr Glu Ile Lys Val Arg Ser
1               5                   10                  15

<210> SEQ ID NO 88
<211> LENGTH: 15
<212> TYPE: PRT
<213> ORGANISM: Artificial Sequence
<220> FEATURE:
<223> OTHER INFORMATION: Synthetic sequence

<400> SEQUENCE: 88

Pro Ala Ala Met Tyr Glu Ile Lys Val Arg Ser Ile Pro Asp His
1               5                   10                  15

<210> SEQ ID NO 89
<211> LENGTH: 15
<212> TYPE: PRT
<213> ORGANISM: Artificial Sequence
<220> FEATURE:
<223> OTHER INFORMATION: Synthetic sequence

<400> SEQUENCE: 89

Tyr Glu Ile Lys Val Arg Ser Ile Pro Asp His Tyr Phe Lys Gly
1               5                   10                  15

<210> SEQ ID NO 90
<211> LENGTH: 15
<212> TYPE: PRT
<213> ORGANISM: Artificial Sequence
<220> FEATURE:
<223> OTHER INFORMATION: Synthetic sequence

<400> SEQUENCE: 90

Val Arg Ser Ile Pro Asp His Tyr Phe Lys Gly Phe Trp Ser Glu
1               5                   10                  15

<210> SEQ ID NO 91
<211> LENGTH: 15
<212> TYPE: PRT
<213> ORGANISM: Artificial Sequence
<220> FEATURE:
<223> OTHER INFORMATION: Synthetic sequence

<400> SEQUENCE: 91

Pro Asp His Tyr Phe Lys Gly Phe Trp Ser Glu Trp Ser Pro Ser
1               5                   10                  15

<210> SEQ ID NO 92
<211> LENGTH: 15
<212> TYPE: PRT
<213> ORGANISM: Artificial Sequence

```
<220> FEATURE:
<223> OTHER INFORMATION: Synthetic sequence

<400> SEQUENCE: 92

Phe Lys Gly Phe Trp Ser Glu Trp Ser Pro Ser Tyr Tyr Phe Arg
1               5                   10                  15

<210> SEQ ID NO 93
<211> LENGTH: 15
<212> TYPE: PRT
<213> ORGANISM: Artificial Sequence
<220> FEATURE:
<223> OTHER INFORMATION: Synthetic sequence

<400> SEQUENCE: 93

Trp Ser Glu Trp Ser Pro Ser Tyr Tyr Phe Arg Thr Pro Glu Ile
1               5                   10                  15

<210> SEQ ID NO 94
<211> LENGTH: 15
<212> TYPE: PRT
<213> ORGANISM: Artificial Sequence
<220> FEATURE:
<223> OTHER INFORMATION: Synthetic sequence

<400> SEQUENCE: 94

Ser Pro Ser Tyr Tyr Phe Arg Thr Pro Glu Ile Asn Asn Ser Ser
1               5                   10                  15

<210> SEQ ID NO 95
<211> LENGTH: 15
<212> TYPE: PRT
<213> ORGANISM: Artificial Sequence
<220> FEATURE:
<223> OTHER INFORMATION: Synthetic sequence

<400> SEQUENCE: 95

Tyr Phe Arg Thr Pro Glu Ile Asn Asn Ser Ser Gly Glu Met Asp
1               5                   10                  15

<210> SEQ ID NO 96
<211> LENGTH: 8
<212> TYPE: PRT
<213> ORGANISM: Artificial Sequence
<220> FEATURE:
<223> OTHER INFORMATION: Synthetic sequence

<400> SEQUENCE: 96

Arg Lys Leu Gln Pro Ala Ala Met
1               5
```

ANTIBODIES AND POLYPEPTIDES DIRECTED AGAINST CD127

CROSS-REFERENCE TO RELATED APPLICATIONS

This is a Divisional of U.S. patent application Ser. No. 16/467,284, filed Jun. 6, 2019, which claims the benefit of International Patent Application PCT/EP2017/081911, filed Dec. 7, 2017, which claims priority to EP 16306655.8, filed Dec. 9, 2016, each of which are incorporated herein by reference in their entireties.

SEQUENCE LISTING STATEMENT

A sequence listing containing the file named 187485_Sequence.txt which is 41,200 bytes (measured in MS-Windows®) and created on Mar. 25, 2021, comprises 96 sequences, is provided herewith via the USPTO's EFS system, and is incorporated herein by reference in its entirety.

The invention is in the field of polypeptides or antibodies useful in therapeutic and diagnostics applications targeting CD127, the alpha chain of the IL7 receptor, and provides in particular humanized monoclonal antibodies against CD127, particularly human CD127, therapeutic uses thereof, and diagnostics applications.

BRIEF DESCRIPTION OF THE INVENTION

The alpha chain (or subunit) of the receptor for interleukin7 (IL-7), is designated CD127 or p90 IL-7R or IL-7Ralpha or IL-7Rα (sometimes also noted IL-7Ra). In a particular aspect, the antibodies, particularly monoclonal antibodies, provided herein are directed against the alpha chain of the receptor for human IL-7 expressed on human cells. In a particular aspect, the antibodies provided herein have antagonist properties for IL-7-IL-7R interaction, may present cytotoxic activity against CD127 positive cells but do not increase the maturation of dendritic cells (DCs) induced by TSLP. In particular, the antibodies provided herein recognize a human CD127 epitope comprising sequences from the 2b site of CD127, in particular the epitope comprises human CD127 sequences of domain D1 and of the 2b site of CD127, in particular the epitope comprises at least one sequence from D1 and at least one sequence from the 2b site, preferably from the third beta sheet of the 2b site of CD127. Alternatively, or in addition, in a particular aspect, the antibodies provided herein do not induce the internalization of CD127 and/or inhibit the IL7-induced internalization of CD127. In a particular aspect, the antibodies provided herein are humanized and comprise at least 80% and preferably at least 84%, or at least 85% of human residues. In a particular aspect, the antibodies provided herein have a fast effect on effector memory T cells, a long-lasting effect on effector memory T cells, or, preferably, a fast and long-lasting effect on effector memory T cells. In a particular aspect, the antibodies provided herein allow for efficient production. In a particular aspect, the expression levels of CD127, IL-7 and/or TSLP may be measured to assess likelihood of response, in particular using the anti-CD127 antibodies provided herein. In addition to antibodies, provided herein, in particular as tools for the production of antibodies and/or for uses similar to said antibodies, are polypeptides, in particular antibody light chain variable domains or antibody light chains, antigen-binding fragments and antibody mimetic molecules from such antibodies and polynucleotides.

The inventors have sought to obtain improved humanized antibodies when compared to the N13B2-h1, N13B2-h2 and N13B2-h3 antibodies disclosed in WO 2015/189302. While it is known that some residues in the variable domain framework sequences, including residues in the Vernier zone, canonical residues, residues at the VH/VL interface, etc., are critical in the structure of an antibody and should not be mutated in order to preserve the biochemical and biological activity of an antibody, the inventors have surprisingly discovered that some mutations within the light chain variable domain framework sequence of N13B2, including some of such critical residues, allow increasing human residue content (higher than N13B2-h3 and up to 86.3%) and improved production (up to 4 times higher than N13B2-h3) while preserving all the functional features.

These mutations consist of 16 amino acid substitutions within the light chain variable domain framework sequence of N13B2 and in particular additionally in the substitution of the valine residue at position 48 by a leucine residue (V48L) and/or in the substitution of the phenylalanine residue at position 87 by a tyrosine residue (F87Y). These positions, and any amino acid positions with antibody chains provided herein, unless otherwise stated, are provided using Kabat numbering. Provided herein are the improved antibody light chain variable domains consisting of the following sequences:

- SEQ ID No: 9 (including said 16 amino acid substitutions—said antibody light chain variable domain being hereinafter designated N13B2-hVL3);
- SEQ ID No: 10 (including said 16 amino acid substitutions and additionally with mutation V48L—said antibody light chain variable domain being hereinafter designated N13B2-hVL4);
- SEQ ID No: 11 (including said 16 amino acid substitutions and additionally with mutation F87Y—said antibody light chain variable domain being hereinafter designated N13B2-hVL5); and
- SEQ ID No: 12 (including said 16 amino acid substitutions and additionally with both mutations V48L and F87Y said antibody light chain variable domain being hereinafter designated N13B2-hVL6).

Thus, the antibody light chain variable domain designated herein N13B2-hVL3, comprises the CDRs of N13B2-h3, said 16 amino acid substitutions and the original residues of N13B2 at critical positions 48 and 87 (i.e., respectively, V and F) within human framework sequences and has the sequence of SEQ ID No: 9. The light chain variable domain of the preferred improved antibody provided herein, designated N13B2-hVL6, comprising in addition both mutations V48L and F87Y, consists of the sequence set forth in SEQ ID No: 12.

The skilled person would not have expected that said mutations, particularly at such positions in the frameworks of the light chain variable domain would leave the affinity of the antibody with CD127 unaffected: V48 is a canonical residue and F87 is located at the VH/VL interface; the mutation of such residues, as is known to the skilled person and discussed in e.g. Clark, 2014, is expected to affect affinity and/or stability of the antibody. As used herein, the term "canonical" residue refers to a residue in a CDR or framework that defines a particular canonical CDR structure as defined by Chothia et al., J. Mol. Biol. 196:901-907 (1987); Chothia et al., J. Mol. Biol. 227:799 (1992). According to Chothia et al., critical portions of the CDRs of many antibodies have nearly identical peptide backbone conformations despite great diversity at the level of amino acid sequence. Each canonical structure specifies primarily a set of peptide backbone torsion angles for a contiguous segment of amino acid residues forming a loop. It was not foreseeable that the introduction of the disclosed mutations at both positions would result in improved production, while still preserving binding features and advantageously other functional features of the antibodies.

Accordingly, provided herein is a polypeptide useful in particular for the production of such antibodies, in particular an antibody light chain variable domain or an antibody light chain, consisting of a sequence, in particular of up to 250 amino acids, comprising or consisting of the sequence set forth in SEQ ID NO: 9; SEQ ID NO: 10; or SEQ ID NO: 11; or SEQ ID NO: 12, or an antigen-binding fragment or antibody mimetic molecule thereof as defined hereinafter. In a particular aspect, the invention relates to antibodies or antigen-binding fragment thereof, provided herein, particularly humanized monoclonal antibodies, specifically bind to CD127, particularly to human CD127, and comprise:

an antibody light chain comprising or an antibody light chain variable domain consisting of a sequence selected from the group consisting of SEQ ID No: 9; SEQ ID No: 10; SEQ ID No: 11; SEQ ID No: 12; in particular SEQ ID No: 12; and an antibody heavy chain variable domain comprising the three CDRs consisting of the sequences set forth in SEQ ID No: 1, SEQ ID No: 2, and SEQ ID No: 3, in particular an antibody heavy chain variable domain consisting of the sequence set forth in SEQ ID No: 7.

In a preferred embodiment, the invention relates to antibodies or antigen-binding fragments thereof, provided herein, particularly humanized monoclonal antibodies, that specifically bind to CD127, particularly to human CD127, and comprise:

a light chain variable domain consisting of a sequence selected from the group consisting of SEQ ID No: 9, SEQ ID No: 10, SEQ ID No: 11 and SEQ ID No: 12, particularly SEQ ID No: 12; and a heavy chain variable domain comprising the three CDRs consisting of the sequences set forth in SEQ ID No: 1, SEQ ID No: 2, and SEQ ID No: 3, in particular a heavy chain variable domain consisting of the sequence set forth in SEQ ID No: 7.

In a particular aspect, the antibody provided herein comprises a light chain with a variable domain as above and a constant domain consisting of a sequence selected among SEQ ID No: 27 or 28, preferably SEQ ID No:27 and a heavy chain with a variable domain as above and a constant domain consisting of the sequence set forth in SEQ ID No:26.

Also provided herein is an isolated polypeptide consisting of a sequence of up to 250 amino acids, in particular of up to 217, of up to 214, of up to 211, more particularly of up to 200, of up to 175, of up to 150, of up to 135, of up to 120, of up to 107 and even more particularly of up to 100, of up to 90, of up to 80, of up to 74, of up to 70, of up to 60 amino acids, wherein said sequence comprises or consist of a sequence selected from the group consisting of:

SEQ ID No: 9 (CDRs of N13B2-h3 within human framework sequences);
SEQ ID No: 10 (CDRs of N13B2-h3 within human framework sequences, including the V48L mutation);
SEQ ID No: 11 (CDRs of N13B2-h3 within human framework sequences, including the F87Y mutation);
SEQ ID No: 12 (CDRs of N13B2-h3 within human framework sequences, including both the V48L and F87Y mutations); and an antigen-binding fragment thereof, particularly said fragment comprising the three CDRs consisting of the sequences set forth in SEQ ID No: 4, SEQ ID No: 5 and SEQ ID No: 6, more particularly a fragment comprising at least 74 amino acids consisting of amino acids 24 to 97 of SEQ ID No:12.

Also provided herein are polynucleotides encoding the polypeptides provided herein, in particular the antibodies or antigen-binding fragments thereof of the invention. Such polynucleotides encode in particular polypeptides comprising or consisting of a sequence selected among the group consisting of SEQ ID Nos:9 to 12, and also encode polypeptides comprising or consisting of sequences selected among SEQ ID Nos:1 to 3, particularly SEQ ID No: 7, and may also encode polypeptides comprising or consisting of sequences selected from the group consisting of SEQ ID Nos: 26 to 28. In particular, said polynucleotides comprise or consist in the combination of at least two isolated nucleic acid sequences (molecules), a first isolated nucleic acid molecule comprising or consisting of a sequence selected among the group consisting of SEQ ID Nos:15 to 18; in particular SEQ ID No: 18; said combination also comprising or consisting of a second isolated nucleic acid molecule comprising or consisting of a sequence selected from the group consisting of SEQ ID No: 13 and SEQ ID Nos: 29 to 31, in particular SEQ ID No: 13.

In particular, the polypeptide according to the invention comprises an antibody light chain variable domain or an antibody light chain, said polypeptide comprising at least 84% and more particularly at least 85% of human residues. Said polypeptide can be an antigen-binding fragment and/or an antibody-mimetic molecule from an antibody disclosed herein.

Provided herein are also compositions comprising said polypeptides, in particular antibody light chain variable domains or antibody light chains, antibodies, antigen-binding fragment or antibody mimetic molecule thereof, methods of obtaining said antibodies, nucleic acid molecules encoding said polypeptides and antibodies and uses of said polypeptides, antibodies and compositions.

Accordingly the polypeptides, antibody light chain variable domains, antibody light chains, antibodies, antigen-binding fragments, antibody mimetic molecules and composition provided herein may be intended and/or suitable for use in order to remedy to a condition diagnosed in a human patient which results from pathogenesis related to lymphopoiesis, when IL-7 signalling pathways provide contribution to said pathogenesis, especially when an increase in the maturation, more precisely the upregulation of costimulatory molecules, of dendritic cells is undesirable.

DETAILED DESCRIPTION OF THE INVENTION

Biochemistry

CD127 is common to the IL-7 receptor (IL-7R) and to the TSLP receptor (TSLPR). The IL-7R is constituted of a heterodimer of CD127 and the common gamma chain (γc) of interleukin receptors. The common gamma chain γc is sometimes referred to herein and in the literature as CD132. IL-7R is bound by Interleukin 7. The TSLP receptor is a heterodimer of CD127 and cytokine receptor-like factor 2 (CRLF2). The TSLP receptor is bound by TSLP. In the literature, TSLPR is sometimes used to designate both the CRLF2 chain of the receptor, and the CD127/CRLF2 complex. In order to avoid confusion, in what follows TSLPR usually designates the complex.

CD127 (Swiss Prot accession number P16871) may exist in four isoforms. The canonical isoform, also termed H2O (Swiss Prot P16871.1) is a single-pass transmembrane protein and has 459 amino acids consisting, from N- to C-terminal, of a 20 amino-acid signal peptide, a 219 amino acid extracellular domain, a 25 amino-acid transmembrane domain and a 195 amino-acid intracellular domain. Other isoforms share the sequence of all of (or most of) the extracellular domain of H2O and display varied C-terminal sequences. Isoforms 2 and 4 are secreted (Swiss Prot P16871-4 and P16871-3), while isoform 3 (Swiss Prot P16871-2) is also a transmembrane protein. CD127 is reported to have the sequence of SEQ ID No: 21, and its extracellular domain, when the signal peptide is removed, has the sequence of SEQ ID No: 22. Unless otherwise stated, the numbering used herein for amino acids of CD127 is the numbering from SEQ ID No: 22.

CD127 is a Cytokine Receptor Homology class I (CRH I) receptor. As is well known in the art, the extracellular domain of these receptors consists of two fibronectin 3 domains, termed D1 and D2. The precise crystallographic structure of CD127 has been published and discussed in e.g. McElroy et al., 2009; McElroy et al., 2012 and Walsh, 2012 and in particular has been disclosed as protein structure data in the Research Collaboratory for Structural Bioinformatics Protein Data Bank (RCSB PDB) database, with the accession number 3UP1. D1 is generally considered to be involved in the binding with IL-7, while D2 is involved in the binding to the yc chain (and also with IL-7). Importantly, the site 2b of domain D2 comprises three beta sheets including the following sequences SEQ ID No: 32 (FDLSVIYRE); SEQ ID No: 33 (NDFVVTFNTS) and SEQ ID No: 34 (TKLTLLQR). The site 2b of domain D2 is therefore included between amino acids 109 and 180 of SEQ ID No: 22 (see Walsh, 2012; Verstraete, K. et al., Nature Com 2017). The site 2b of domain D2 may also be defined as being included between amino acids 109 and 173 of SEQ ID No: 22. The site 2b of domain D2 may also be defined as being included between amino acids 113 and 180 of SEQ ID No: 22. The site 2b of domain 2b may also be defined as being inlcuded between amino acids 113 and 173 of SEQ ID No: 22. Particularly, the site 2b of domain D2 comprises, in particular consists essentially of, amino acids 109 to 133 of SEQ ID No: 22, in particular 109 to 127, wherein the first two beta sheets are localized; and amino acids 166 to 180 of SEQ ID No: 22, wherein the third beta sheet is localized. More particularly, the 2b site consists essentially of amino acids 113 to 133, in particular 113 to 127, of SEQ ID No: 22 and of amino acids 166 to 180 of SEQ ID No: 22. More particularly, the 2b site consists essentially of amino acids 109 to 133, in particular 109 to 127, of SEQ ID No: 22 and of amino acids 166 to 173 of SEQ ID No: 22. More particularly, the 2b site consists essentially of amino acids 113 to 133, in particular 113 to 127, of SEQ ID No: 22 and of amino acids 166 to 173 of SEQ ID No: 22. The site 2b of domain D2 is critical for the CD127-yc interaction, in particular to allow or increase binding of CD127 with yc in the presence of IL-7. In particular, mutations at P112 and L115, which have been identified in patients suffering from Severe combined immunodeficiency (SCID), are thought to destabilize the hydrophobic core of the D2 domain which likely results in their pathogenic feature. As said above, the 2b site consists essentially of amino acids 109 to 180 of SEQ ID No: 22, or consists essentially of amino acids 109 to 173 of SEQ ID No: 22, or consists essentially of amino acids 113 to 180 of SEQ ID No: 22, or consists essentially of amino acids 113 to 173 of SEQ ID No: 22. The skilled person will appreciate that the extremities of such a domain may not necessarily be defined unambiguously with a single-base precision and that the 2b site may be understood to comprise, at either or both ends of the mentioned sequence(s), 1, 2, or 3 more or less amino acids. Therefore, when referring herein to the 2b site of CD127, this should be understood to refer to a sequence of CD127 starting at position 106, 107, 108, 109, 110, 111, 112 or 113 and ending at position 173, 174, 175, 176, 177, 178, 179 or 180 of SEQ ID No: 22; in particular to such a sequence which is thought or shown to constitute an essential binding site with the yc chain of the IL7-R, in particular in the presence of IL-7. More particularly, when referring herein to the 2b site of CD127, this should be understood to refer to a sequence of CD127 starting at position 106, 107, 108, 109, 110, 111, 112 or 113 and ending at position 124, 125, 126, 127, 128, 129, 130, 131, 132 or 133 of SEQ ID No: 22, but also to a sequence of CD127 starting at position 162, 163, 164, 165 or 166 and ending at position 173, 174, 175, 176, 177, 178, 179 or 180 of SEQ ID No: 22. It should be noted that the three beta sheets as defined herein may comprise epitope sequences specific for antibodies or antigen-binding fragments or antigen-biding mimetic according to the invention. Antibodies, antigen-binding fragments and antigen-binding mimetics according to the invention may be able to specifically bind to SEQ ID No: 32, SEQ ID No: 33 and/or SEQ ID No: 34. Furthermore, an amino acid sequence comprising at least a portion of one beta sheet and some contiguous amino acids localized at one end of any beta sheet may also be an epitope sequence specific for an antibody according to the invention. As an example, the sequence SEQ ID No: 35 (TLLQRKLQPAAMYEI) comprises the last five amino acids of the third beta sheet and ten extra amino acids localized outside the third beta sheet. As another example, the SEQ ID No: 96 (RKLQPAAM) comprises one amino acid localized within the third beta sheet and seven extra amino acids localized outside the third beta sheet. In particular, the antibody or antigen-binding fragment thereof or antigen-binding mimetic according to the invention may specifically bind to R173 of SEQ ID No: 22. In particular, the antibody or antigen-binding fragment thereof or antigen-binding mimetic according to the invention may specifically bind to at least one sequence selected from the group consisting of SEQ ID No: 32; SEQ ID No: 33; SEQ ID No: 34, SEQ ID No: 35 and SEQ ID N No: 96. In particular, the antibody or antigen-binding fragment thereof or antigen-binding mimetic according to the invention may specifically bind to at least one sequence selected from the group consisting of SEQ ID No: 36 (LVEVKCLNFR); SEQ ID No: 37 (ICGALVEVKCLNFR) and SEQ ID No: 38 (LVEVKCLNFRK). Alternatively or complementarily, the antibody or antigen-binding fragment thereof or antigen-binding mimetic according to the invention may specifically bind to at least one sequence selected from the group consisting of SEQ ID No: 39 (KKFLLIG); SEQ ID No: 40 (KKFLLIGKSNI) and SEQ ID No: 41 (FIETKKFLLIG). SEQ ID No: 36 to SEQ ID No: 41 are localized within the domain D1 of CD127 and are epitope sequences recognized by an antibody or antigen-binding fragment thereof or an antibody mimetic molecule according to the invention. In an alternative or complementary embodiment of the invention, the antibody or antigen-binding fragment thereof or an antibody mimetic molecule according to the invention may specifically bind to at least one sequence selected from the group consisting of SEQ ID No: 42 (CLNFR) and SEQ ID No: 43 (FIETKKF). These two sequences are epitope sequences localized within the domain D1 of CD127. In a particular embodiment of the invention, the antibody or antigen-binding fragment or antigen-binding mimetic according to the invention may specifically bind to at least one sequence selected from the group consisting of SEQ ID No: 32; SEQ ID No: 33; SEQ ID No: 34, SEQ ID No: 35 and SEQ ID No: 96, in particular from the group consisting of SEQ ID No: 34, SEQ ID No: 35 and SEQ ID No: 96; and at least one sequence selected from the group consisting of SEQ ID No: 36; SEQ ID No: 37; SEQ ID No: 38; SEQ ID No: 39; SEQ ID No: 40; SEQ ID No: 41; SEQ ID No: 42 and SEQ ID No: 43, in particular from the group consisting of SEQ ID No: 42 and SEQ ID No: 43. In a preferred embodiment of the invention, the antibody or antigen-binding fragment or antigen-binding mimetic may specifically bind to SEQ ID No: 34 and at least one sequence selected from the group consisting of SEQ ID No: 42 and SEQ ID No: 43, in particular to SEQ ID No: 42 and SEQ ID No: 43. In a preferred embodiment of the invention, the antibody or antigen-binding fragment or antigen-binding mimetic may specifically bind to SEQ ID No: 35 and at least one sequence selected from the group consisting of SEQ ID No: 42 and SEQ ID No: 43, in particular to SEQ ID No: 42 and SEQ ID No: 43. In a preferred embodiment of the invention, the antibody or antigen-binding fragment or antigen-binding mimetic may specifically bind to SEQ ID No: 96 and at least one sequence selected from the group consisting of SEQ ID No: 42 and SEQ ID No: 43, in particular to SEQ ID No: 42 and SEQ ID No: 43. In a preferred embodiment of the invention, the antibody or antigen-binding fragment or antigen-binding mimetic may specifically bind to both sequences SEQ ID No: 35 and SEQ ID No: 96. In a preferred embodiment of the invention, the antibody or antigen-binding fragment or antigen-binding mimetic may specifically bind to both sequences SEQ ID No: 42 and SEQ ID No: 43. In a particular embodiment of the invention, the antibody or antigen-binding fragment or antigen-binding mimetic according to the invention may specifically recognize at least the third beta sheet of the site 2b of domain D2 of CD127. The third beta sheet is preferentially defined as being localized between amino acids 166 and 173 of SEQ ID No: 22, corresponding to SEQ ID No: 34, and more particularly the third beta corresponds to SEQ ID No: 34. In a more particular embodiment of the invention, the antibody or antigen-binding fragment or antigen-binding mimetic according to the invention may specifically recognize at least two of the beta sheets localized within the site 2b of domain D2, and more particularly, the antibody or antigen-binding fragment or antigen-binding mimetic according to the invention may specifically recognize the three beta sheets localized within the site 2b of domain D2 as defined here above. In a more particular embodiment of the invention, the antibody or antigen-binding fragment or antigen-binding mimetic may specifically recognize at least one beta sheet localized within site 2b of domain D2, in particular the third beta sheet corresponding to SEQ ID No: 34, and bind to at least one sequence selected from the group consisting of SEQ ID No: 36; SEQ ID No: 37; SEQ ID No: 38; SEQ ID No: 39; SEQ ID No: 40; SEQ ID No: 41; SEQ ID No: 42 and SEQ ID No: 43. In a preferred embodiment of the invention, the antibody or antigen-binding fragment or antigen-binding mimetic may specifically recognize at least the third beta sheet corresponding to SEQ ID No: 34, and at least one sequence selected from the group consisting of SEQ ID No: 42 and SEQ ID No: 43, in particular to SEQ ID No: 42 and SEQ ID No: 43. In a more particular embodiment of the invention, the antibody or antigen-binding fragment or antigen-binding mimetic may specifically recognize a linear peptide or a linear epitope consisting of amino acids of SEQ ID No: 35. Alternatively or complementarily, the antibody or antigen-binding fragment or antigen-binding mimetic may specifically recognize a conformational peptide or a conformational epitope consisting of the amino acids of SEQ ID No: 96. In a more particular embodiment, the antibody or antigen-binding fragment or antigen-binding mimetic may specifically recognize a linear epitope or a linear peptide of the amino acid sequence of SEQ ID No: 35, and a conformational epitope or a conformational peptide of SEQ ID No: 96.

IL-7R signalling. Binding of IL-7 to IL-7R triggers the activation of several signalling pathways, including the Janus kinases (JAK)-1 and -3, signal transducer and activator of transcription 5 (STAT5) and phosphatidylinostol 3-kinase (PI3-k). STAT1 and STAT3 pathways are reported to be activated, although they do not seem to be the main pathways. The activation of the STAT5 pathway is required for the induction of the anti-apoptotic protein Bcl-2 and the prevention of the entry of the pro-apoptotic protein Bax in the mitochondrion and thus for survival of thymic developing T cell precursors. The activation of the PI3-k pathway results in the phosphorylation and cytoplasmic retention of the pro-apoptotic protein Bad.

TSLPR signalling. Thymic Stromal Lymphopoietin, (TSLP) is an epithelial Cell Cytokine that is active in lymphopoiesis and in particular is involved in regulation of development of cells of the immune system, said regulation impacting in particular the maturation of said cells. Human TSLP (Genbank accession number AF338732) is a factor which exerts polarization of dendritic cells and promotes T and B cell proliferation and differentiation. TSLP also suppresses the generation of Treg cells (Lei et al., 2011).

TSLP-induced signaling pathways have been shown to be different, at the molecular level, from IL-7-induced pathways. In particular, while TSLP binding to its receptor also activates Jak-1, it does not activate Jak-3 but does activate Jak-2. These differences are consistent with the observation that Jak-1 associates with CD127, shared by both receptors while Jak-2 associates with CRLF2 and Jak-3 with yc (Rochman et al., 2010). The activation of the STAT5 pathway is also reported for TSLP-induced signaling (Zhong et al., 2014). One major effect of TSLP is to lead to the activation of dendritic cells, inducing the overexpression of costimulatory molecules such as CD80, thereby promoting TH-2 mediated inflammatory responses (Reche et al., 2001).

Cellular Biology

"CD127-positive cells" designates cells expressing CD127 at their cell surface. In most cases, CD127-positive cells express CD127 in a complex forming the IL-7R (IL-7R-positive cells) and/or in a complex forming the TSLPR (TSLPR-positive cells). CD127 is expressed by various cells, including by both memory and naive T cells. CD127 is in particular expressed by effector T cells (Teff), including resting and memory T cells, and by immature B cells, but is especially not expressed by resting natural regulatory T cells (natural Treg). CD127 is essential for promoting thymocyte differentiation and clonal expansion of lymphocytes.

The importance of the IL7-CD127 pathway for naive T-cell homeostasis is underlined by several recent studies showing that expression levels of membrane-bound CD127 on conventional $CD4^+$ T cells correlate with frequencies of recent thymic emigrant (RTE)-$CD4^+$ T cells in healthy individuals and HIV-infected patients as well as in patients with MS (Albuquerque et al., 2007) (Broux et al., 2010). CD127 is also a component of the TSLP receptor. The secretion of TSLP by Hassall's corpuscles, structures composed of epithelial cells in the thymic medulla, has been demonstrated to condition CD11c+myeloid dendritic cells (MDCs) to induce the differentiation of thymocytes into Treg (Watanabe et al., 2005a). Accordingly, signals from the IL-7 receptor are required for Treg development as shown in CD127 knockout mice (Mazzucchelli et al., 2008). In (Haas et al., 2011), the authors showed a reduced CD127 expression on conventional T cells and upregulated IL-7 plasma levels together with reduction of recent thymic emigrant-Treg frequencies and Treg function in MS, without clear genetic influence (Haas et al., 2011).

Dissecting how IL-7 regulates its cognate receptor membrane trafficking is crucial to the in-depth understanding of the role of IL-7/IL-7R in lymphocyte function. Previous studies have suggested that IL-7 stimulation of T cells leads to surface down-modulation of CD127 within 30 minutes, possibly because of receptor internalization. At later time points (2-6 hours), IL-7 was shown to induce transcriptional down-regulation of CD127. However, the actual dynamics of CD127 internalization and the regulation of trafficking mechanisms by IL-7 remain to be elucidated (Henriques et al., 2010). It was also suggested that IL-7-induced signaling is dependent on CD127 internalization and that subsequent receptor degradation relies on JAK3 activity and is mediated by both proteasomes and lysosomes.

Physiopathology

Dendritic cells express high levels of costimulatory molecules after maturation, such as CD80, which promotes T cell mediated immune responses. They also produce the cytokine TARC (CCL17), which induces chemotaxis in T cells. As such, mature dendritic cells contribute to the physiopathology of several immune-mediated diseases where T cell responses are at play, as for example in asthma, rheumatoid arthritis, colitis, multiple sclerosis and uveitis. Mature dendritic cells also play a key role in the rejection process of cells, tissues or organ allografts. Therefore, many therapeutic strategies aim at preventing dendritic cells maturation.

The presence or absence of costimulatory molecules on antigen-presenting cells (APCs), such as dendritic cells significantly influences the qualitative and quantitative nature of an immune response. Overexpression of CD80 by dendritic cells causes DC maturation and increases memory T cell activation (Bour-Jordan et al., 2011). Mechanistically, interaction of CD28 with CD80 occupies the central cluster of the immunological synapse and is colocalized with the engaged TCR, thereby stabilizing the immune synapse (Dustin and Shaw, 1999) (Grakoui et al., 1999). The interaction between CD28 and CD80 actually generates the appropriate spacing for TCR to efficiently interact with HLA molecules (Shaw and Dustin, 1997).

Multiple sclerosis (MS) is an inflammatory demyelinating disease of the central nervous system (CNS). The appearance of demyelinating patches in the CNS of patients with MS is associated with an inflammatory infiltrate mainly composed of macrophages and T lymphocytes. On a mechanistic level, the MS is considered as an autoimmune disease. MS is typically considered as a disease primarily mediated by CD4+T cells. Particular subsets of CD4+: Th1 and more recently Th17, were implicated in the pathophysiology of the disease. At present, it is still difficult to assign specific roles to each subpopulation Th 1 and Th17. Furthermore, inhibition of leucocyte trafficking by antagonism of the alpha4 (α4)-integrin has now been validated as a therapeutic approach for the treatment of inflammatory diseases such as MS and inflammatory bowel disease (IBD) and as well for the treatment of atherosclerosis (Zhi et al., 2014). α4β7 is expressed on a more restricted set of leucocytes including activated macrophage, subsets of lymphocytes, NK cells, mast cells and eosinophils.

Human IL-7 induces strong expression of α4 and β7 integrins in vitro on human T lymphocytes and dramatically increases the frequency of human T lymphocytes expressing α4, β7 and α4/β7 integrins, which are required for T lymphocytes homing and retention in non-lymphoid tissues such as intestine, brain and skin (Denucci et al., 2009; Gorfu et al., 2009).

Naive T cells are partly responsible for acute rejection of transplanted organs and tissues. These cells can be controlled by current immunosuppressive drugs (calcineurin inhibitors) and by monoclonal antibodies that block costimulation (anti-adhesion, CD80186 inhibitors). Memory T cells are also responsible for transplant rejection. Memory T cells accumulate in man due to the acquired immune history, mainly former reactions against viruses. It has been shown that memory T cells can be reactivated by alloantigens as a result of "heterologous immunity", which is the cross-reaction of our anti-viral defenses with alloantigens (Adams et al., 2003). Heterologous immunity represents a potent barrier to tolerance induction since memory T cells, in contrast to naive T cells, are programmed to activate quickly, with a reduced requirement for costimulatory signals. Memory T cells may also be involved in chronic rejection. Beside their role in organ and tissue transplantation, naïve and memory T cells are also co-responsible for many autoimmune diseases. This is the case for ulcerative colitis (Shinohara et al., 2011), rheumatoid arthritis, psoriasis or graft-versus-host disease.

Inflammatory bowel diseases (IBD), such as ulcerative colitis (UC) and Crohn's disease (CD), are chronic relapsing gastrointestinal disorders characterized by chronic intestinal inflammation, dysregulated immune responses to intestinal microbiota and dysfunction of the epithelial barrier (Khor et at., 2011; Abraham and Cho, 2009). The incidence and prevalence rates of IBD are increasing worldwide and these diseases are associated with marked morbidity and have a major impact on quality of life and ability to work (Danese and Fiocchi, 2011; Baumgart and Sandbom, 2012). Current conventional treatments aim at dampening inflammation with the gradual use of anti-inflammatory agents, immunosuppressive drugs and biological agents targeting inflammatory cytokines such as tumor necrosis factor alpha (TNFα). A key feature of IBD is also the rapid recruitment and prolonged persistence of leukocytes at the site of inflammation, which is permitted by integrins interaction with cognate receptors expressed by endothelial cells allowing cell adhesion and transmigration (Adams and Eksteen, 2006; Agace, 2006). Emerging therapies are targeting this entry-door to the gut with anti-adhesion molecules, specially targeting the gut-specific α4β7 integrins pathway (Feagan et al., 2013; Sandbom et al., 2013)[7,8]. However, these therapies do not maintain remission in more than half of patients, relapsing flares occurring in a high proportion of primary responders. Opportunistic infections also develop as consequence of general immunosuppression. Thus, one major goal is to provide novel treatments for IBD and to identify markers which determines the chronicity, response and relapse of IBD.

Furthermore, several malignant cells have been shown to display IL-7R. This is the case for Sezary cutaneous lymphoma (60% of them), or childhood acute lymphoblastic leukemia in which about 15% of the cases develop gain-of-function mutation in CD127, rendering these tumors partially IL-7 dependent (Shochat et al., 2011).

The depletion of T lymphocytes has been an obvious immunosuppressive approach to counteract allograft rejection or fight autoimmunity. However, total T cell depletion might not be favorable for the induction of immunological tolerance. Targeting T cell subpopulations or selectively activated T cells, without modifying Treg cells, could constitute a pro-tolerogenic approach (Haudebourg et al., 2009). CD127 may thus be regarded as a potential attractive therapeutic target for monoclonal antibodies (Mabs) aimed at modulating immune responses since such monoclonal antibodies could have the potential of depleting effector but not regulatory lymphocytes. It has been assumed accordingly that they might show efficacy in transplantation, autoimmunity (Michel et al., 2008) and malignancies by antagonizing access of IL-7 to IL-7-R and thereby limiting T and B cell function and growth.

A therapy with a monoclonal antibody against CD127+ cells that interferes with the IL-7 pathway could fulfill that goal by eliminating/neutralizing naïve and memory T cells and/or reducing their number while preserving Treg cells or by eliminating or reducing the number of CD127-positive malignant cells. A therapy with a monoclonal antibody against CD127+ cells might however act as a double edge sword if it leads to dendritic cells activation. Indeed, CD127 is also expressed by dendritic cells in association with CRLF2, forming the TSLP receptor. In the presence of TSLP, dendritic cells get activated and promote T cell-mediated immune responses. Some monoclonal antibodies against CD127, presumably by modifying the way TSLP interacts with TSLP receptor, have the property to increase the maturation of dendritic cells induced by TSLP. As a consequence, a therapy with a monoclonal antibody against CD127 that would not increase the maturation of dendritic cells induced by TSLP would present a therapeutic advantage. It would present the benefit of IL7R blockade without the drawback of activating dendritic cells in an inflamed environment containing TSLP.

In a publication (Racape et al., 2009) the authors analyzed the interest of IL-7 receptor alpha (IL7Rα) as a potential therapeutic target in transplantation. Having reviewed the expression of IL-7Rα, on various T cells and IL-7 responsive cells, the authors determined whether targeting memory T cells expressing IL-7Rα could prolong allograft survival in mice and conclude that targeting IL-7 or IL-7Rα, would advantageously spare Treg cells. Among the perspectives, the authors pointed out that targeting either IL-7 or IL-7Rα in therapeutic treatment might have different consequences on the survival of the cells expressing CD127 and might elicit different types of lymphopenia. The question of the effects of antibodies that would be directed against IL-7Rα, depending upon whether they would be blocking or neutralizing or cytotoxic antibodies was also posed from a conceptual point of view. The authors nevertheless did not show having obtained and assayed such antibodies and rather expressed the need for further study to assess the relevancy of the hypothesis.

In view of the drawbacks of available therapeutic approaches in immune related diseases and other diseases involving the IL-7/IL-7Rα such as different types of cancers, including some breast cancers, there is still a need for further drug candidates, especially for candidates active with respect to more selective targets for the purpose of controlling e.g. modulating immune activation in human patients.

In this context, monoclonal antibodies against IL-7Rα, having antagonist properties toward IL-7Rα, have been disclosed in WO2010/017468 and their humanized versions in WO2011/094259 with a view to treat autoimmune diseases like multiple sclerosis. The described antibodies are said to be antagonist for IL-7 binding to its receptor, and active against TH17 and TH1 cells expansion and survival which were said to require IL-7 interaction with their CD127 receptor. The effect of these antibodies on the maturation of immune cells, and particularly of dendritic cells, has not been considered. Besides, these antibodies are said not to inhibit TSLP-induced production of TARC (p. 107 of WO2011/094259). Similarly, anti-CD127 antibodies reported in WO2011/104687 or in WO2013/056984, which are contemplated for use in the treatment of diabetes, lupus, rheumatoid arthritis and other autoimmune diseases, have not been discussed with respect to their possible effect on the maturation of dendritic cells and their interaction with TSLP-induced signaling has not been reported. In addition, as published by Kern et al (Kern et al., 2013; Kern et al., 2015) and as shown herein, the anti-CD127 antibodies of the prior art induce internalization of the receptor. Since antagonist anti-CD127 antibodies that also induce internalization of CD127 fail to control cutaneous type IV hypersensitivity, whereas antagonist anti-CD127 antibodies that do not induce internalization do, it might be that the internalization process activates the signaling pathway, mitigating the antagonist effect of the antibodies. Last, the antibodies of the prior art recognize an epitope which does not comprise any sequence from the 2b site of CD127 (i.e. in particular from amino acids 109-180 of SEQ ID No:22, or in particular from amino acids 109-173 of SEQ ID No: 22, or in particular from amino acids 113-180 of SEQ ID No: 22, or in particular from amino acids 113-173 of SEQ ID No: 22); and have not been shown to disrupt the binding of CD127 with the γc chain of the IL7-R.

Despite recent interest in the development of CD127 antibodies, efforts have thus concentrated on the inhibition of IL7-induced IL-7R signaling. Nonetheless, TSLP and the TSLPR have been involved in a number of pathologies. TSLP has been shown to play a role in skin and lung diseases (He and Geha, 2010) and to associate to various pathologies including airway inflammatory disease and atopic dermatitis in human and mice (Ying et al., 2008) (Jariwala et al., 2011). In addition TSLP has been shown to associate to regulation of intestinal immunity and inflammation (Taylor et al., 2009). Other pathologies involving TSLP and the TSLPR include pediatric B-cell leukemia (van Bodegom et al., 2012), lung- and skin-specific allergic disorders, autoimmunity-related diseases (Roan et al., 2012) and cancer, including breast cancer (Olkhanud et al., 2011).

Antibodies that do not display the effect of increasing the maturation of dendritic cells and/or that do not induce internalization of CD127 and/or that inhibit IL7-induced internalization were disclosed in WO 2015/189302. Said antibodies, termed N13B2 (chimeric antibody), N13B2-h1, N13B2-h2 and N13B2-h3 (humanized N13B2) in said application and hereinafter, have high efficiency, especially in vivo and in particular were shown to have a fast effect on effector memory T cells, as defined hereinafter. However, said antibodies are humanized to a limited extent and their production efficiency is also limited. Moreover, no long-lasting effect of said antibodies on effector memory T cells has been reported.

The invention relates to tools for the design of novel antibodies suitable as therapeutic candidates for the administration to patients with or at risk of a disease involving IL-7 signaling pathways. According to various approaches provided herein, such tools improve preparation of antibodies intended for administration to human hosts. Such tools comprise in particular humanized, particularly monoclonal, antibodies which comprise all the CDRs sequences of N13B2-h3.

Such polypeptides (or polynucleotides encoding such polypeptides) are provided in particular for the production of antibodies (or antigen-binding fragments thereof) and/or as antibodies (or antigen-binding fragments thereof), particularly which specifically binds to CD127; said antibodies, in particular monoclonal antibodies, comprise a heavy chain variable domain comprising the three CDRs sequences VHCDR1 set forth in SEQ ID No: 1, VHCDR2 set forth in SEQ ID No: 2 and VHCDR3 set forth in SEQ ID No: 3. In particular, said heavy chain variable domain consists of the sequence set forth in SEQ ID No: 7 or has said sequence with additional mutations, in particular substitution, deletion or insertion of four residues, preferably three or two residues and even more preferably one residue, preferably wherein said mutations are neither in the CDR sequences nor in canonical or Vernier positions of the framework sequences.

The antibodies provided herein are preferably monoclonal antibodies, meaning that a composition of these antibodies is homogeneous, especially identical, in terms of antigen-binding specificity and accordingly in terms of variable region composition.

The invention provides antibodies which share the CDRs of the N13B2-h3 antibody but have a distinct light chain variable domain framework. The inventors have surprisingly shown that antibodies comprising the same CDRs of the light chain variable domain of N13B2-h3, i.e. the CDRs with SEQ ID No: 4 and 5 and 6 but comprising a different light chain variable domain sequence, i.e. of SEQ ID No: 9; of SEQ ID No: 10; of SEQ ID No: 11 or of SEQ ID No: 12; while humanized extensively, are highly produced compared to N13B2-h3 (up to 4 times higher), while preserving all the functional features.

The invention provides means suitable in this context, comprising in particular specific monoclonal antibodies against IL-7Rα. In particular embodiments, said antibodies interfere only negatively with the TSLP pathway. Accordingly, in preferred embodiments said antibodies do not increase TSLP-induced dendritic cell maturation. In addition or alternatively, in particular embodiments, said antibodies do not induce internalization of CD127 and/or inhibit IL7-induced internalization of CD127. In particular embodiments, said antibodies combine these DC maturation- and/or internalization-related properties with antagonist activity toward IL-7/IL-7-R signalling. In particular embodiments, said antibodies inhibit IL7-induced expression of α4, β7 and α4/β7 integrins in T cells, in particular in vivo. In particular embodiments, said antibodies exert a cytotoxic action against target CD127+ cells that physically reduce their number (contraction of the subpopulation). In addition or alternatively, in particular embodiments said antibodies comprise at least 80%, preferably at least 84%, or more than 84% and even more preferably at least 85% of human residues as defined hereinafter. In addition or alternatively, in particular embodiments said antibodies are produced at least as efficiently as N13B2-h3, preferably at least twice as efficiently, as defined hereinafter. In addition or alternatively, in particular embodiments said antibodies have rapid and/or a long-lasting effect on effector memory T cells.

In particular, the antibodies provided herein comprise a variable heavy (VH) chain comprising the following amino acid sequences:

VHCDR1; SEQ ID No: 1

VHCDR2; SEQ ID No: 2

VHCDR3. SEQ ID No: 3

The antibodies provided herein preferably comprise a VH chain consisting of the sequence set forth in SEQ ID No: 7:

QVQLVESGGGLVKPGGSLRLSCAVSGFTLSDYYMAWIRQAPGKGLEWVSTI

SASGLRTYYPDSVKGRFTISRDNAKNSLYLQMNSLRAEDTAVYYCARPLSA

HYGFNYFDYWGQGTLVTVSS.

Said variable heavy chain is in particular linked to the constant heavy chain consisting of the sequence of SEQ ID No: 26 to constitute a complete antibody heavy chain.

In particular, the antibodies provided herein comprise a VL chain consisting of a sequence selected from the group consisting of the sequence of SEQ ID No: 9, SEQ ID No: 10, the sequence of SEQ ID No: 11, and the sequence of SEQ ID No: 12, in particular the sequence of SEQ ID No: 12:

DIQMTQSPSSLSASVGDRVTITCRTSEDIYQGLAWYQQKPGKAPKLLLYSA

NTLHIGVPSRFSGSGSGTDYTLTISSLQPEDFATYYCQQYYDYPLAFGGGT

KVEIK.

Said variable light chain is in particular linked to the constant light chain consisting of a sequence selected from SEQ ID No: 27 and SEQ ID No: 28, in particular SEQ ID No: 27, to constitute a complete antibody light chain.

In particular, the antibody or antigen-binding fragment thereof according to the invention, specifically binds to CD127, in particular to human CD127 and comprises:
  an antibody light chain comprising or an antibody light chain variable domain consisting of a sequence selected from the group consisting of SEQ ID No: 9; SEQ ID No: 10; SEQ ID No: 11; SEQ ID No: 12; in particular SEQ ID No: 12; and
  an antibody heavy chain variable domain comprising the three CDRs consisting of the sequences set forth in SEQ ID No: 1, SEQ ID No: 2, and SEQ ID No: 3, in particular an antibody heavy chain variable domain consisting of the sequence set forth in SEQ ID No: 7.

In a more particular embodiment of the invention, the antibody or antigen-binding fragment thereof, specifically binds to CD127, in particular to human CD127 and comprises:
  an antibody light chain variable domain or an antibody light chain according to the invention, particularly consisting of a sequence selected from the group consisting of SEQ ID No: 9, SEQ ID No: 10; SEQ ID No: 11 and SEQ ID No: 12, in particular SEQ ID No: 12; and
  an antibody heavy chain variable domain comprising the three CDRs consisting of the sequences set forth in SEQ ID No: 1, SEQ ID No: 2, and SEQ ID No: 3, in particular an antibody heavy chain variable domain consisting of the sequence set forth in SEQ ID No: 7.

Binding of CD127

In accordance to the invention, "binding" to the IL-7Rα, protein refers to an antigen-antibody type interaction and encompasses "specific binding" properties of the antibodies or antigen-binding fragments thereof which specific binding means that the antibodies or antigen-binding fragments bind to the IL-7Rα protein while they do not bind or bind with a significantly weaker affinity to other proteins (e.g. the common cytokine receptor γ-chain). Specific binding is preferably defined and/or determined in physiological conditions, especially in terms of pH and salt content of the testing solution. Binding and binding specificity can be assayed in accordance with the tests disclosed in the Examples and in particular can be assayed by biosensor, Blitz, Biacore, ELISA, or Western Blot analysis.

In particular embodiments, the antibodies provided herein target and bind the IL-7-R alpha chain when it is complexed in the TSLP-Receptor (with CCRF2; Genbank accession Number AF338733; Reche et al., 2001). In particular embodiments, the antibodies provided herein bind to CD127 as an isolated protein with an affinity constant (KD) equal to or lower than 5E-9 M, as may be determined by biosensor analysis, in particular by Blitz method. In particular embodiments, the binding properties of the antibodies are determined or defined using an antigen of human CD127 comprising the sequences of epi (SEQ ID No: 19) and/or ep2 (SEQ ID No: 20). In particular embodiments, the antigen comprises a fragment of human CD127 comprising both epi and ep2 (i.e. the antigen comprises the sequences of ep 1 and ep2 and the intercalated sequences of human CD127). In particular embodiments, the antibodies provided herein have at least the same affinity to said antigen as the N13B2-h3 antibody disclosed in WO 2015/189302, and/or as the N13B2-hVL6 antibody disclosed herein (with the VH having the sequence of SEQ ID No: 7 and the VL having the sequence of SEQ ID No: 12) and/or as the antibody with the VH having the sequence of SEQ ID No: 7 and the VL with the sequence of SEQ ID No: 10 or with the sequence of SEQ ID No: 11.

Methods to test for the binding of the antibodies to their target, either full-length CD127, isolated or as the TSLPR or IL7R, or an antigen thereof as above, comprising in particular the Blitz method, are known to the skilled person and are illustrated in particular in 0, Example 3 and Example 4 herein and in p. 14, FIGS. 3, 4 and 6 and the respective legends, and Examples 1, 2, 6, 7 of WO 2015/189302.

Absence of Increased TSLP-Induced Dendritic Cell Maturation

The antibodies provided herein may bind CD127 in the TSLP receptor (i.e. may bind CD127 when it is in a complex with the CRLF2, forming the TSLP receptor). Therefore, the antibodies provided herein may interfere with TSLP-induced and/or TSLP receptor-mediated signaling. Preferably, the antibodies provided herein do not synergize with TSLP for the maturation of immune cells, in particular dendritic cells. In other words, the antibodies of the invention do not increase the maturation of immune cells induced by TSLP.

This effect is particularly desired on the maturation of dendritic cells. The means to measure such effect are known to the skilled person and are disclosed in particular in WO 2015/189302 at pages 16-17 and in Example 9 thereof. In particular, the antibodies provided herein do not increase expression of CD40 by more than 50% when compared to stimulation with TSLP alone (without antibody). Preferably, the expression of CD40 is not increased by more than 25%, preferably not by more than 10% and even more preferably not by more than 5%. In particularly preferred embodiments, the expression of CD40 is not increased or is decreased in cells stimulated with TSLP and with said antibodies when compared to cells stimulated with TSLP alone.

Inhibition of IL7-Induced Expression of α4, β17 and α4/β7 Integrins

In particular embodiments, the antibodies provided herein inhibit IL7-induced expression of α4, β7 and α4/β7 integrins in vitro. IL7-induced expression of α4, β7 and β4/β7 integrins, as used herein, designates either or both the increase in the level of expression of α4 and P7 integrins and the increase in the number or ratio of T lymphocytes expressing α4, β7 and/or α4/β7 integrins. The inhibition may be partial, i.e. the level of expression of α4, β7 and α4/β7 integrins in the presence of IL7 is increased over baseline level (i.e. the level with neither antibody nor IL7) in the presence of antibodies, but less than in the absence of antibodies; or the inhibition may be complete, i.e. the level of expression of α4, β7 and β4/β7 integrins in the presence of IL7 and of the antibody is no higher than baseline level.

In particular embodiments, the antibodies provided herein inhibit expression of α4, β7 and/or α4/β7 integrins in vitro, i.e. the level of expression of α4, β7 and/or β4/β7 integrins is lower in cells treated with antibodies (and with and/or without IL7) than in untreated cells (i.e. without antibody or IL7). The extent of inhibition may be dose-dependent. The inhibition of expression may be more specifically defined, tested and/or measured as set forth in WO 2015/189302 in p. 18, in particular paragraph [58], and in the Example 16.

Inhibitors of CD127 Internalization

In a particular embodiment, the antibodies provided herein inhibit the IL7-induced internalization of CD127. Thus, when incubated with said antibodies, the presence of IL7 induces no decrease in the cell surface expression of CD127, or induces a less strong decrease in the cell surface expression of CD127 than cells incubated without antibodies. In particular embodiments, when incubated with said antibodies, the level of CD127 cell surface expression when cells are incubated at 37° C. for 15 minutes with 5 ng/mL IL7 is at least 80%, preferably at least 90% of the cell surface expression level in cells incubated without IL7. In vitro, the cell surface expression is preferably measured after a limited time as indicated above. Besides, as most cellular internalization processes are inhibited at low temperature, the effect is usually best observed at physiological temperature, in particular 37° C. However, it is also contemplated to incubate cells at low temperature, in particular 4° C.

In a preferred embodiment, the antibodies provided herein do not induce the internalization of CD127. Thus, the cell surface expression of CD127 in cells incubated in the presence of said antibodies is not reduced, or is not significantly reduced, relative to cell surface expression in cells incubated in otherwise identical conditions, but in the absence of the antibody. In particular embodiments, when incubated at 37° C. for 30 to 45 minutes in the presence of 50 ng/mL of antibody, the level of CD127 cell surface expression is at least 80%, preferably at least 90% of its level in cells incubated in the absence of the antibody. This effect may be observed in the absence of IL7 (in both antibody-treated and -untreated cells), in the presence of IL7, and/or both.

The two CD127 internalization-related feature described above (i.e. inhibition of IL7-induced internalization or non-induction of internalization) may be further defined and/or tested as set forth in WO2015/189302 in particluar in paragraphs [59]-[63] at pages 19-20 and in FIG. 16 and Example 5.

Disruption of CD127-γc Chain Interaction

According to a particular embodiment, the antibodies provided herein may disrupt the binding of CD127 to the γc chain of the IL7-R. This means that, under conditions (in particular chemical and physical conditions) where CD127 and γc chain are bound together in the absence of antibody, and in particular in the presence of IL7, the presence of said antibodies significantly reduces said bond. In particular embodiments, in the presence of antibody and of IL7, CD127 does not bind to γc. In particular, in the presence of the antibody and of IL7, the amount of γc chain found associated with (or bound to) CD127 is less than 80%, preferably less than 50%, even more preferably less than 25% or 10% of the amount bound in the absence of the antibody (or in the presence of another anti CD-127 antibody such as MD707-13) in otherwise identical conditions, in particular in the presence of IL7. Such a feature of the antibody may be assessed in particular by co-immunoprecipitation methods, well known to the skilled person for testing the interaction of proteins and illustrated e.g. in WO2015/189302 in Example 21. In particular, cells may be incubated in the presence or absence of the tested antibody, then solubilized in conditions allowing for the preservation of protein complexes, and the resulting lysate may be subjected to an anti-CD127 immunoprecipitation and the presence of γc in the CD127-containing immunoprecipitated complex assessed by western blotting using anti-γe antibodies (conversely, the immunoprecipitation may be performed using anti-γe antibodies and the presence of CD127 assessed using anti-CD127 antibodies).

Antagonist Towards IL7-IL7-R Interaction

According to a particular embodiment, a macromolecule, in particular an antibody or antigen-binding fragment thereof, of the invention further has antagonist properties toward interleukin 7 (IL7) thereby antagonizing access, i.e. binding of IL7 to CD127 on CD127 positive cells.

"Antagonist properties towards IL7-IL7-R interaction" means that antibodies or antigen-binding fragments thereof of the invention, which target the IL7-Ralpha, have the effect of preventing the accessibility of the IL7 receptor expressed on CD127 cells, especially human effector T cells, in particular human memory T cells, for its binding partner IL7, especially human IL7. As a result of antagonizing binding of IL7, the antibodies of the invention or their functional fragments lead to lymphopenia by preventing IL7-dependent thymic T cells generation.

The antagonist properties may be in particular antagonism toward IL7-R signaling induced by IL7. An antagonist of IL7-R signaling induced by IL7 can be identified by measuring the inhibition of STAT5 phosphorylation as described in the Examples. The IL7-induced phosphorylation of STAT5 is a marker of IL7-R activation and an antibody antagonizing IL7-IL7-R interaction is expected to decrease IL7-induced phosphorylation of STAT5.

In particular embodiments, the macromolecule of the invention is an antagonist of IL7-R signaling induced by IL7. In a particular embodiment, the macromolecule of the invention inhibits IL7-induced phosphorylation of STAT5. In preferred embodiments, the inhibition of STAT5 phosphorylation is greater than 50% at antibody concentrations as low as 55 ng/ml and/or the inhibition of STAT5 phosphorylation is greater than 80% at antibody concentrations as low as 100 ng/ml. Inhibition of STAT5 phosphorylation may be assessed by methods known to the skilled person and in particular by the method set forth in the examples section, in particular in Example 5, and/or in page 21, paragraphs and and Example 3 of WO2015/189302.

Is is also desirable that the macromolecule of the invention (in particular antibody, antigen-binding fragment thereof or antibody mimetic molecule) inhibits the activation and/or does not activate or increase the activation, of the PI3-k and/or ERK (Extracellular signal-regulated kinase) signaling pathways and in particular inhibits the phosphorylation and/or does not induce or increase the phosphorylation of PI3-k and/or ERK 1 and/or ERK 2. In particular, the antibody, antigen-binding fragment thereof or antibody mimetic molecule provided herein, and in particular such antibody, antigen-binding fragment thereof or antibody mimetic molecule that is an antagonist towards IL-7-IL-7R interaction, does not induce the activation of the PI3-k and/or the ERK pathways (preferably of the PI3-k and the ERK pathway), and in particular does not induce the phosphorylation of PI3-k and/or of ERK 1 and/or ERK 2, more particularly does not induce the phosphorylation of PI3-k and of ERK 1 and of ERK 2. In particular, the antibody, antigen-binding fragment thereof or antibody mimetic molecule provided herein, and in particular such an antibody, antigen-binding fragment thereof or antibody mimetic molecule that is an antagonist towards IL-7-IL-7R interaction, inhibits the activation of the PI3-k and/or the ERK pathways, and in particular inhibits the phosphorylation of PI3-k and/or of ERK 1 and/or ERK 2, more particularly inhibits the phosphorylation of PI3-k and of ERK 1 and of ERK 2. The activation of the pathways and/or phosphorylation of said proteins, may be tested by methods known to the skilled person and in particular by Western blotting as illustrated in 0 and Example 8.

Antagonist for Binding of TSLP

Since the antibodies provided herein bind CD127 in the IL7-R, they may also bind CD127 in the TSLPR and, particularly by steric hindrance and/or by competition on common binding sites, they may inhibit the binding of TSLP to the TSLPR. In other words, the antibodies provided herein may present antagonist activity for the binding of TSLP.

Inhibitor of TSLP-Induced TARC Production

In a particular embodiment, the antibodies provided herein inhibit TSLP-induced TARC production of CD127-positive cells. As mentioned above, TSLP-stimulated dendritic cells produce elevated levels of TARC. This may result from their binding to the TSLPR and their potential action as antagonists of TSLP binding. In a particular embodiment, the antibodies provided herein do not increase the maturation of dendritic cells (maturation being e.g. determined an increased expression of CD40 and/or CD80 cell surface marker).

The level of TSLP-induced TARC production may be lower in cells treated with TSLP together with the anti-CD127 antibodies prvoided herein than in cells treated with TSLP alone. In other words, the antibodies prvoided herein may be inhibitors of TSLP-induced TARC production. In an embodiment of the invention, the antibodies prvoided herein decrease the levels of TARC production. In a particular embodiment, the level of TARC production in cells treated with TSLP and an antibody provided herein is reduced by more than 10%, preferably more than 20%, compared to the level in cells treated with TSLP alone, at antibody concentrations as low as 1 μg/ml. Measurement of TARC production can be carried out on CD127-positive immune cells, in particular dendritric cells, from a blood sample using any standard method known from the skilled person and is illustrated e.g. in WO2015/189302 in Example 9.

Cytotoxic Activity

In a particular embodiment, the antibodies provided herein are cytotoxic against human cells, especially human T cells expressing CD127. Human cells expressing CD127 as a chain of IL7 receptor, which are the target of said antibodies, are mainly T lymphocytes and more precisely are subpopulations of effector T lymphocytes including naïve and memory T cells but are not regulatory T cells (Treg), especially not resting natural Treg. Memory T cells are generated as a result of antigen priming and mainly defined by their functional characteristics, including ability to undergo recall proliferation upon re-activation and differentiation into secondary effector and memory cells. Similarly, the targeted TSLP receptor (as a complex including the IL-7-R alpha chain) regulates T helper lymphocyte, B cell and dendritic cell differentiation.

In particular, the antibodies provided herein, having "cytotoxic activity against T cells" or cytotoxic properties (cytotoxic antibodies) give rise to depletion in the effector T cell population by killing these cells and accordingly reduce the number of these cells when administered. Conversely, said antibodies do not alter the subpopulation of regulatory T cells or do not alter it to a significant extent, allowing the Treg cells to perform their function. In this context, in a particular embodiment, the ratio of regulatory T (Treg) versus effector T (Teff) cells raises following administration of said antibodies. In particular, the antibodies provided herein enable to raise said ratio of about 10% or more. In particular, the increase in the ratio of Treg versus Teff is of about 20%.

In particular, the cytotoxic antibodies show Antibody-Dependant Cellular Cytotoxicity (ADCC). Alternatively, the antibodies provided herein have no ADCC properties. Antibody ADCC potential may be considered positive when specific cytoxicity is e.g. superior to 10%. ADCC properties can be evaluated in an ADCC assay such as the test described in Example 10 of WO2015/189302. When the antibody is a rat antibody the effector cells used in the ADCC assay are preferably LAK (Lymphokine-activated killer) cells of rat. When the antibodies are humanized the ADCC assay can be carried out in particular on human NK cells.

The antibodies of the invention which have both cytotoxic and antagonist properties for CD127 positive cells enable cumulative effects of these properties with respect to the depletion of effector T cells, especially of memory T cells, thereby enabling a stronger depletion (exhaustion of the pool of CD127+ cells) and corresponding reduction in the number of target T cells.

The paragraphs above as well as the Examples describe how to test for the relevant desired functional characteristics of the antibodies provided herein. The following sections will detail various structural characteristics and possible modifications of the antibodies. In light of these guidances, the skilled person will be able to obtain antibodies having the structural characteristics below along with the desired functional characteristics, in particular starting from the N13B2-hVL6 antibody which has the desired functional characteristics.

When intended for administration to human subjects, it is desirable that antibodies present as strong as possible a homology with human antibodies, as the skilled person is aware. The degree of identity with a human antibody is measured as the % of human residues in the antibody sequence, in particular in the framework of the antibody light or heavy chain variable domain i.e. the % of residues in the antibody sequence, in particular in the framework of the antibody light or heavy chain variable domain, which are identical at the same fonctionnal position to the residue in the most homologous known human antibody, in particular in the framework of the most homologous known human antibody light or heavy chain variable domain. This feature is generaly expressed herein, as in the literature, as "antibody A (or the framework sequence of its variable domain) has xx % human residues", which means that antibody A (or the framework sequence of its variable domain) has xx % of residues which are identical at the same functional position to the residues of the most homologous known human antibody (or the framework sequence of its variable domain). Such degree of identity may be measured by means known to the skilled person and in particular with the International Immunogenetics Information System (IMGT) DomainGapAlign tool as clarified during open session of WHO INN Expert Group (April 2015). Preferably, the antibodies provided herein have more than 80%, even more preferably at least 84%, more than 84% and even more preferably at least 85% identity with a human antibody, in particular as determined using the DomainGapAlign tool. Said degree of identity may be determined for the light chain variable domain only or for light chain only (by comparison with a human antibody light chain variable domain or light chain) or for the light chain and the heavy chain taken together, by comparison of each chain with the most homologous corresponding human antibody chain, and reporting the cumulated percentage of identity. Particularly, the antibody light chain variable domain or the antibody light chain according to the invention comprises at least 80%, more particularly 84% and even more particularly at least 85% of human residues. The particular antibody light chain variable domains provided herein have respectively 84.2% (SEQ ID No: 9); 85.3% (SEQ ID No:10 and SEQ ID No:11) and 86.3% (SEQ ID No: 12) human residues. The preferred antibody heavy chain variable domain provided herein (SEQ ID No: 7) has 90.8% human residues.

An antibody light chain variable domain provided herein may comprise up to 135 amino acids, preferably up to 120 amino acids and even more preferably up to 110 or 107 amino acids. An antibody light chain variable domain provided herein may comprise at least 80, preferably at least 90 and even more preferably at least 100 or 106 amino acids. An antibody light chain variable domain provided herein may comprise 80 to 135, preferably 90 to 120 and even more preferably 105 to 110 amino acids.

An antibody light chain provided herein may comprise up to 250 amino acids, preferably up to 230 amino acids and even more preferably up to 214 or 211 amino acids. An antibody light chain provided herein may comprise at least 150, preferably at least 190 and even more preferably at least 200 or 210 amino acids. An antibody light chain provided herein may comprise 150 to 250, preferably 190 to 230 and even more preferably 210 to 220 amino acids.

Provided herein are also polypeptides which are (i) antigen-binding fragments of the antibodies provided herein, in particular antigen-binding fragments consisting or comprising a fragment of the antibody light chains or antibody light chain variable regions provided herein, an antibody heavy chain variable domain provided herein and/or (ii) antibody mimetic molecules of the antibodies provided herein.

An antigen-binding fragment is a polypeptide which binds specifically to the CD127 protein as defined above in the relevant section (paragraphs to [47]) and comprises at least the three CDRs of N13B2-h3 (consisting of the sequences of SEQ ID Nos:4 to 6), preferably a fragment of the light chain variable domains provided herein (with SEQ ID Nos: 9 to 12) comprising said CDR sequences. An antigen-binding fragment may comprise at least 40, preferably at least 50 and even more preferably at least 70 or 74 amino acids. An antibody-binding fragment may comprise at most 100, preferably at most 90 and even more preferably at most 80 or 74 amino acids. An antigen-binding fragment may comprise 40 to 100, 50 to 90 and preferably 60 to 100 and even more preferably 50 to 70 or 60 to 80 amino acids. An antigen-binding fragment as provided herein may in particular have any of the suitable functional features disclosed in respect to the antibodies provided herein, in particular the features disclosed in paragraphs to [62].

Accordingly, an isolated polypeptide provided herein may consist of a sequence of up to 250 amino acids, in particular of up to 217, of up to 214, of up to 211, more particularly of up to 200, of up to 175, of up to 150, of up to 135, of up to 120, of up to 107 and even more particularly of up to 100, of up to 90, of up to 80, of up to 74, of up to 70, of up to 60 amino acids.

An antibody mimetic molecule is a polypeptide with properties similar to an antibody, in particular with similar binding properties with CD127. Antibody mimetics may be, for examples, affibody molecules, affilins, affimers, anticalins, monobodies, etc. An antibody mimetic molecule as provided herein may in particular have any of the suitable functional features disclosed in respect to the antibodies provided herein, in particular the features disclosed in paragraphs to [62].

In particular, the antibody according to the invention is a humanized antibody, which comprises constant domains derived from human constant domains. In particular, the antibody light chain constant domain is derived from a human kappa light chain constant domain and/or the antibody heavy chain constant domain is derived from a human IgG1, IgG2, IgG3, or IgG4 heavy chain constant region, particularly from a human IgG4 heavy chain constant region. "Derived from" means some punctual mutations by amino acid substitutions such as IgG4 (S228P) or IgG1 (E333A). These mutations well known from the skilled person in the art, generally modify some parent chain properties. For example, they lead to less immunogenicity compared to the parental antibody or abrogate FcγReceptor binding or avoid dimerization of the monomer antibody or stabilize the dimerization rendering antibodies better for human therapeutical uses. The antibody of the invention derived from parental heavy and light chain constant domain comprises or consists of the sequence set forth in SEQ ID No: 26, SEQ ID No: 27 or in SEQ ID No: 28 or a fragment thereof, respectively. More particularly the antibody light chain constant domain consisting of the sequence set forth in SEQ ID No: 27. In particular, the antibody heavy chain constant domain comprises or consists of the sequence set forth in SEQ ID No: 26 or a fragment thereof. More particularly the antibody heavy chain constant domain consists of the sequence set forth in SEQ ID No: 26.

Provided herein are also isolated nucleic acid molecules encoding a polypeptide according to the invention, or an antibody or antigen-binding fragment thereof provided herein. Particularly, said nucleic acid molecules encode the light chain variable domain or the light chain of an antibody provided herein, in combination with isolated nucleic acid molecules encoding the heavy chain of an antibody provided herein, according to any of the definitions provided herein. In particular, provided herein is an isolated nucleic acid molecule encoding a polypeptide comprising or consisting of a sequence selected from the group consisting of SEQ ID No: 9; SEQ ID No: 10; SEQ ID No: 11; or SEQ ID No: 12. In particular, the isolated nucleic acid molecule according to the invention comprises or consists of a sequence selected from the group consisting of SEQ ID NO: 15, SEQ ID NO:16, SEQ ID NO:17 or SEQ ID NO:18. Particularly, said isolated nucleic acid molecule is provided in combination with an isolated nucleic acid molecule encoding a heavy chain comprising the three CDRs consisting of the sequences set forth in SEQ ID No: 1, SEQ ID No: 2, and SEQ ID No: 3, in particular encoding a heavy chain variable domain consisting of the sequence set forth in SEQ ID No: 7, more particularly the isolated nucleic acid molecule consisting of the sequence set forth in SEQ ID No: 13. In a preferred embodiment, a combination of isolated nucleic acid molecules encoding an antibody or antigen-binding fragment thereof is provided, said combination comprising or consisting of a first isolated nucleic acid molecule comprising or consisting of a sequence selected from the group consisting of SEQ ID No: 15, SEQ ID No: 16, SEQ ID No: 17 and SEQ ID No: 18; and a second isolated nucleic acid molecule comprising or consisting of the sequence of SEQ ID No: 13. In another preferred embodiment, a combination of isolated nucleic acid molecules encoding an antibody or antigen-binding fragment thereof is provided, said combination comprising or consisting of a first isolated nucleic acid molecule comprising or consisting of the sequence SEQ ID No: 18; and a second isolated nucleic acid molecule comprising or consisting of the sequence of SEQ ID No: 13.

Provided herein are also polynucleotides encoding the polypeptide sequence of a complete light chain, comprising both the variable and constant domain, i.e. in particular polynucleotides encoding of one of the sequences of SEQ ID No: 9 to 12 and the sequence of SEQ ID No:27 or 28, in particular polynucleotides comprising or consisting of one of the sequences SEQ ID No: 15 to 18 concatenated with SEQ ID No:30 or SEQ ID No:31. Such polynucleotides are provided in particular in combination with a polynucleotide encoding the polypeptide sequence of a complete heavy chain, comprising both the variable and constant domain, i.e. in particular polynucleotides encoding SEQ ID No: 7 and the sequence of SEQ ID No:26, in particular polynucleotides comprising or consisting of SEQ ID No: 13 concatenated with SEQ ID No:29.

In particular, the isolated nucleic acid molecules provided herein may advantageously comprise, besides a sequence encoding a light chain and optionally a heavy chain of an antibody provided herein, upstream from the sequence encoding said antibody chains, a sequence encoding a signal peptide allowing secretion of said chains when expressed in a production cell. They may also comprise one or more sequence(s) encoding one or more marker peptide(s) for detecting, and/or facilitating the purification of, said chains.

Provided herein is also a vector for the cloning and/or for the expression of a nucleic acid molecule provided herein. In particular, said provided vector is a plasmid suitable for cloning and/or expressing in mammalian cells, which comprises regulation sequences for transcription and expression. Accordingly, provided herein is a vector comprising a polynucleotide as disclosed above, in particular a polynucleotide as disclosed in paragraphs to [78].

Further, provided herein are cells or cell lines recombined with a nucleic acid molecule as above, in particular a vector, especially a mammalian or an avian cell or cell line, in particular as detailed in 0. For example Chinese Hamster Ovary Cells, genetically modified to reduce global fucosylation. Indeed, antibodies lacking core fucosylation show a significantly enhanced antibody-dependent cell-mediated cytotoxicity (ADCC) (von Horsten et al., 2010). Another example is the EB66 cell line which naturally has low fucosylation properties (Olivier et al., 2010). Antibodies may also be produced in cells transiently transfected with a nucleic acid molecule as above, in particular a vector, in particular COS cells, in particular as detailed in Example 2.

Provided herein are also methods for the production of a polypeptide provided herein, in particular an antibody light chain and/or a monoclonal antibody, said methods comprising the step of expressing said polypeptide, antibody light chain or monoclonal antibody (or the light and optionally the heavy chain of a monoclonal antibody) in cells comprising a nucleic acid molecule encoding said polypeptide, in conditions enabling the recovery of said polypeptide and the step of recovering said polypeptide. In particular, the antibodies or their fragment are prepared in cells that present low fucosylation properties, such as EB66 avian cells.

Provided herein is also a pharmaceutical composition comprising a polypeptide (in particular an antibody light chain variable domain or an antibody light chain) and/or an antibody or antigen-binding fragment or antibody mimetic molecule thereof and/or an isolated nucleic acid molecule as defined above, and a pharmaceutical vehicle. Said pharmaceutical composition can optionally further comprise a different active ingredient. Said composition is provided in particular in a formulation suitable for systemic administration, or for local administration. In particular, provided herein are compositions suitable for local administration, in particular for intramuscular or subcutaneous injection, for injection using a device such as an autoinjector (or injector pen), for transdermal administration, in particular using a transdermal patch, for transmucosal administration, in particular intranasal or rectal administration. In particular, provided herein are compositions suitable for local administration to the gastrointestinal (GI) tract, in particular through oral administration, in particular for the treatment of intestinal disease such as Crohn's disease or UC, in particular compositions suitable for delivery to the colon. In particular, provided herein are compositions suitable for systemic administration, in particular for parenteral or enteral administration, in particular for intravenous injection or oral administration. As the skilled person is aware, enteric administration may be either a local administration to the GI tract, or a systemic administration. Wherever such pharmaceutical compositions or their uses are provided herein, it must be understood that the administration vehicle and their uses may also be provided, e.g. when an injectable pharmaceutical composition is provided explicitly, it must be understood that the composition is provided as such as well as in a device or in combination with a device allowing administration and/or injection of said composition ("delivery device"). Examples of delivery devices include but are not limited to autoinjectors, in particular multichamber syringes, and transdermal patchs. Accordingly, provided herein are a delivery device, in particular an autoinjector, a pump, or a transdermal patch comprising said composition, and uses thereof as provided below in relation to the pharmaceutical compositions. Also provided herein are a kit comprising a pharmaceutical composition and a local delivery device, in particular a sub-cutaneous, enteric or oral delivery device, in particular a pre-filled syringe or a needle free device, containing said composition and/or suitable for the administration of said composition, and uses thereof as provided below in relation to the pharmaceutical compositions. The pharmaceutical composition is provided in any suitable form for administration, including as a solution, in particular a sterile aqueous solution, as a suspension, as a solid, in particular a lyophilized solid, in particular for adsorbtion on (or adsorbed on) a patch and/or for resuspension and administration as a solution, as a pill, tablet or other solid form suitable for oral administration, in particular with delayed or extended release, as nanoparticles, e.g. a composition comprising nanoparticles with the polypeptide adsorbed on the surface, or within said nanoparticles, etc. The form of the pharmaceutical composition and optionally the nature of the delivery device may be suitable for delivery of the active ingredient as provided herein systemically or locally, i.e. may be suitable for active ingredient to reach the targeted cells, tissues, organs, in an active state. Particularly, the form of the pharmaceutical composition and optionally the nature of the delivery device may be suitable for delivery to the GI tract, in particular to the colon. The pharmaceutical composition is said to comprise a pharmaceutically acceptable carrier; however, pharmaceutical compositions are also provided without a carrier for similar uses and purposes, when such a carrier is not required for pharmaceutical use, e.g. if the product is administered as a pure lyophilized solid. In particular, the administration is performed according to any suitable means as described herein for intenstinal release especially for intestinal delayed release.

Provided herein is also a composition comprising as an active ingredient, a polypeptide (in particular an antibody light chain variable domain or antibody light chain) and/or an antibody (in particular monoclonal antibody), antigen-binding fragment or antibody mimetic molecule thereof as defined above, or a pharmaceutical composition as defined above, in a formulation suitable for controlling human CD127 positive cells survival or expansion, in particular human CD127 positive effector cells, especially CD127+ memory T cells survival or expansion, especially memory T cells which are both CD127+ and CD8+, or which are both CD127+ and CD4+ cells, when administered to a human patient. In particular, said composition comprising the antibody (or other agent as above) as an active ingredient is in a formulation suitable for controlling the differentiation and/or maturation of dendritic cells when administered to a patient.

The inventors have surprisingly shown that a single injection of the antibody provided herein allows for sustained effect, and the inflammatory response is still significantly reduced in animals treated by a single injection of the provided antibodies as long as 14 months, and even as long as 18 months following said single injection. The administration, and preferably a single administration, of the polypeptide, in particular antibody light chain and more particularly the antibody, antigen-binding fragment or antibody mimetic molecule thereof provided herein, preferably has a fast and/or a long-lasting effect on effector memory T cells. A fast effect is observed preferably within a week, and more preferably within 48 hours, and even more preferably within a day of the administration of said polypeptide, antibody chain or antibody. A long-lasting effect is observed preferably at least 12 months, and more preferably at least 14 months after the most recent (and, preferably, the single) administration of said polypeptide, antibody chain or antibody. Such an effet is in particular reversible (in particular T cell response may be restored by new vaccination). Such an effect is preferably antigen and/or response-specific and is preferably not associated with measurable lymphodepletion (i.e. the global number of lymphocytes is not reduced in the subject, as measurey by common methods). Such an effect may otherwise be defined as a clonal deletion of memory T cells, or as a reversible, antigen specific deletion of immune T memory. An effect of such adminsitration on effector memory T cells may be assessed by comparing levels of IFN-γ secreting cells (measured e.g. by ELISPOT) in response to an antigen, e.g. tuberculine, in vaccinated subjects (in particular in baboons) which were later treated with the polypeptide, antibody chain or monoclonal antibody provided herein, and in untreated vaccinated subjects: an effect is observed if the measured level of antigen-specific T cells is significantly lower (preferably at least 10%, more preferably at least 40% lower) in the treated subjects, at the relevant time point after treatment. Such an effect may also be measured by otherwise assessing inflammatory response to a given antigen, e.g. a local, in particular dermal, inflammatory reaction in response to an locally administered antigen. Alternatively, an MHC tetramer assay may be used. Methods to test for such effect are known to the skilled person and are illustrated herein in particular in Example 6.

In addition, the inventors have surprisingly shown that the antibody provided herein may have a fast effect, in particular on T-cell activation, in particular on release of cytokines by T-cells, in particular in inflammatory tissue. Such an effect is in particular observed within a week, and preferably within 48 and even more preferably within 24 hours of administration of the antibody, and in particular is observed as a reduction in the IFNγ production (or release). Such effect is in particular observed locally, i.e. at the site of administration of the antibody or at the site of delivery. In particular, the antibody provided herein has a fast effect, in particular a fast local effect, in particular on release of cytokines by T-cells, in particular has an effect observed within 24 hours of administration. When the antibody is administered for local delivery but not directly at the site of intended delivery, the antibody may have fast effect as above at the site of delivery, within the same time periods from delivery rather than from administration, which may or may not be delayed from administration as the skilled person is aware.

A composition provided herein may further comprise an additional compound having a therapeutic immunomodulator effect, in particular on cells involved in allergy or autoimmunity. For illustration purposes, exemplary immunomodulators of interest or other monoclonal antibodies targeting T cells, such as anti-CD3, anti-ICOS or anti-CD28 antibodies or recombinant proteins or antibodies targeting accessory cells such as CTLA4Ig or anti-CD40 antibodies.

The polypeptide, antibody, antigen-binding fragment or antibody mimetic molecule thereof, isolated nucleic acid molecule, cell and/or composition provided herein may be provided in a combination product, comprising additional products, in particular an agent with a therapeutic immunomodulator effect as above, in particular intended for simultaneously separately or sequentially administration. Provided herein is a combination product comprising a polypeptide (in particular an antibody light chain variable domain or antibody light chain) and/or an antibody, antigen-binding fragment or antibody mimetic molecule thereof, and/or an isolated nucleic acid molecule, vector, cell or cell line, and/or a pharmaceutical composition as defined above and optionally further comprising:

an agent with a therapeutic immunomodulator effect, in particular intended for administration in combination with e.g. the antibody provided herein, in particular wherein said administration is either simultaneous or separated in time, and/or wherein said administration is through the same or a different route; and/or a device for administration of the product.

A polypeptide, in particular an antibody light chain and/or an antibody, in particular a monoclonal antibody and/or an antigen-binding fragment or antibody mimetic molecule and/or a nucleic acid, vector, cell or cell line and/or a pharmaceutical composition or a composition as defined above are in particular provided for use in a human patient for treating pathologies or pathologic conditions pathologic conditions influenced by immune responses, especially by memory T cells responses. Such conditions or pathologies comprise those induced by transplant rejection, autoimmune diseases, allergic diseases, respiratory diseases, chronic viral infections, chronic inflammatory disease, in particular chronic intestinal inflammatory disease, lymphoma, leukemia or other cancer diseases including those resulting from solid tumors when these pathologies are associated with CD127 positive cells as well as the IL-7 signaling pathway, in particular where an increase in the maturation of dendritic cells must be avoided. Accordingly, the inventors show that the use of said agents may be contemplated for the treatment of particular allergic skin disorders, inflammatory bowel disease (IBD), in particular Crohn's disease (CD) or ulcerative colitis (UC), or Primary Sjögren Syndrome, or Systemic Lupus Erythematosus, or Systemic Sclerosis or multiple sclerosis, or type I diabetes or acute lymphoblastic leukemia (e.g. T-ALL) or Hodgkin lymphoma, or breast cancer associated with CD127+ cells, renal cancer, bladder cancer, lung cancer, pancreatic cancer, or for the treatment of a T cell cutaneous lymphoma, such as Sezary lymphoma, or for the treatment of the acute lymphoblastoid leukemia with gain-of-function mutation of the IL-7-R/TSLP pathway or for the treatment of transplant rejection and/or of patients in need of transplantation and/or about to undergo transplantation and/or in having undergone transplantion. The treatment of inflammatory bowel disease (IBD), in particular Crohn's disease (CD) or ulcerative colitis (UC), or Primary Sjögren Syndrome, or Systemic Lupus Erythematosus, or Systemic Sclerosis or multiple sclerosis, or type I diabetes is contemplated in preferred embodiments. In particular, the invention relates to the polypeptide, or the antibody or antigen-binding fragment or antibody mimetic molecule thereof, or the isolated nucleic acid molecule, or the pharmaceutical composition according to the invention for use as a medicament, more particularly for use in the prevention or treatment of organ or tissue transplant rejection or of a disease selected from the group consisting of autoimmune diseases, particularly rheumatoid arthritis, systemic sclerosis, multiple sclerosis, type I diabetes, autoimmune thyroiditis, systemic lupus erythematosus, primary sjögren syndrome, and inflammatory diseases, particularly inflammatory bowel disease (IBD), more particularly Crohn's disease and ulcerative colitis and encephalomyelitis and allergic diseases and cancer diseases and diseases related to transplantation and respiratory diseases, preferably by local administration.

Provided herein are uses of the polypeptide, antibody light chain or antibody, antigen-binding fragment or antibody mimetic molecule thereof in the treatment of pathologic conditions involving the alteration of immune response in a human patient leading to dominant tolerogenic state or, to the contrary, lack of tolerance where control of the level of the immune response would be needed as well as destruction of malignant CD127-positive cells.

By "treatment" or "therapeutic treatment", it is meant that the performed steps of administration result in improving the clinical condition of an animal or a human patient in need thereof, who suffers from disorder(s) associated with the IL-7 pathway, i.e. involving the activation or proliferation of CD127 positive cells. Such treatment aims at improving the clinical status of the animal or human patient, by eliminating or alleviating the symptoms associated with the disorder(s) related to the IL-7 pathway, i.e. involving the activation or proliferation of CD127 positive cells. Preferabaly, the treatment provided herein enables restoring to health. Preferably, said treatment does not have undesired negative effects due to increased maturation of immune cells, in particular of dendritic cells.

In particular aspects of the treatment of patients, the polyeptide, antibody, antigen-binding fragment, antibody mimetic molecule, polynucleotide, cell or cell line, or composition is provided, intended and/or suitable for use to deplete CD127-positive cells while preserving CD127-negative cells.

In particular aspects of the treatment of patients, the use of the polypeptide, antibody, antigen-binding fragment, antibody mimetic molecule, polynucleotide, cell or cell line, or composition is provided, intended and/or suitable for use to prevent differentiation and/or expansion and/or maturation of CD127-positive cells, in particular differentiation, expansion, or maturation induced by IL-7 and/or TSLP, while having little or no direct effect on CD127-negative cells.

In particular aspects of the treatment of patients, the use of the polypeptide, antibody, antigen-binding fragment, antibody mimetic molecule, polynucleotide, cell or cell line, or composition is provided, intended and/or suitable for use to eliminate/neutralize naïve and memory T cells by interfering with IL-7-induced signaling, while preserving Treg cells.

In particular aspects of the treatment of patients, the use of the polypeptide, antibody, antigen-binding fragment, antibody mimetic molecule, polynucleotide, cell or cell line, or composition is provided, intended and/or suitable for use to deplete subpopulations of lymphocytes, or other cell populations expressing CD127 (including normal or pathologic T and B lymphocytes, NK cells, dendritic cells and other cell types including epithelial cells) as a result of cytotoxic action of the antibodies, possibly but not exclusively through ADCC (Antibody-Dependent Cellular Cytotoxicity) and optionally through CDC (Complement-Dependent Cytotoxicity).

Also provided herein is a polypeptide, in particular an antibody light chain and/or an antibody, antigen-binding fragment, antibody mimetic molecule, polynucleotide, cell or cell line, or composition as defined above, for use as active ingredient in a combination or add-on therapeutic regimen in a patient in need thereof. Also provided is the use of a polypeptide, in particular an antibody light chain and/or an antibody, antigen-binding fragment, antibody mimetic molecule, polynucleotide, cell or cell line, or composition as defined above as a therapeutically active ingredient in a combination or in an add-on therapeutic regimen in a patient in need thereof.

In the aspects above, the contemplated uses are also applicable to nucleic acids, vectors, cells, cell lines, compositions and pharmaceutical compositions provided hereinabove.

Provided herein are the means and products above intended and/or suitable for use in pathologies such as those induced by transplant rejection, autoimmune diseases, allergic diseases, respiratory diseases, chronic viral infections, chronic inflammatory disease, in particular chronic intestinal inflammatory disease, lymphoma, leukemia or other cancer diseases including those resulting from solid tumors when these pathologies are associated with CD127 positive cells as well as the IL-7 signaling pathway, in particular where an increase in the maturation of dendritic cells must be avoided. Accordingly, said means and products are particularly intended and/or suitable for the treatment of particular allergic skin disorders, inflammatory bowel disease (IBD), in particular Crohn's disease (CD) or ulcerative colitis (UC), or acute lymphoblastic leukemia (e.g. T-ALL) or Hodgkin lymphoma, or breast cancer associated with CD127+ cells, renal cancer, bladder cancer, lung cancer, pancreatic cancer, or for the treatment of a T cell cutaneous lymphoma, such as Sezary lymphoma, or for the treatment of the acute lymphoblastoid leukemia with gain-of-function mutation of the IL-7-R/TSLP pathway or for the treatment of transplant rejection and/or of patients in need of transplantation and/or about to undergo transplantation and/or in having undergone transplantion.

In particular, provided herein are the use of a polypeptide, in particular an antibody light chain and/or an antibody, antigen-binding fragment, antibody mimetic molecule, a nucleic acid, cell, cell line or composition in a human patient for the treatment of conditions and/or pathologies induced by transplant rejection, autoimmune diseases, allergic diseases, respiratory diseases, chronic viral infections, chronic inflammatory disease, in particular chronic intestinal inflammatory disease, lymphoma, leukemia or other cancer diseases including those resulting from solid tumors when these pathologies are associated with CD127 positive cells as well as the IL7 signaling pathway, in particular where an increase in the maturation of dendritic cells must be avoided. Accordingly, said products are particularly for the treatment of particular allergic skin disorders, inflammatory bowel disease (IBD), in particular Crohn's disease (CD) or ulcerative colitis (UC), or acute lymphoblastic leukemia (e.g. T-ALL) or Hodgkin lymphoma, or breast cancer associated with CD127+ cells, renal cancer, bladder cancer, lung cancer, pancreatic cancer, or for the treatment of a T cell cutaneous lymphoma, such as Sezary lymphoma, or for the treatment of the acute lymphoblastoid leukemia with gain-of-function mutation of the IL7-R/TSLP pathway or for the treatment of transplant rejection and/or of patients in need of transplantation and/or about to undergo transplantation and/or in having undergone transplantation autoimmune disease or an allergic disease or for the treatment of leukemia such as acute lymphoblastic leukemia or for the treatment of lymphoma, or for the treatment of cancer disease, or for the treatment of a chronic viral infection, or for the treatment of inflammatory diseases, in particular IBD, particularly CD or UC, or for the treatment of respiratory diseases, or for the prevention and/or treatment of symptoms related to a transplantation.

In particular, provided herein is a method of treatment comprising the administration of a polypeptide (in particular an antibody light chain variable domain or an antibody light chain) and/or an antibody, antigen-binding fragment, antibody mimetic molecule, or an isolated nucleic acid molecule, cell, and/or cell line or a composition and/or pharmaceutical composition as defined above in a human patient for the treatment of conditions and/or pathologies induced by transplant rejection, autoimmune diseases, allergic diseases, respiratory diseases, chronic viral infections, chronic inflammatory disease, in particular chronic intestinal inflammatory disease, lymphoma, leukemia or other cancer diseases including those resulting from solid tumors when these pathologies are associated with CD127 positive cells as well as the IL-7 signaling pathway, in particular where an increase in the maturation of dendritic cells must be avoided. Accordingly, said methods are particularly for the treatment of particular allergic skin disorders, inflammatory bowel disease (IBD), in particular Crohn's disease (CD) or ulcerative colitis (UC), or acute lymphoblastic leukemia (e.g. T-ALL) or Hodgkin lymphoma, or breast cancer associated with CD127+ cells, renal cancer, bladder cancer, lung cancer, pancreatic cancer, or for the treatment of a T cell cutaneous lymphoma, such as Sezary lymphoma, or for the treatment of the acute lymphoblastoid leukemia with gain-of-function mutation of the IL7-R/TSLP pathway or for the treatment of transplant rejection and/or of patients in need of transplantation and/or about to undergo transplantation and/ or in having undergone transplantionan autoimmune disease or an allergic disease or for the treatment of leukemia such as acute lymphoblastic leukemia or for the treatment of lymphoma, or for the treatment of cancer disease, or for the treatment of a chronic viral infection, or for the treatment of inflammatory diseases, in particular IBD, particularly CD or UC, or for the treatment of respiratory diseases, or for the prevention and/or treatment of symptoms related to a transplantation.

The inventors have further shown that in patients with UC, levels of IL7, CD127 and/or TSLPR mRNA allow to predict response to conventional immunosuppressive treatments: responders (i.e. patients which exhibit marked symptom reduction in response to treatment) have lower levels of IL-7 and CD127 and higher levels of TLSPR than non-responders. Accordingly, provided herein are in vivo methods to assess the likelihood of response to immunosuppressive treatments in patients, in particular human patients, having ulcerative colitis (UC) comprising measuring in a sample obtained from said patient the level of IL7, CD127 and/or TLSPR mRNA or protein, and concluding that the likelihood of response is increased compared to a reference group when the measured level of IL7 and/or CD127 is lower than the average level in said group and/or when the measured level of TSLPR is higher than the average level in said group. Methods to perform the required measurements are known to the skilled person and may involve the use of an antibody against CD127 in particular for the measurement of the protein expression levels of CD127. The polypeptide, particularly the antibody light chain and/or the monoclonal antibody provided hereinabove is provided in particular for use in such methods and such methods are provided in particular using such a polypeptide, antibody light chain and/or the monoclonal antibody.

In particular, provided herein is a method of selecting a compound from the group consisting of an antibody, an antigen-binding fragment thereof and an antibody mimetic molecule, the method comprising at least one of the following steps:

i. testing the binding of the compound to CD127, in particular to human CD127, in particular to an epitope sequence from domain D1 and/or from the site 2b of domain D2 of CD127. An epitope sequence from domain D1 and/or from the site 2b of domain D2 may be any one of the epitope sequences described therein, particularly as disclosed in paragraphs [016], particularly an epitope sequence selected from the group consisting of SEQ ID No: 32, SEQ ID No: 33, SEQ ID No: 34, SEQ ID No: 35, SEQ ID No: 36 or SEQ ID No: 96, and more particularly SEQ ID No: 34, SEQ ID No: 35 and SEQ ID No: 96. In a particular embodiment of the invention, the binding test may encompass testing the binding of the compound to an epitope sequence selected from the group consisting of SEQ ID No: 34, SEQ ID No: 35 and SEQ ID No: 96, and testing the binding of the compound to an epitope sequence selected from the group consisting of SEQ ID No: 42 and SEQ ID No: 43. The binding capacity of the compound may be tested by any one of the methods know in the art, in particular the Blitz method, known to the skilled person and illustrated in particular in 0, Example 3 and Example 4 herein and in p. 14, FIGS. 3, 4 and 6 and the respective legends, and Examples 1, 2, 6, 7 of WO 2015/189302, and/or by the method of example 10 disclosed herein; and/or ii. testing the inhibition of IL7-R signaling induced by IL-7, in particular STAT5 phosphorylation, in presence of the compound. The inhibition induced by IL7 in presence of the compound may be tested by the method disclosed in example 8 and/or example 11 herein; and/or iii. testing the activation of the phosphatidylinositol 3-kinase in presence of the compound. The activation of the phosphatidylinositol 3-kinase in presence of the compound may be tested according to the method disclosed in example 8 and/or example 11 herein; and/or iv. testing the activation of the ERK signaling pathway in presence of the compound. The activation of the ERK signaling pathway in presence of the compound may be tested according to the method disclosed in example 8 and/or example 11 herein;

v. testing the binding capacity of the compound to at least one beta sheet of the site 2b of domain D2 of CD127, in particular at least to the third beta sheet of site 2b, defined as being the nucleo acids of SEQ ID No: 34, and/or to at least one amino acid sequence selected from the group of SEQ ID No: 35 and SEQ ID No: 96. The binding capacity of the compound may be tested by any one of the methods know in the art, in particular the Blitz method, known to the skilled person and illustrated in particular in 0, Example 3 and Example 4 herein and in p. 14, FIGS. 3, 4 and 6 and the respective legends, and Examples 1, 2, 6, 7 of WO 2015/189302, and/or by the method of example 10 disclosed herein.

The method may further comprise any one of the following optional steps, or at least one of the following optional steps:

vi. testing the binding of CD127, in particular human CD127, to the γc common chain of cytokine receptors in the presence of the compound. The binding of CD127 to the γc common chain of cytokine receptors in the presence of the compound may be assessed in particular by co-immunoprecipitation methods, well known to the skilled person for testing the interaction of proteins and illustrated e.g. in WO2015/189302 in Example 21. In particular, cells may be incubated in the presence or absence of the tested compound, then solubilized in conditions allowing for the preservation of protein complexes, and the resulting lysate may be subjected to an anti-CD127 immunoprecipitation and the presence of γc in the CD127-containing immunoprecipitated complex assessed by western blotting using anti-γc antibodies (conversely, the immunoprecipitation may be performed using anti-γc antibodies and the presence of CD127 assessed using anti-CD127 antibodies); and/or vii. testing the internalization of CD127, in particular human CD127, and/or IL7-induced internalization of CD127 in presence of the compound. The internalization of CD127, herein defined in paragraphs to [53], may be further defined and/or tested as set forth in WO2015/189302 in particluar in paragraphs [59]-[63] at pages 19-20 and in FIG. 16 and example 5; and/or viii. testing the maturation of dendritic cells induced by TSLP in presence of the compound. The maturation of dentritic cells induced by TSLP is defined in paragraphs and herein. The means to measure such effect are known to the skilled person and are disclosed in particular in WO 2015/189302 at pages 16-17 and in Example 9 thereof. In particular, the means to measure such effect comprise measure of the expression of CD40 between cells stimulated with the compound and cells stimulated with TSLP alone (without the compound).

In a particular embodiment of the method, the compound which specifically binds to CD127, in particular human CD127, which is an antagonist of IL7-R signalling induced by IL7, which does not induce the activation of the phosphatidylinositol 3-kinase and/or the ERK signaling pathway is selected. In a more particular embodiment of the method, the compound which specifically bind to CD127, in particular human CD127, which is an antagonist of IL7-R signaling induced by IL7, and which does not induce the activation of the phosphatidylinositol 3-kinase and does not induce the activation of the ERK signaling pathway is selected.

In particular, provided herein is a method for producing an antibody or an antigen-binding fragment thereof of the invention, which is raised against CD127, possibly raised from an immunization of a non-human animal, such as rats of the LOU/C Igk1a strain available at the university of Louvain, Belgium). Immunization can be carried out using a fragment of the amino acid sequence of SEQ ID No: 22, and in particular a fragment of SEQ ID No: 22 comprising an epitope sequence as defined herein, and in particular SEQ ID No: 35 and/or SEQ ID No: 96, as an immunogen. Hybridoma may be obtained by fusing spleen mononuclear cells with the LOU rat immunocytoma IR983F. Hybridoma may be screened according to the capacity of the secreted monoclonal antibodies to bind to an amino acid sequence selected from the group consisting of SEQ ID No: 22, SEQ ID No: 35 and SEQ ID No: 96, in particular SEQ ID No: 35 and/or SEQ ID No: 96. Therefore, the invention also encompasses an immunogen compound, said immunogen compound being a fragment of the amino acid sequence of SEQ ID No: 22, in particular a fragment comprising at least one amino acid sequence selected from the group of SEQ ID No: 32, SEQ ID No: 33, SEQ ID No: 34, SEQ ID No: 35 and SEQ ID No: 96, in particular SEQ No: 34, SEQ ID No: 35 and SEQ ID No: 96, more particularly SEQ ID No: 96. In a particular embodiment of the invention, the immunogen compound is a linear peptide, in particular a linear peptide comprising the amino acid sequence of SEQ ID No: 96, more particularly, a linear peptide comprising or consisting of, preferably consiting of, the amino acid sequence of SEQ ID No: 35.

BRIEF DESCRIPTION OF THE DRAWINGS

FIG. 1A,B. Amino Acid Sequences of the Antibodies Provided Herein

Panel A. Sequence of the heavy chain (VH). The CDRs are in bold characters.

Panel B. Sequence of the humanized light chains (LH) derived from N13B2. The CDRs are in bold characters. N13B2-VL3 comprises original framework residues of N13B2-h3 in positions 48 and 87 (underlined); N13B2-VL4-V48L and N13B2-VL5-F87Y comprise the corresponding humanized framework residue and N13B2-VL6-V48L-F87Y comprises both humanized framework residues.

Figure 2:
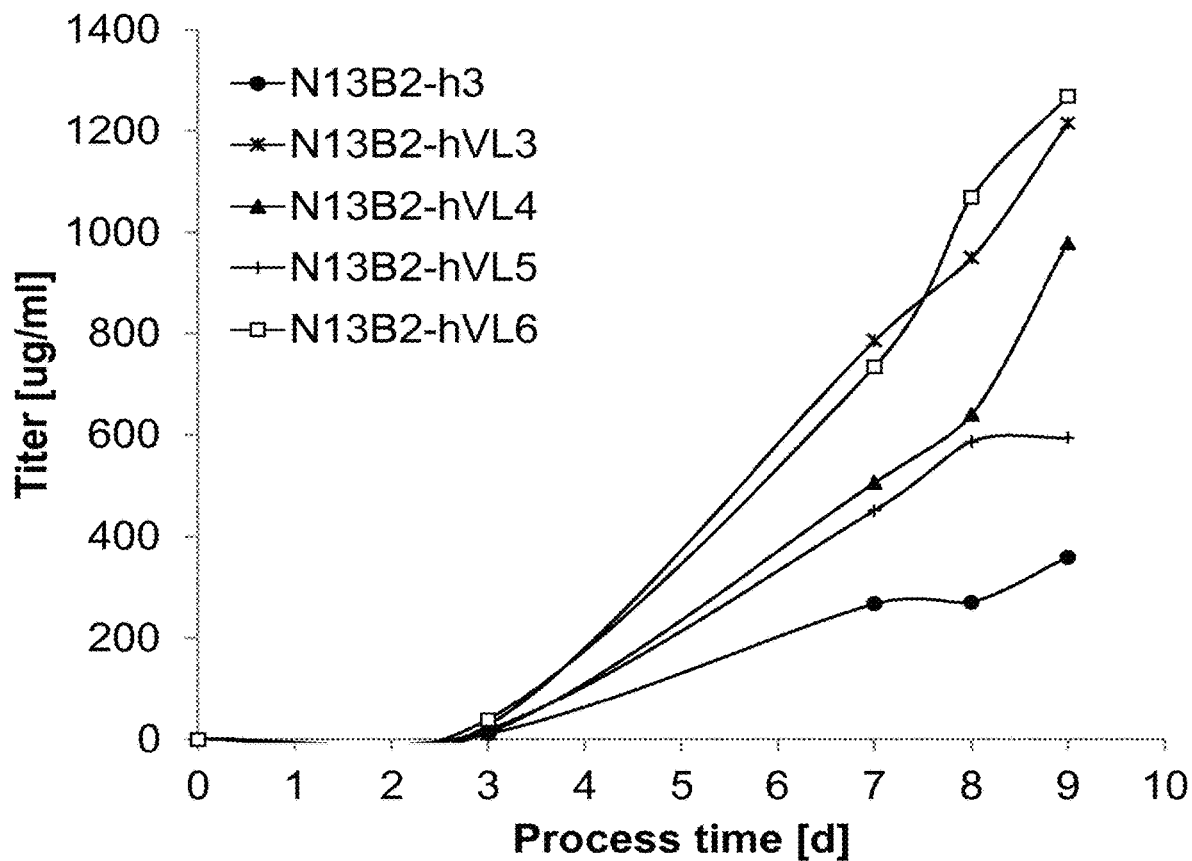

FIG. 2. Production of Antibodies—Stable Transfection

Three different production batches were performed for each of the mentioned antibodies in CHO-M cells according common methods, using commercially available serum-free media, and titers obtained in typical experiments, measured by an ELISA assay, are reported here. The horizontal axis represents the culture time, in days, while the vertical axis represents the obtained antibody titers, in µg/mL.

Figure 3:
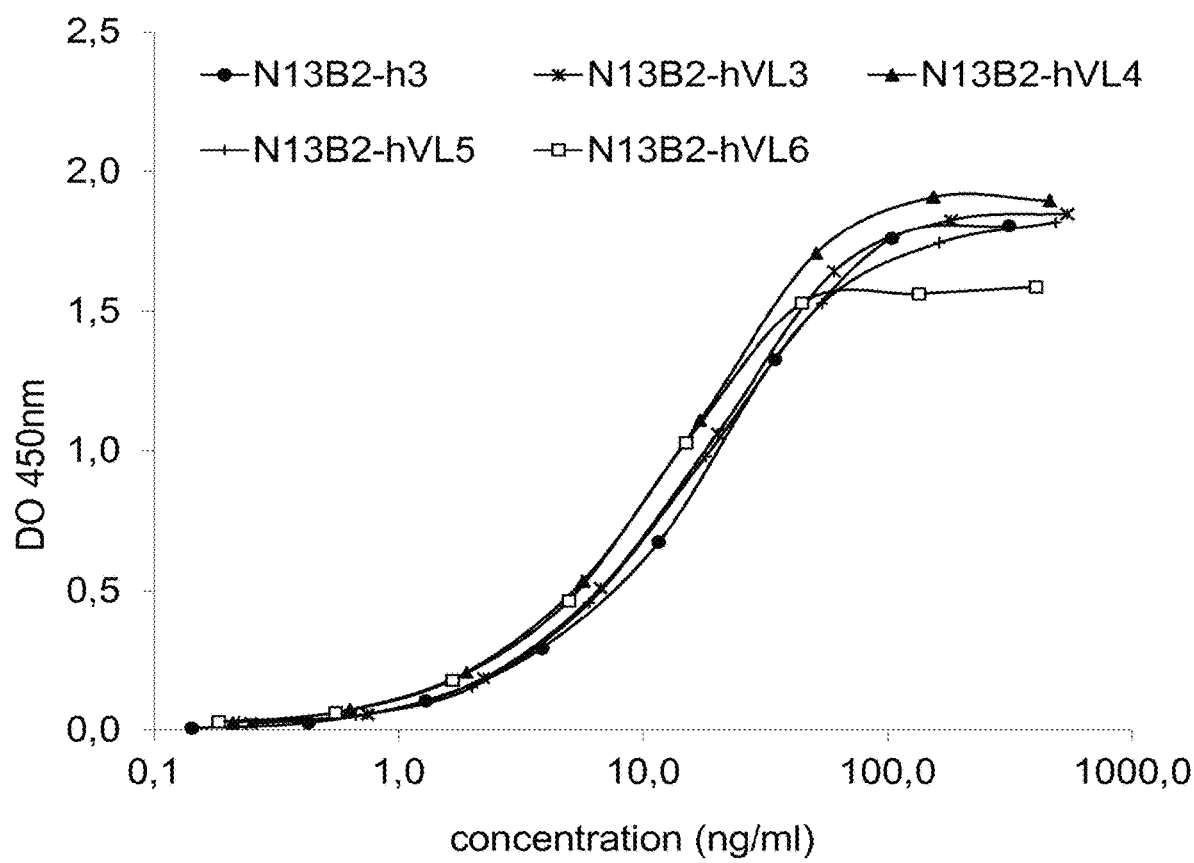

FIG. 3. Binding to CD127

Binding of the indicated antibodies to recombinant CD127 was assayed by ELISA according to the method detailed in Example 3. The horizontal axis represents antibody concentration in ng/mL, and the vertical axis represents optical density at 450 nm, in arbitrary units.

FIG. 4A,B. Inhibition of STAT5 Phosphorylation

The inhibition of STAT5 phosphorylation by the indicated antibodies was assayed by cytofluorometry according to the method detailed in Example 5. The percentage of CD3+ cells stained with pSTAT5 antibodies is reported in panel A (horizontal axis: antibody concentration in ng/mL) and the mean fluorescence intensity (in arbitrary units) of pSTAT5 signal for CD3+ cells is reported in panel B.

FIG. 5A,B. Effect on Memory T Cells

Panel A. DTH response (Area under curve of erythema curves) in baboon after N13B2 injection.

Delayed-type hypersensitivity in response to a tuberculin challenge was assayed in vaccinated baboons, after administration of N13B2 (n=7 baboons) or excipient (n=4 baboons), by measuring dermal reaction according to the method detailed in Example 6. The vertical axis represents area under the erythema curve, in arbitrary units. Values are reported for intradermal reactions performed at the given time points, indicated in days on the horizontal axis, before or after the administration of N13B2 or excipient (administered at day 0). "Post-BCG" corresponds to dermal reaction results performed after a new vaccination with BCG (nd=not determined).

The excipient control was not determined at days 150 and 180 and "post-BCG" (nd).

Panel B.

DTH response (Area under curve of erythema curves) in baboon after humanized N13B2 injection.

Delayed-type hypersensitiviy in response to a tuberculin challenge was assayed in vaccinated baboons, after administration of humanized N13B2 (AA892BB, 32257, V915GQ, 33874) or buffer, by measuring dermal reaction according to the method detailed in Example 6. The vertical axis represents area under the erythema curve, in arbitrary units. Values are reported for intradermal reactions performed before the administration of humanized N13B2 or buffer ("IDR1", first bar from left for each baboon), 4 hours after administration of humanized N13B2 or buffer ("IDR2", second bar from left), one, two and three months ("IDR3-5", third to fifth bar from left) and four months ("IDR6", sixth bar from left, for V915GA only) after administration of humanized N13B2 or buffer and after a new vaccination with BCG ("IDR7", last bar from left).

Panel C.

IFNγ ELISPOT performed on blood PBMC in BCG-vaccinated baboon challenged with tuberculin and treated with humanized N13B2.

AG-specific T cell frequency after tuberculin challenge was assayed in vaccinated baboons after administration of humanized N13B2 (AA892BB, 32257, V915GQ, 33874) or buffer, by IFNγ ELISPOT assay according to the method detailed in Example 6. The vertical axis represents spot frequency for 100.000 cells. Values are reported for Elispot without antigen (W/o Ag, left bars) or with tuberculin antigen (right bars) performed before the administration of humanized N13B2 or buffer (first bar from left for each group of bars), 4 days after administration of humanized N13B2 or buffer ("IDR2"), one, two and three months ("IDR3-5") and four months ("IDR6", for V915GA only) after administration of humanized N13B2 or buffer and after a new vaccination with BCG (last bar from left, dashed).

Figure 6:
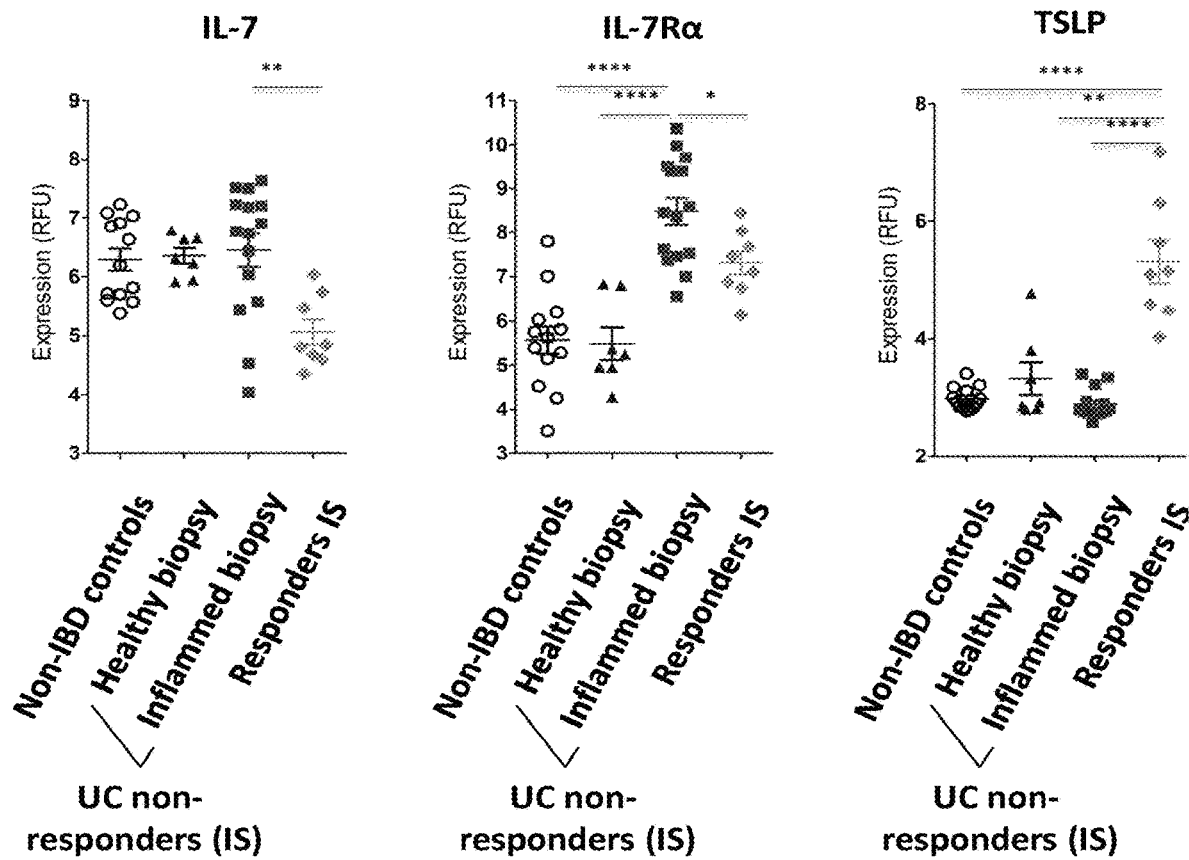

FIG. 6. Expression of IL-7, CD127 and TSLP in IBD Patients mRNA expression levels of IL-7, CD127 (soluble form of IL-7Rα) and TSLP (full-length) were measured according to the method detailed in Example 7 in tissue samples from healthy control subjects (Non-IBD control), healthy and diseased (inflammed) colon biopsy samples from patients with active ulcerative colitis (UC) who did not respond (or no longer responded) to antiinflammatory treatment and in samples from UC patients with quiescent disease—i.e. were cured or in remission at the time of sampling (Responders). The vertical axis represents relative fluorescence units. The value is plotted for each sample in a given group, the horizontal bar representing the average values for the group and the error bars represent the standard deviation. "*" denotes a p-value<0.05; ""a p-value<0.01; "**" a p-value<0.0001.

Figure 7:
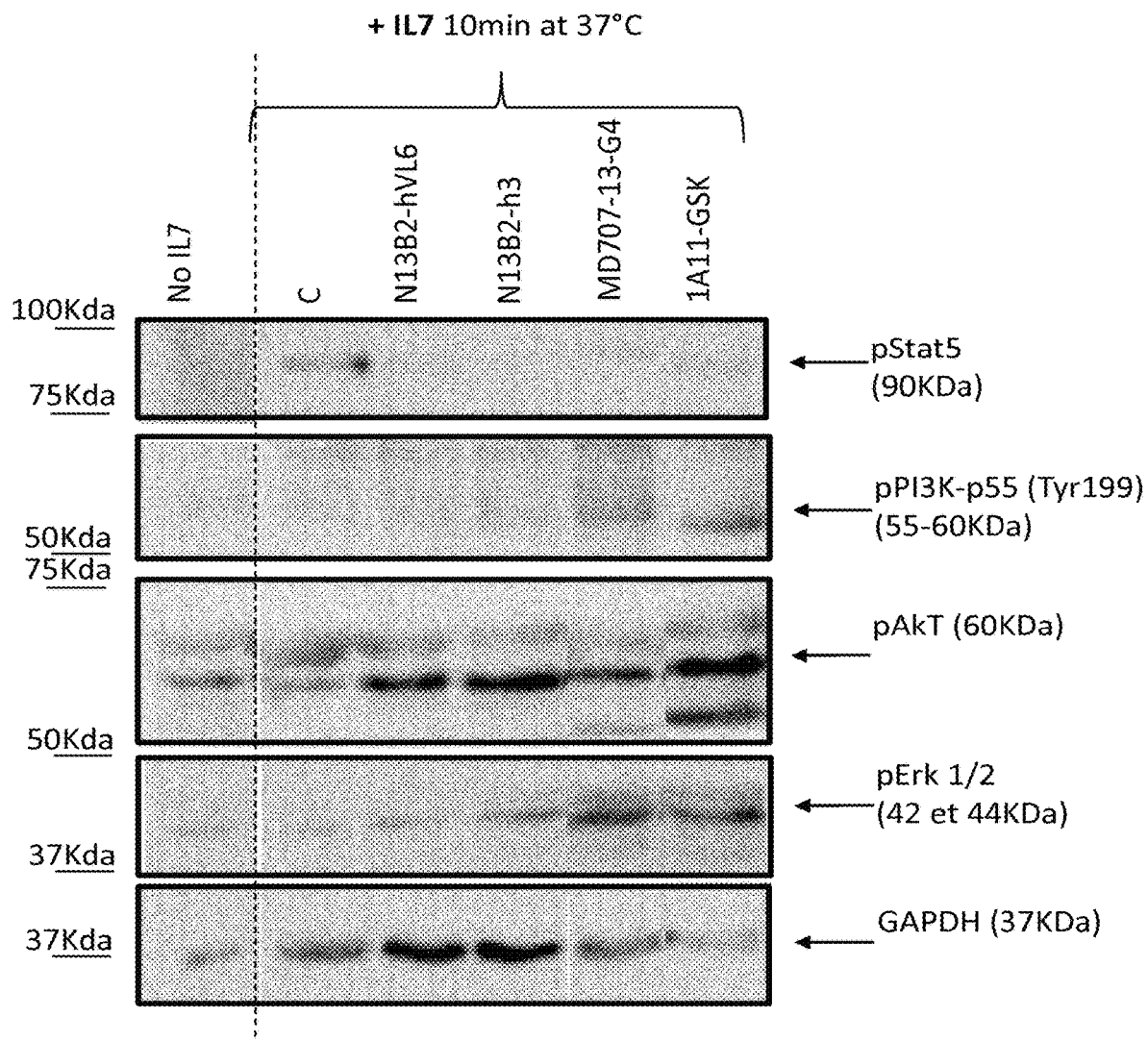

FIG. 7. Inhibition of CD127 Signalling Pathways

The effect of various anti-human CD127 antibodies on the activation of signaling pathways was assessed by Western Blot as detailed in Example 8. The figure represents representative results from 6 different donors. "No IL-7" corresponds to a sample which was not stimulated by IL-7. "C" corresponds to a control sample, stimulated with IL-7 in the absence of anti-CD127 antibody. Horizontal lines left of the blot represent the migration of the indicated molecular weight marker. Arrows right of the blot indicate the migration of tyrosine-phosphorylated STAT5, tyrosine 199-phosphorylated PI3-k p55, phosphorylated Akt, phosphorylated ERK 1/2, and, as a loading reference, GAPDH.

FIG. 8A,B. Smothering of T-Cell Cytokine Release from UC Biopsies

Panel A. IFNγ production by UC biopsy samples grown ex-vivo. Panel B. IFNγ production by CD biopsy samples grown ex-vivo.

In both panels, the samples were obtained and treated as detailed in Example 9. Each symbol represents one sample from a patient, cultured with IgG ("Ctrl Ab") or with anti-CD127 antibody ("aIL-7Rα"). Connected symbols are paired samples from the same patient. ** p<0.01 with Wilcoxon matched pairs test. IFNγ production was significantly inhibited by anti-IL7Ra mAb. Similar results were observed for CD biopsy samples.

FIG. 9A,B. Anti-Human IL-7Rα mAbs and Agonist Signals

The effect of various anti-human CD127 antibodies on the activation of STAT5, PI3K and ERK signaling pathways was assessed by Western Blot as detailed in Example 11. The FIG. 9A shows from one out of seven different donor cells in the absence of exogenous recombinant human IL7. Panel A. "medium" corresponds to a sample without any anti-human CD127 antibody. "No IL7" means that the four samples were not stimulated with IL-7. Three samples were pretreated with 10 µg/mL of one anti IL-7Rα mAb (N13B2-hVL6 or MD707-13-G4 or 1A11-G1).

Panel B. Quantification of p13K and pERK corrected to GAPDH expression and normalized to medium control conditions (n=7 different donnors). The vertical axis represents the normalized expression to control. The value is plotted for each sample in a single group, the horizontal bar representing the average value for the group, and error bars representing the standard deviation.

Figure 10:
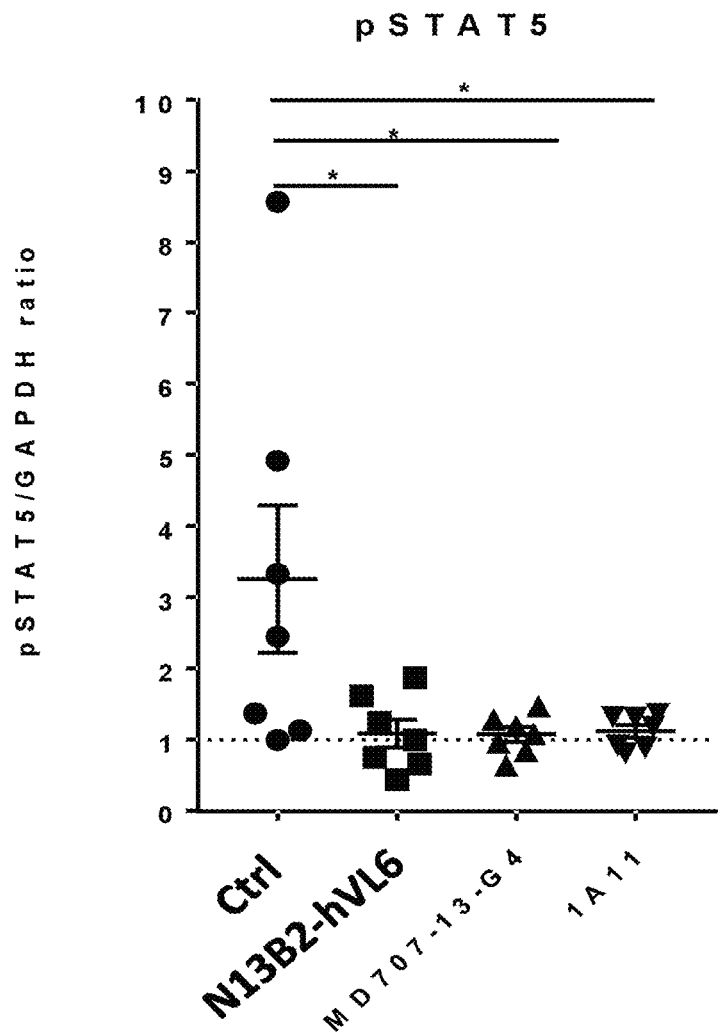

FIG. 10. Effect of Anti-Human IL7-Rα mAbs on IL7 Pathway Activation

The quantification of phospho-STAT5 signal was corrected to GADPH expression and normalized to medium control conditions. PBMCs were pretreated with 10 µg/mL of one anti-IL7-Ra mAb (N13B2-hVL6 or MD707-13-G4 or 1A11) and then incubated for 10 min at 37° C. with 5 ng/mL of human IL7. Quantifications of phospho-STAT5 signal were corrected to GAPDH expression (n=7 different donors). The dotted line represents the condition with medium alone without treatment. The value is plotted for each sample in a single group, the horizontal bar representing the average value for the group, and error bars representing the standard deviation. "*" denotes a p-value<0.05 between indicated groups.

Figure 11C:
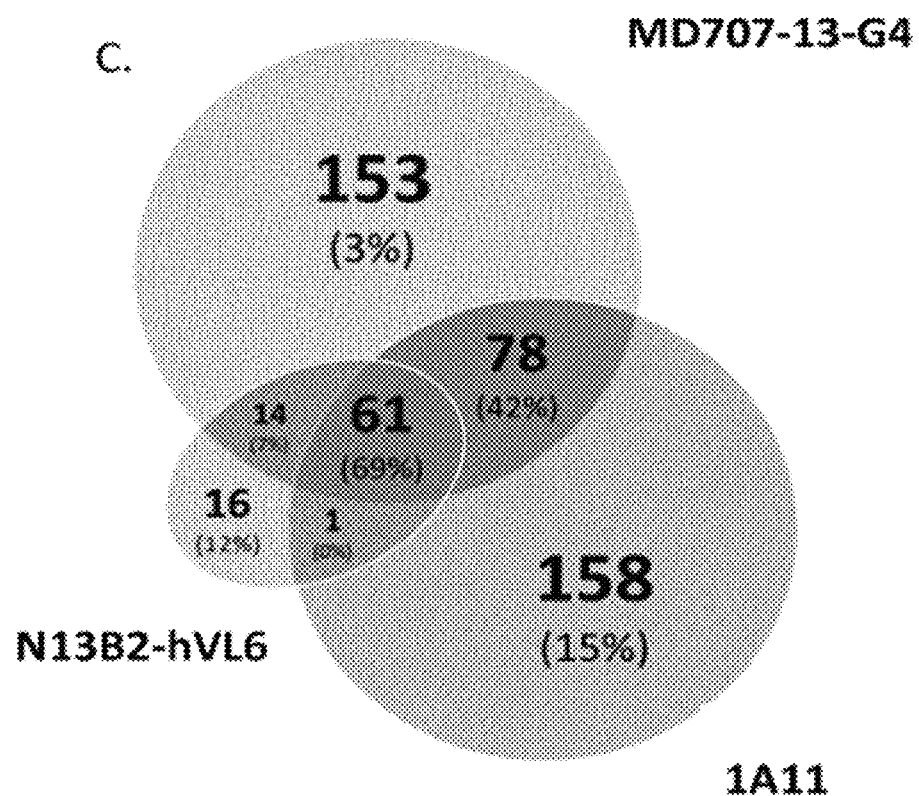

FIG. 11A,B,C. Dual Agonist/Antagonist Anti-IL7-Rα mAbs Induce Transcriptional Modifications RNA sequences analysis of human PBMCs (n=7) incubated for 3.5 hours (1) with 5 ng/ml of human IL7, (2) without IL7, (3,4,5) with 5 ng/mL of human IL7 and different anti-human IL7-Ra mAbs ((3): 10 µg/mL N13B2-hVL6; (4): 10 µg/mL MD707-13-Ig4; (5): 10 µg/mL 1A11).

Panel A. Heatmap of the expression of the 93 most differentially expressed genes (False Discovery Rate (FDR) 5%, Fold change (FD)>2) between IL7 stimulation and control conditions.

Panel B. Quantification of the median profile of the three IL7 induced clusters in IL7 stimulated, control and IL7 and anti-human IL7-Ra mAbs conditions.

Panel C. Venn diagram of RNA sequences analysis of human PBMCs (n=7) incubated without IL-7 for 3.5 hours with different anti-human IL-7Rα mAbs (10 µg/mL of N13B2-hVL6, 10 µg/mL MD707-13-Ig4 #1, or 10 µg/mL 1A11). Venn diagram of the 481 differentially expressed genes (FDR 5%, FC>1.5) comparing anti-human IL-7Rα mAbs and medium control conditions. Circle size is proportional to the number of genes for each category.

EXAMPLES

Example 1. Humanization of Light Chains

The following heavy chain was used in all experiments reported herein, unless provided otherwise N13B2 humanized_VH, nucleotide sequence (SEQ ID No: 13):
CAGGTGCAGCTGGTCGAATCAGGGGGGGGACTGGTCAAACCCGGGGCTCA

CTGCGTCTGTCATGTGCCGTCTCAGGCTTCACACTGAGCGACTACTATATG

GCATGGATCCGACAGGCACCAGGCAAGGGACTGGAGTGGGTGTCTACTATT

TCTGCCAGTGGCCTGAGGACCTACTATCCTGACAGTGTCAAGGGAAGGTTC

ACAATCTCACGGGATAACGCTAAAAATTCCCTGTACCTGCAGATGAACAGC

CTGAGAGCCGAAGACACCGCTGTGTACTATTGCGCTCGCCCACTGTCCGCA

CACTATGGCTTCAATTACTTTGATTATTGGGGCAGGGTACCCTGGTGACA

GTCTCCAGC

N13B2 humanized_VH, Amino-acid sequence (SEQ ID No: 7): see 0A

The following optimized nucleotide sequences were used for the production of the antibody light chains (the amino acid sequences of which are provided in 0B):

N13B2-h3 (SEQ ID No: 14):
GAGATCGTCATGACGCAGTCCCCCGCAACGCTCTCCGTCTCCCCGGGGAA

CGCGCGACCCTGTCGTGCAGGACCTCCGAGGACATCTACCAAGGCCTCGCG

TGGTATCAGCAGAAGCCCGGCCAGGCCCCGCGGCTGTTGATCTACTCCGCG

AACACCTTGCACATCGGCATCCCGGCGCGCTTCTCGGGGTCAGGGAGCGGC

-continued

ACCGAGTTCACCCTGACCATCTCGTCGCTCCAGAGCGAGGACTTCGCCGTG

TACTACTGCCAGCAGTACTACGACTACCCCCTGGCGTTCGGGGCGGGACC

AAGGTGGAGATCAAG

N13B2hVL3 (SEQ ID No: 15):
GACATTCAGATGACCCAGTCCCCCTCGAGCCTGAGTGCGAGTGTGGGCGAC

CGCGTGACGATCACCTGCCGGACGTCCGAGGATATCTACCAGGGCCTCGCC

TGGTACCAGCAGAAGCCGGGCAAGGCCCCCAAACTGCTGGTCTACAGCGCG

AACACCCTCCACATCGGCGTCCCCAGCCGGTTCAGCGGCTCCGGCTCGGA

ACGGACTACACCCTCACGATCTCGTCCCTGCAGCCGGAAGACTTCGCCACC

TACTTCTGCCAGCAGTATTACGACTACCCGCTGGCGTTCGGTGGCGGCACC

AAGGTCGAGATCAAG

N13B2hVL4 (SEQ ID No: 16):
GACATTCAGATGACCCAGTCCCCCTCGAGCCTGAGTGCGAGTGTGGGCGAC

CGCGTGACGATCACCTGCCGGACGTCCGAGGATATCTACCAGGGCCTCGCC

TGGTACCAGCAGAAGCCGGGCAAGGCCCCCAAACTGCTGCTCTACAGCGCG

AACACCCTCCACATCGGCGTCCCCAGCCGGTTCAGCGGCTCCGGCTCGGGA

ACGGACTACACCCTCACGATCTCGTCCCTGCAGCCGGAAGACTTCGCCACC

TACTTCTGCCAGCAGTATTACGACTACCCGCTGGCGTTCGGTGGCGGCACC

AAGGTCGAGATCAAG

N13B2hVL5 (SEQ ID No: 17):
GACATTCAGATGACCCAGTCCCCCTCGAGCCTGAGTGCGAGTGTGGGCGAC

CGCGTGACGATCACCTGCCGGACGTCCGAGGATATCTACCAGGGCCTCGCC

TGGTACCAGCAGAAGCCGGGCAAGGCCCCCAAACTGCTGGTCTACAGCGCG

AACACCCTCCACATCGGCGTCCCCAGCCGGTTCAGCGGCTCCGGCTCGGGA

ACGGACTACACCCTCACGATCTCGTCCCTGCAGCCGGAAGACTTCGCCACC

TACTACTGCCAGCAGTATTACGACTACCCGCTGGCGTTCGGTGGCGGCACC

AAGGTCGAGATCAAG

N13B2hVL6 (SEQ ID No: 18):
GACATTCAGATGACCCAGTCCCCCTCGAGCCTGAGTGCGAGTGTGGGCGAC

CGCGTGACGATCACCTGCCGGACGTCCGAGGATATCTACCAGGGCCTCGCC

TGGTACCAGCAGAAGCCGGGCAAGGCCCCCAAACTGCTGCTCTACAGCGCG

AACACCCTCCACATCGGCGTCCCCAGCCGGTTCAGCGGCTCCGGCTCGGGA

ACGGACTACACCCTCACGATCTCGTCCCTGCAGCCGGAAGACTTCGCCACC

TACTACTGCCAGCAGTATTACGACTACCCGCTGGCGTTCGGTGGCGGCACC

AAGGTCGAGATCAAG

Each VL sequence was obtained by gene synthesis, inserted in a cloning vector (pUC57) with BsiWI 5' and 3' extremities and the addition of a Kozak sequence (GC-CACC) before the ATG. As expression vector, pFuseCLIg-hk expression plasmid (Invivogen) was used, containing the CLkappa constant domain of human IgG1.

Each cloning plasmid (VL-pUC57-Genscript) was digested by BsiWI restriction enzyme to extract the VL insert (400 bp). The purified insert was ligated in the expression plasmid pFuseCLIg-hk linearized by BsiWI digestion and dephosphorylated. Positive clones, which have VL fragments inserted in the right orientation before human constant domains, were amplified and purified by Midiprep-endotoxin free (Macherey-Nagel) for transfection step. The heavy chain was cloned in a similar fashion, with the constant domain consisting of SEQ ID No:26.

Example 2. Production of Humanized Light Chains

For the tested humanized anti-CD127 antibodies, transfection and selection of stable clones were made according to conventional methods. Three supernatants for each antibody corresponding to different ratio of transfection of the heavy chain (HC) and light chains (LC) were prepared and tested: 2:1, 1:1.3, and 1:2 HC:LC. Titers obtained are reported in 0, obtained following production in CHO cells seeded at 300,000 cells/mL; without antibiotics, according to conventional methods: the titer was assayed by ELISA on immobilized anti-human IgG (Fc) of the corresponding antibody and revelation was performed with a mouse anti-human kappa mAb plus peroxidase-labeled donkey anti-mouse antibodies and revealed by colorimetry at 450 nm using TMB substrate.

Production of N13B2-h3 and N13B2-hVL6 was also tested in transient transfection experiments. One day before transfection, COS cells were seeded at 100 000 cells/well in P12 plate with completed medium (DMEM SVF10% (Hyclone)+PS 1%+Glu 1%) and incubated at 37° C., 5% CO2. The day of transfection, COS cells were used at 50 to 90% confluence. They were washed with PBS and kept with 500 μl in completed medium. 0.6 μg VH variant+0.4 μg VL variant were mixed in 200 μl OptiMEM medium and 1 μl of Plus Reagent (Invitrogen) was added (incubation 15 min at room-temperature). 3.5 μl lipofectamine LTX (Invitrogen)+100 μl were added in the mix and incubated 25 min at room-temperature. The whole mix was deposited drop by drop on COS cells and incubated 48h at 37%, 5% CO2. After 48h, supernatants were harvested and centrifuged (1500 rpm 10 min 4° C.). Supernatants were quantified with ELISA n° TH-MO-43. Activity assay was made with ELISA TH-MO-44.

Example 3. Binding to CD127—ELISA

For sandwich ELISA, donkey anti-human IgG (Fc specific) antibody was coated at 1.2 μg/ml on P96-plate and purified antibodies were added to measure concentration in function of standard range. After incubation and washing, mouse anti-human light chain, kappa specific, (Effimune, clone NaM76-5F3) plus peroxidase-labeled donkey anti-mouse (Jackson Immunoresearch, reference 715-036-151) antibodies were added and revealed by conventional methods.

For activity ELISA assay, recombinant hCD127 (Sino Biologicals, Beijing, China; reference 10975-H08H) was immobilized on plastic at 1 μg/ml and dilutions of anti-CD127 antibody were added to measure binding After incubation and washing, mouse anti-human light chain (kappa specific) plus peroxidase-labeled donkey anti-mouse antibodies were added and revealed by colorimetry at 450 nm using TMB substrate by conventional methods.

The following ED50 values were obtained (concentration required to achieve 50% of the maximum signal):

TABLE 1

ED50 value (in ng/ml) for binding to CD127 of the antibodies

| | ED50 (ng/ml) |
|---|---|
| N13B2-h3 | 16.8 |
| N13B2-hVL3 | 15.1 |
| N13B2-hVL4 | 12.6 |
| N13B2-hVL5 | 14.8 |
| N13B2-hVL6 | 9.5 |

Stability of the antibodies was studies by incubating the antibodies for 7, 14, or 30 days at 4° C., 25° C. and 42° C. The binding of the antibodies to CD127 was still excellent even after 30 days incubation. Values of ED50 determined by ELISA after 30 days of incubation are reported in table 2.

TABLE 2

ED50 value (in ng/ml) for binding to CD127 of the antibodies, after 30 days incubation at the indicated temperature.

| | ED50 (ng/ml) |
|---|---|
| N13B2-hVL6 d7 at 4° C. | 55.31 |
| N13B2-hVL6 d7 at 25° C. | 47.83 |
| N13B2-hVL6 d7 at 42° C. | 56.16 |
| N13B2-hVL6 d14 at 4° C. | 62.75 |
| N13B2-hVL6 d14 at 25° C. | 52.58 |
| N13B2-hVL6 d14 at 42° C. | 40.62 |
| N13B2-hVL6 d30 at 4° C. | 46.98 |
| N13B2-hVL6 d30 at 25° C. | 40.19 |
| N13B2-hVL6 d30 at 42° C. | 58.69 |

Example 4. Binding to CD127—Blitz

This method was performed with a Blitz (Forte Bio, C22-2 No 61010-1).
Recombinant hCD127 (Sino Biologicals, Beijing, China; reference 10975-H08H)/recombinant protein (Sino Biological Cat: 11612-H08H) was immobilized at 50 µg/ml by Fc fragment into anti-human IgG Fc (AHC) biosensor (Forté Bio, 18-5063) for 30 seconds. Then, anti-CD127 antibodies were added at 20 µg/mL (saturating concentration) for an association period of 120 seconds, followed by a dissociation period of anti-CD127 antibody in kinetics buffer for 120 seconds. Data analysis was made with the Blitz pro 1.2 software, which calculated association constant (ka) and dissociation constant (kd) and determined the affinity constant KD (ka/kd). Results are reported in Table 3.

TABLE 3

Affinity analysis by Blitz of anti-CD127 antibodies on human CD127 recombinant protein

| | Association (ka) (1/Ms) | Dissociation (kd) (1/s) | Affinity (KD) (M) |
|---|---|---|---|
| N13B2-h3 | 1.15e6 | 2.67e-3 | 2.33e-9 |
| N13B2-hVL3 | 1.27e6 | 4.47e-3 | 3.51e-9 |
| N13B2-hVL4 | 1.04e6 | 2.81e-3 | 2.71e-9 |
| N13B2-hVL5 | 1.01e6 | 2.66e-3 | 2.63e-9 |
| N13B2-hVL6 | 1.05e6 | 2.66e-3 | 2.53e-9 |

Example 5. Inhibition of STAT5 Phosphorylation

To test inhibition of IL7R in functional assay, antibody was incubated with human PBMC for 30 min at 37° C., before stimulating with IL7 (AbD Serotec, ref PHP046) at 0.1 ng/ml for 15 min at 37° C. Reaction was stopped a 4° C., and washed with Perm Wash buffer before fixation with Cytofix/Cytoperm kit (BD Bioscience, ref 554722) for 15 min at 4° C. Cells were washed and stained with FITC-labelled anti-CD3 (BD Bioscience, ref 557694) for 30 min at 4° C. Then, cells were permeabilized in incubating Perm Buffer III (BD Bioscience, ref 558050) for 30 min at 4° C. After washing with PBS BSA1% Azide 0.1%, cellq were stained with Alexa-647 labelled anti-pStat5 antibody (BD Bioscience, ref 612599) for 30 min at room-temperature. Samples were analysed on BD CantoII cytofluorometer. hPBMC-CD3+ with IL7 induced phosphorylation of pStat5, whereas, without IL7, we have no phosphorylation. Results are reported in 0 and the table below, displaying ED50, i.e. the concentration of the indicated antibody to reach 50% of the signal in this assay.

TABLE 4

Inhibition of STAT5 phosphorylation by anti-CD127 antibodies

| | IC50-MFI (ng/ml) |
|---|---|
| N13B2-h3 | 21.5 |
| N13B2-hVL3 | 27.2 |
| N13B2-hVL4 | 16.1 |
| N13B2-hVL5 | 27.3 |
| N13B2-hVL6 | 16.8 |

This experiment confirmed that modification of germline and modification of structural residues by humanized amino-acid did not change the biological activity of anti-CD127 antibody. All tested variants (N13B2-h3, N13B2-hVL3, N13B2-hVL4, N13B2-hVL5, N13B2-hVL6) could inhibit Stat5 phosphorylation after IL7 stimulation on hPBMC, like previously produced reference batches of N13B2. Focusing on N13B2-hVL6 (the most humanized and the most optimized), we noticed that it was able to maintain its biological activity in inhibiting Stat5 phosphorylation, to the same extent than reference N13B2-h3. Moreover, this variant was very stable after 14 days of incubation at 42° C., 25° C. or 4° C., it did not induce aggregate formation, and maintained its binding activity.

Example 6. Effect on Memory T Cells

Tuberculin-Induced Delayed-Type Hypersensitivity Model

Baboons were immunized intradermally twice with a *bacillus* Calmette-Guerin vaccine (0.1 ml; 2-8 105 CFU; Sanofi Pasteur MSD, Lyon, France) in the upper region of the leg, 4 and 2 weeks before the delayed-type hypersensitivity (DTH) skin test. Intradermal reactions (IDR) were performed with intradermal injections of 2000 or 1000 UI of Tuberculin Purified Protein Derivative (PPD; Symbiotics Corporation, San Diego, CA). Saline (0.1 ml) was used as a negative control. Dermal responses at the injection sites were measured using a caliper square by at least two observers and were considered positive when >4 mm in diameter. A second IDR was performed after a three-week washout period and animals received one intravenous injection of 10 mg/Kg of N13B2 (n=7) or 10 mg/kg (V915GA, AA892BB, 32257, 33874) (n=4) of humanized N13B2 or equivalent of volume excipient (n=4). Additional IDR were performed every month after the injection. After a washing period, some baboons (previously treated with N13B2) were immunized again intradermally twice with a BCG following by a new IDR. The mean of the reading was recorded and plotted for each time point. To compare multiple experimental conditions, erythema responses were quantified as area under the curve (AUC) using Graph Pad Prism software for calculation (0A and B).

Elispot

Ag-specific T cell frequency was followed with an IFN-g ELISPOT assay (non-human primate IFN-g ELISPOT kit; R&D Systems, Minneapolis, MN) on freshly isolated PBMC re-stimulated with tuberculin, according to the manufacturer's instructions.

Briefly, capture antibody (R&D systems, catalog number SEL961) was added in each well of a Elispot MultiScreen® FITS Filter Plates (Merck Millipore) and incubate one night at 4° C. After three washes, blocking buffer was added and plate was incubated 2 hours at ambient temperature. Baboons PBMC were extracted freshly from the blood of baboons by Ficoll gradient centrifugation (GE Healthcare Life Science, Paris, France). Red blood cell was then lyzed and cells washed before reconstitution at appropriate concentration in culture media (TexMacs media supplemented with penicillin-streptomycin (Gibco)) with or not tuberculin purified protein derivative. Plate was incubated at 37° C. and 5% CO2 during 18-24 hours. After three washes with wash buffer, detection antibody (R&D systems, catalog number SEL961) was added and incubated at 4° C. during 24 hours. Streptavidin-AP (R&D systems, catalog number SEL002) was added after three washes and incubated two hours at ambient temperature during 2 hours. Three washes have been done. BCIP/NBT (R&D systems, catalog number SEL002) have been added and put in the dark during 30 minutes. Several washes were necessary with wash buffer and one with deionized water (OC).

Animals

Baboons (*Papio anubis*; 7-14 kg) were obtained from the Centre National de la Recherche Scientifique Centre de Primatologie (Rousset, France). The animals were housed at the large animal facility of the INSERM unit 1064. Animal studies were approved by the French National Ethics Committee.

Results

In a first experiment, a first IDR with tuberculin was performed on BCG-vaccinated baboons which did not receive treatment at that time (day −30). After a washing period of one month, a second IDR was performed 4h and every month after i.v. injection of 10 mg/Kg of N13B2 (white bars). A last IDR was performed after a new vaccination with BCG (14 months post-antibody injection). Control animals (black bars) received similar volume of excipient i.v. and were challenged with same protocol. Results showed that anti-IL7Ra chimeric antibody induced a very long-term protection (up to 14 months) after a single administration. Response recovered only after new vaccination.

In another experiment, a first IDR with tuberculin was performed on BCG-vaccinated baboons (dashed bars—e.g. IDR1 for V915GA). After a washing period of one month, a second IDR was performed 4h and every month after i.v. injection of 10 mg/Kg of humanized N13B2 (solid bars— e.g. IDR2-6 for V915GA). A last IDR was performed after new vaccination with BCG and Tuberculine (dotted bars— e.g. IDR7 for V915GA). Control animals (black bars) received similar volume of excipient i.v. and were challenged with same protocol. Results showed humanized N13B2 induced also a long-term protection after a single administration in 3 out 4 evaluated baboons. "33874" animal was initially responder immediately after antibody injection but response recovered spontaneously one month later.

Blood PBMC were re-stimulated ex vivo with tuberculin. A first IFNγ elispot with or without tuberculin was performed on BCG-vaccinated baboons (dashed bars). A second IFNγ elispot was performed 4 days after injection with 10 mg/Kg of humanized N13B2 (fulled bars). New ELISPOT were then performed every month at each new IDR with tuberculin in vivo. A last IFNγ elispot was performed after new vaccination with BCG (dotted bars). Results showed that administration of humanized N13B2 induced antigen-specific memory T cells deletion in long-term responder animals. "33874" baboon did not show significant reduction of tuberculin-specific memory T cells in parallel to no long-term protection in DTH model. After new vaccination with BCG, long-term responder animals showed increased frequency of antigen-specific memory T cells which recover to basal level (before mAb injection) and this is associated with recovering of the DTH response in vivo. Altogether, these results demonstrated that long-term protection induced by humanized N13B2 is associated with antigen-specific memory T cells deletion which explain the long-term effect of the drug.

Example 7. Expression of IL-7, CD127 and TSLP in IBD Patients

Raw mRNA expression data obtained as detailed in Planell et al. Gut 2013 were analyzed as detailed in the legend to 0.

Example 8. Signaling Pathway of Human PBMC Stimulated with Anti-CD127 Antibodies Plus IL7

IL7 signaling pathways were studied from lysates of human PBMC incubated 30 min at 37° C. with 10 µg/ml of soluble anti-human CD127 antibodies, and stimulated with IL7 (AbD Serotec, ref PHP046) at 5 ng/ml for 10 min at 37° C. Western Blot were performed in reducing conditions with 20 µg protein of cellular lysates in 7.5% polyacrylamide gels and blotted onto nitrocellulose membranes (GeHealthcare). Blots were saturated with 5% BSA-Tris Buffer Saline (TBS) and revealed either with Phospho-Stat5, Phospho-PI3-Kinase p85, Phospho-Akt and Phospho-ERK1/2 antibody (Cell Signaling Technology) at 1/1000 in 1% BSA-TBS (overnight at 4° C.) followed by polyclonal goat anti-rabbit labeled horseradish peroxidase antibody (Cell Signaling Technology) at 1/2000 for 1 h at room temperature, or with GAPDH antibody (Santa Cruz) at 1/1000 in 1% BSA-TBS (overnight at 4° C.) followed by polyclonal goat anti-mouse labeled horseradish peroxidase antibody (Jackson Immunoresearch) at 1/2000 for 1 h at room temperature. Membranes were revealed by chemiluminescence using LAS-3000 imaging system (Fujifilm). The following anti-human CD127 antibodies were thus assayed: N13B2-h3 and N13B2-hVL6 (both anti-site 1/2b antibodies, disclosed herein); MD707-13-G4 ("anti-site 1 antibody", disclosed in Int. Pat. Appl. WO2013/056984) and 1A11 (disclosed in GSK patent WO2011/094259).

Example 9. Effect on T-Cell Cytokine Release in IBD Tissue

Biopsies from patients with MD can be used as an inflammatory model of disease ex-vivo and have been shown here to spontaneously release high levels of proinflammatory cytokines after 24 hours of culture (UC: IFNγ, 130±19 pg/ml; IL-6, 4042±529 pg/ml; IL-8, 25626±1640 pg/ml—CD: IFNγ, 180±38 pg/ml; IL-6, 3653±734 pg/ml; IL-8, 15540±2452 pg/ml [means±sem for UC and CD respectively]).

Anti-CD127 mAb was applied at 10 μg/ml in this organ culture assay using surgical specimens taken from inflamed colonic mucosa of 20 patients with IMD (10 with Crohn's disease and 10 with ulcerative colitis and the culture was performed at 37° C. for 24 hours in medium with 10 μg/ml of IgG control mAb or blocking anti-human IL-7Rα mAb (see details of sampling and culture conditions below). A paired control specimen from each patient was sampled and cultured in the same conditions, with IgG control instead of anti-CD127 antibody. Cytokines concentration was measured by ELISA (as detailed below) in the supernatant of the ex-vivo cultured samples.

IFNγ production by UC biopsy samples grown ex-vivo was significantly inhibited by anti-IL7Rα mAb. Similar results were observed for some CD biopsy samples secreting high amount of IFNγ.

Ex-Vivo Organ Sampling and Culture

If mucosal resection tissue was used, small biopsy-size fragments were cut using scissors. Next, biopsies or biopsy-size fragments were placed in 300 μL serum-free HL-1 medium (Lonza, Cambridge BioScience, UK) supplemented with L-Glutamine, 100 U/mL penicillin, 100 μg/mL streptomycin and 50 μg/mL gentamycin. Mucosal explants were incubated for 24h at 37C and 5% $CO_2$. The respective tested antibody (N13B2) or IgG control used at 10 μg/mL was added into the medium at the beginning of incubation time. Finally, supernatant and biopsy material was snap frozen and stored at −70° C. for future analysis.

Enzyme-Linked Immunosorbent (ELISA) Assay

Cytokine production in biopsy supernatant was measured by enzyme-linked immunosorbent assay (ELISA). Human recombinant IFN-γ from ImmunoTools (#31673539, Friesoythe, Germany) was used accordingly to the manufacture's instruction.

Example 10. Comparison of Anti-Human IL7-Rα Antibodies Related to their Epitope Characterization Mass Spectrometry Analysis: Antibody Profiling Using Peptide Microarray The peptide Technologies' PepStar™ peptide microarrays comprise purified synthetic peptides derived from antigens or other sources that are chemoselectively and covalently immobilized on a glass surface. An optimized hydrophilic linker moiety is inserted between the glass surface and the antigen-derived peptide sequence to avoid false negatives caused by sterical hindrance. For technical reasons all peptides contain a C-terminal glycine. Profiling experiments of samples were performed on a peptide library consisting of 52 peptides. The complete list of peptides is shown below:

TABLE 5

List of peptides used in peptide microarray assays

| SEQ ID | Sequence |
|---|---|
| 44 | ESGYAQNGDLEDAEL |
| 45 | AQNGDLEDAELDDYS |
| 46 | DLEDAELDDYSFSCY |
| 47 | AELDDYSFSCYSQLE |
| 48 | DYSFSCYSQLEVNGS |
| 49 | SCYSQLEVNGSQHSL |
| 50 | QLEVNGSQHSLTCAF |
| 51 | NGSQHSLTCAFEDPD |
| 52 | HSLTCAFEDPDVNTT |
| 53 | CAFEDPDVNTTNLEF |
| 54 | DPDVNTTNLEFEICG |
| 55 | NTTNLEFEICGALVE |
| 56 | LEFEICGALVEVKCL |
| 57 | ICGALVEVKCLNFRK |
| 58 | LVEVKCLNFRKLQEI |
| 59 | KCLNFRKLQEIYFIE |
| 60 | FRKLQEIYFIETKKF |
| 61 | QEIYFIETKKFLLIG |
| 62 | FIETKKFLLIGKSNI |
| 63 | KKFLLIGKSNICVKV |
| 64 | LIGKSNICVKVGEKS |
| 65 | SNICVKVGEKSLTCK |
| 66 | VKVGEKSLTCKKIDL |
| 67 | EKSLTCKKIDLTTIV |
| 68 | TCKKIDLTTIVKPEA |
| 69 | IDLTTIVKPEAPFDL |
| 70 | TIVKPEAPFDLSVIY |
| 71 | PEAPFDLSVIYREGA |
| 72 | FDLSVIYREGANDFV |
| 73 | VIYREGANDFVVTFN |
| 74 | EGANDFVVTFNTSHL |
| 75 | DFVVTFNTSHLQKKY |
| 76 | TFNTSHLQKKYVKVL |
| 77 | SHLQKKYVKVLMHDV |
| 78 | KKYVKVLMHDVAYRQ |
| 79 | KVLMHDVAYRQEKDE |
| 80 | HDVAYRQEKDENKWT |
| 81 | YRQEKDENKWTHVNL |
| 82 | KDENKWTHVNLSSTK |

TABLE 5-continued

List of peptides used in peptide microarray assays

| SEQ ID | Sequence |
|---|---|
| 83 | KWTHVNLSSTKLTLL |
| 84 | VNLSSTKLTLLQRKL |
| 85 | STKLTLLQRKLQPAA |
| 86 | TLLQRKLQPAAMYEI |
| 87 | RKLQPAAMYEIKVRS |
| 88 | PAAMYEIKVRSIPDH |
| 89 | YEIKVRSIPDHYFKG |
| 90 | VRSIPDHYFKGFWSE |
| 91 | PDHYFKGFWSEWSPS |
| 92 | FKGFWSEWSPSYYFR |
| 93 | WSEWSPSYYFRTPEI |
| 94 | SPSYYFRTPEINNSS |
| 95 | YFRTPEINNSSGEMD |

A total of 4 samples were incubated on microarray slides using a Multiwell-format. For N13B2-h3VL6 antibody and the other sample (MD707-13, HAL and 1A11), 6 different concentrations were applied (10 µg/ml; 2 µg/ml; 1 µg/ml; 0.1 µg/ml; 0.01 µg/ml; 0.001 µg/ml). Serial sample dilutions were incubated for 1 hour at 30° C. on a multi-well microarray slide, containing 21 individual mini-arrays (1 mini-array per sample dilution). Subsequent to sample incubation, a secondary anti human IgG antibody at 1 µg/ml was added and left to react for 1 hour. An additional control incubation applying the secondary antibody only was performed in parallel on the same microarray slide to assess false-positive binding to the peptides. After washing and drying, the slide was scanned with a high-resolution laser scanner at 635 nm to obtain fluorescence intensity profiles. Resulting images were quantified to yield a mean pixel value for each peptide. Secondary antibody anti-human IgG labeled with Cy5 at 1 µg/ml.

Buffers and solutions The buffer used were TBS-buffer including 0.05% Tween20 (JPT) and Assay buffer T20 (Pierce, SuperBlock TBS T20, #37536). Acquisition and analysis were performed using Peptide microarrays (JPT Peptide Technologies GmbH, Berlin, Germany; batch #2668, Multi-Well incubation chamber, Axon Genepix Scanner 4200AL, Microarrays were scanned using a high resolution fluorescence scanner. Laser settings and applied resolution were identical for all performed measurements. The resulting images were analyzed and quantified using spot-recognition software GenePix (Molecular Devices). For each spot, the mean signal intensity was extracted (between 0 and 65535 arbitrary units).

For further data evaluation, the so called MMC2 values were determined. The MMC2 equals the mean value of all three instances on the microarray except when the coefficient of variation (CV)—standard-deviation divided by the mean value—is larger 0.5. In this case the mean of the two closest values (MC2) is assigned to MMC2.

Deuterium Analysis

Using the HDX-2 system (Waters S.A./N.V.; Zellik, Belgium), recombinant human CD127 and 0 or 1 molar equivalent of mAb were mixed and diluted in 99.9% D20, 10 mM sodium phosphate, 100 mM NaCl, pH 6.8 to a final D20 content of 90% and a CD127 or CD127/mAb complex concentration of 27.5 µM. Hydrogen-deuterium exchange was performed at 20.0° C. for 30 minutes. The exchange was quenched by a 1:1 (v/v) dilution of samples with 100 mM sodium phosphate, 4M guanidine·HCl, 0.4M TCEP, pH 2.3, at 1.0° C. resulting in a final pH of 2.5. After 2 minutes, the quenched samples were loaded onto the HDX manager for online pepsin digestion at 20.0° C. (Enzymate BEH Pepsin, 2.1×30 mm; 5 µm), followed by desalting (Acquity BEH C18 Vanguard 2.1 mm×5 mm; 1.7 µm) and reverse phase separation (Acquity BEH C18 1.0 mm×100 mm; 1.7 µM) using a gradient from 5%-40% 0.2% formic acid in acetonitrile (pH 2.5) for 10 min at a flow rate of 40 µl/min at 0.0° C. Mass spectrometry analysis was performed on a Waters Xevo G2-XS ESI-Q-TOF mass spectrometer in the positive ion mode, with lockspray correction. Mild source conditions (temperature: 90° C., capillary voltage: 2.5 kV, sampling cone: 30V, desolvation gas flow: 800L/h, desolvation temperature: 250° C.) were used in order to minimize back-exchange while ensuring proper desolvation (73). Peptide identification was assisted by collision induced dissociation collected in the MSE mode, using PLGS 3.0.2 and UNIFI 1.8. Deuterium incorporation was determined in DynamX 3.0. Structural figures were prepared using PyMOL 1.8.2.3 (Schrödinger LLC, Cambridge, MA, USA) from PDB ID 3DI3(19). Monobasic and dibasic sodium phosphate, sodium chloride, guanidine hydrochloride, Tris(2-carboxyethyl)phosphine hydrochloride (TCEP), 50% sodium hydroxide, and formic acid were purchased from Sigma Aldrich (Schnelldorf, Germany) at the highest available purity. LC-MS grade solvents were sourced from Biosolve Chimie (Dieuze, France), deuterium oxide (99.9% D) and 20% deuterium chloride in deuterium oxide (99.96% D) from Cambridge Isotope Laboratories (Andover, MA, USA), hydrochloric acid 37% from VWR International (Fontenay-sous-Bois, France), and bovine cytochrome C digest from Thermo Fisher Scientific (Germering, Germany). Amicon ultra-centrifugal filters (0.5 mL; 10 kDa cut-off) were obtained from Merck Millipore (Molsheim, France).

Results

Epitope characterization by linear peptide array of different anti-IL7Ra mAbs identified two types of antagonist mAbs: (1) mAbs binding to the region (site-1) of interaction with IL-7, as previously described by two other groups (clone 1A11 described in WO/2011/094259 and clone HAL described in WO/2011/104687) and including MD707-13, and (2) a mAb, i.e. N13B2-h3VL6 of the present invention, which binds both site-1 and an epitope overlapping the predicted domain (site-2b) of heterodimerization between IL-7Rα and the γ-chain subunits (Walsh 2012).

N13B2-h3VL6 and MD707-13 with high and similar affinities (the binder to site-1/2b with a KD of $2.10^{-10}$ M and a binder to site-1 with a similar KD of $5.10^{-10}$ M) were recombinantly expressed with a human IgG4 Fc isotype (containing the S228P hinge mutation to prevent Fab-arm exchange) and compared to a previously described other site-1 mAb with similar affinity, clone 1A11, described in WO/2011/094259 (KD of $6.10^{-10}$ M) and recombinantly expressed with a human IgG1 Fc isotype as being developed in the clinic (NCT02293161). Analysis of conformational epitope using Hydrogen Deuterium Exchange with Mass Spectrometry (HDX-MS) confirmed previous observations and demonstrated that the antibody of the invention, i.e. N13B2-h3VL6 (site-1/2b mAb), protected from deuterium incorporation in several peptides of the site-1 but also to a peptide overlapping the site-2b, while the two other mAbs (MD707-13 and 1A11) significantly prevent deuterium incorporation only in peptides from site-1(Data not shown).

The antibody of the invention was the only one to recognize a conformational epitope localized on site 1 from Domain 1 and a conformational epitope localized on site 2b of human CD127.

Example 11. Comparison of Anti-Human IL-7Rα Antibodies for their Ability to be Agonist and/or Antagonist of the IL-7 Pathway Western Blotting Freshly isolated human PBMCs were incubated for 30 min at 37° C. with 10 µg/ml of anti-human IL-7Rα mAbs, and then cultured alone or with 5 ng/ml of recombinant human IL-7 (AbDSerotec) for 10 min at 37° C. After stopping the reactions on ice, cells lysates were prepared with RIPA buffer (with Protease Inhibitor Cocktail). Proteins (15 µg) were resolved under reducing conditions on 7.5% polyacrylamide gels and immobilized on nitrocellulose membranes (GeHealthcare) using standard methods. Blots were washed with 5% BSA-Tris Buffer Saline and incubated with Phospho-STAT 5, Phospho-PI3K p55 or Phospho-ERK specific antibodies in 1% BSA-TBS (overnight at 4° C.), followed by a polyclonal goat anti-rabbit horseradish peroxidase-labeled antibody (Cell Signalling Technology) for 1 h at room temperature. Alternatively, blots were stained using a GAPDH antibody (Santa Cruz) in 1% BSA-TBS (overnight at 4° C.), followed by polyclonal goat anti-mouse horseradish peroxidase labeled antibody (Jackson Immunoresearch) for 1 h at room temperature. Membranes were revealed by chemiluminescence using a LAS-3000 imaging system (Fujifilm).

RNA Sequencing

Freshly isolated human PBMCs were incubated with 10 µg/ml anti-human IL-7Rα mAbs (30 min at 37° C.), and then cultured alone or with 5 ng/ml of recombinant human IL-7 (AbDSerotec) for 3 hours at 37° C. Reactions were stopped on ice and the cell pellets resuspended in RLT buffer (Qiagen) containing 1% 13 mercaptoethanol in RNase/DNase free water and stored at −80° C. RNA was extracted using an RNA mini extraction kit according to manufacturer's instructions (Qiagen). The quality and quantity of RNA were assessed by infrared spectrometry (Nanodrop) and Agilent bioanalyzer (Agilent RNA 6000 Pico Kit). SmartSeq2 libraries were prepared by the Broad Technology Labs and sequenced by the Broad Genomics Platform according to the SmartSeq2 protocol with some modifications. Briefly, total RNA was purified using RNA-SPRI beads, polyA+ mRNA was reverse-transcribed to cDNA, and amplified cDNA was subject to transposon-based fragmentation that used dual-indexing to barcode each fragment of each converted transcript with a combination of barcodes specific to each sample. Sequencing was carried out as paired-end 2×25 bp with an additional 8 cycles for each index. Data was separated by barcode and aligned using Tophat version 2.0.10 with default settings. Transcripts were quantified by the Broad Technology Labs computational pipeline using Cuffquant version 2.2.1. Briefly, data were processed through CuffNorm if 50% of the reads aligned, and if at least 100,000 pairs were aligned per sample. Normalization used the default settings, including "geometric" normalization, and expression level information as log 2-transformed FPKM values (Fragments per kilobase of transcript per million mapped fragments) were used for subsequent analyses. For identification of differential genes, linear modeling with estimation of the mean-variance relationship (limmatrend) with empirical Bayes statistical procedure were performed using the limma package in R. Genes with Benjamini and Hochberg adjusted p-value<5% and fold change (FC)>1.5 were considered as differentially expressed. For gene expression representation, principal component analysis (PCA) and clustering were performed in R v3.3.2 using ade4/adegraphics and pheatmap packages respectively. The biological significance of selected genes was assessed using the R clusterProfiler package. Gene ontology (GO) categories enriched with a false discovery rate (FDR)<5% and with at least five represented genes were selected. RNA-seq data can be accessed under GEO accession number GSE.

Results

STAT5, PIK3 and ERK Signaling Pathways

Anti-human IL-7Rα mAbs (N13B2-h3VL6, MD707-13, 1A11 and HAL) were then compared for their ability to activate or block STAT5, PI3K and ERK signaling pathways previously associated with IL-7R signaling (FIGS. 9 and 10). As previously illustrated (see for example FIG. 7), IL-7 induces potent STAT5 phosphorylation on human PBMCs and all tested mAbs are potent inhibitors of this STAT5 phosphorylation (see FIG. 7). In contrast, and as illustrated on FIGS. 9 and 10, the inventors found that while IL-7 induces a variable PI3K phosphorylation and does not induce ERK phosphorylation, the antibodies of prior art (namely MD707-13, 1A11 and HAL) significantly induce ERK phosphorylation and to a lesser extent PI3K signal even in the absence of exogenous IL-7 on the contrary to the antibody according to the invention. These findings show that anti-human IL-7Rα antibodies of prior art have partial agonist properties, and are therefore considered as dual agonist/antagonist mAbs for the human IL-7R. On the contrary, an antibody according to the invention, and particularly N13B2-h3VL6, only has antagonist property for the human IL-7R.

The inventors assessed if the antibodies with agonist/antagonist properties could deliver an effective agonist signal capable of modifying human T cells. The transcriptomes of human PBMCs incubated for 3.5 hours without exogenous human IL-7, with human IL-7, and with IL-7 and an antibody (MD707-13, 1A11 site-1 (IgG4 #1 or IgG1 #2 respectively) or N13B2-hVL6 site-1/2b (IgG4)) have been analyzed by RNA-based-next generation sequencing (RNA-SEQ). A total of 481 genes were differentially expressed in human PBMCs incubated with anti-human IL-7Rα mAbs compared to control conditions, while a total of 334 genes were differentially expressed with human IL-7 stimulation alone compared to control conditions.

TABLE 6

List of genes significantly (FDR 5%) and differentially (fold-change > 1.5) expressed after incubation of human PBMCs (n = 7) with anti-IL7Ra mAbs compared to unstimulated cells.

| Gene | N13B2-h3VL6 | | MD707-13 IgG4 #1 | | 1A11 IgG1 #2 | |
|---|---|---|---|---|---|---|
| | logFC/Unstim | adj.P.Val | logFC/Unstim | adj.P.Val | logFC/Unstim | adj.P.Val |
| ACADVL | 0.85 | 0.040 | 1.15 | 0.001 | 0.87 | 0.011 |
| AHR | 0.86 | 0.029 | 1.16 | 0.000 | 1.21 | 0.000 |
| AKIRIN1 | 0.75 | 0.028 | 0.88 | 0.002 | 0.78 | 0.006 |
| ALDH16A1 | 1.23 | 0.021 | 1.45 | 0.001 | 1.32 | 0.003 |
| ALDH5A1 | 0.72 | 0.044 | 0.93 | 0.002 | 1.05 | 0.001 |
| APPBP2 | 0.81 | 0.001 | 0.90 | 0.000 | 0.81 | 0.000 |
| ARHGEF1 | 0.85 | 0.001 | 1.05 | 0.000 | 0.88 | 0.000 |
| B3GNT2 | 1.03 | 0.034 | 1.23 | 0.003 | 1.15 | 0.005 |
| C17orf59 | 1.07 | 0.039 | 1.49 | 0.001 | 1.27 | 0.004 |
| CCDC117 | 0.77 | 0.024 | 0.88 | 0.002 | 0.80 | 0.005 |
| CCNI | 0.73 | 0.004 | 0.98 | 0.000 | 0.78 | 0.001 |
| CDK17 | 0.98 | 0.003 | 1.09 | 0.000 | 0.94 | 0.001 |
| COTL1 | 1.67 | 0.000 | 1.80 | 0.000 | 1.35 | 0.000 |
| CYP1B1 | −0.66 | 0.029 | −0.75 | 0.003 | −0.69 | 0.006 |
| DDI2 | 1.17 | 0.011 | 1.45 | 0.000 | 1.24 | 0.002 |
| DEF6 | 1.03 | 0.030 | 1.39 | 0.001 | 1.09 | 0.006 |
| DNLZ | 1.17 | 0.029 | 1.19 | 0.008 | 1.22 | 0.006 |
| DUSP2 | 1.73 | 0.002 | 2.18 | 0.000 | 2.30 | 0.000 |
| ENG | −0.73 | 0.004 | −0.61 | 0.005 | −0.67 | 0.002 |
| EXOC8 | 0.69 | 0.043 | 0.62 | 0.033 | 0.63 | 0.026 |
| FAM160B1 | 0.83 | 0.030 | 1.26 | 0.000 | 0.72 | 0.024 |
| FEM1B | 0.99 | 0.005 | 1.09 | 0.000 | 0.87 | 0.005 |
| GCFC2 | 1.00 | 0.011 | 0.87 | 0.011 | 0.83 | 0.013 |
| GNA15 | 0.99 | 0.011 | 1.14 | 0.001 | 1.25 | 0.000 |
| GOPC | 0.83 | 0.015 | 0.64 | 0.029 | 0.69 | 0.015 |
| GRSF1 | 0.65 | 0.015 | 0.81 | 0.000 | 0.69 | 0.002 |
| HIPK3 | 0.67 | 0.025 | 0.79 | 0.002 | 0.69 | 0.006 |
| HMHA1 | 0.88 | 0.004 | 1.05 | 0.000 | 0.89 | 0.001 |
| HSBP1L1 | 1.04 | 0.029 | 0.97 | 0.017 | 0.86 | 0.030 |
| JUNB | 0.91 | 0.025 | 1.25 | 0.000 | 1.42 | 0.000 |
| KLC2 | 1.08 | 0.036 | 1.18 | 0.007 | 1.34 | 0.002 |
| LYSMD2 | 0.78 | 0.016 | 0.72 | 0.010 | 0.70 | 0.009 |
| LYZ | −0.60 | 0.031 | −0.86 | 0.000 | −0.76 | 0.001 |
| MS4A7 | −0.80 | 0.001 | −0.98 | 0.000 | −0.59 | 0.006 |
| MTA2 | 0.84 | 0.038 | 1.18 | 0.001 | 1.10 | 0.002 |
| NCOA5 | 0.65 | 0.018 | 0.84 | 0.000 | 0.89 | 0.000 |
| NSUN2 | 0.63 | 0.029 | 0.74 | 0.002 | 0.75 | 0.002 |
| PITHD1 | 0.81 | 0.040 | 1.03 | 0.002 | 0.81 | 0.013 |
| PLEKHF2 | 0.72 | 0.004 | 0.83 | 0.000 | 0.77 | 0.001 |
| POLRMT | 1.09 | 0.001 | 1.30 | 0.000 | 1.06 | 0.000 |
| PPP2CA | 0.75 | 0.025 | 0.87 | 0.002 | 0.75 | 0.007 |
| PREB | 0.88 | 0.018 | 0.78 | 0.014 | 0.92 | 0.004 |
| PRKCH | 0.70 | 0.011 | 0.88 | 0.000 | 0.78 | 0.001 |
| PSMD3 | 1.01 | 0.035 | 1.58 | 0.000 | 1.37 | 0.001 |
| PYGO2 | 1.08 | 0.003 | 1.07 | 0.001 | 0.74 | 0.016 |
| RASSF5 | 0.63 | 0.004 | 0.67 | 0.000 | 0.60 | 0.002 |
| RBL2 | 0.71 | 0.011 | 0.85 | 0.000 | 0.59 | 0.012 |
| RRP1 | 0.69 | 0.019 | 0.62 | 0.013 | 0.80 | 0.002 |
| SMCHD1 | 0.71 | 0.001 | 1.00 | 0.000 | 0.85 | 0.000 |
| SREBF2 | 0.83 | 0.009 | 1.13 | 0.000 | 0.98 | 0.000 |
| TAF10 | 1.87 | 0.001 | 1.57 | 0.001 | 1.28 | 0.006 |
| TAF4B | 0.75 | 0.030 | 1.12 | 0.000 | 1.29 | 0.000 |
| TMX4 | 1.04 | 0.009 | 1.13 | 0.001 | 0.89 | 0.009 |
| TPGS1 | 2.55 | 0.008 | 2.95 | 0.000 | 2.06 | 0.011 |
| TRAM1 | 0.71 | 0.001 | 0.73 | 0.000 | 0.59 | 0.002 |
| TRPC4AP | 0.98 | 0.005 | 1.21 | 0.000 | 1.06 | 0.001 |
| TTC13 | 0.76 | 0.034 | 0.90 | 0.003 | 0.68 | 0.022 |
| UNC119 | 1.02 | 0.036 | 1.43 | 0.001 | 1.26 | 0.002 |
| USP9X | 0.90 | 0.000 | 0.92 | 0.000 | 0.85 | 0.000 |
| VPS4A | 0.74 | 0.042 | 0.95 | 0.002 | 0.75 | 0.012 |
| ZNF800 | 0.74 | 0.013 | 1.01 | 0.000 | 0.84 | 0.001 |
| ACTN4 | 0.55 | 0.005 | 0.60 | 0.000 | 0.65 | 0.000 |
| C15orf48 | −0.63 | 0.029 | −0.87 | 0.000 | −0.51 | 0.035 |
| C3AR1 | −0.56 | 0.011 | −0.75 | 0.000 | −0.64 | 0.001 |
| CD247 | 0.80 | 0.004 | 0.87 | 0.000 | 0.50 | 0.038 |
| FAM50A | 0.66 | 0.028 | 0.93 | 0.000 | 0.54 | 0.031 |
| HCK | −0.65 | 0.009 | −0.83 | 0.000 | −0.46 | 0.030 |
| IL6ST | 0.43 | 0.034 | 0.60 | 0.000 | 0.77 | 0.000 |
| JAK1 | 0.71 | 0.001 | 0.80 | 0.000 | 0.58 | 0.002 |
| KYNU | −0.60 | 0.018 | −0.94 | 0.000 | −0.56 | 0.007 |
| NCF2 | −0.57 | 0.029 | −0.71 | 0.001 | −0.70 | 0.001 |

TABLE 6-continued

List of genes significantly (FDR 5%) and differentially (fold-change > 1.5) expressed after incubation of human PBMCs (n = 7) with anti-IL7Ra mAbs compared to unstimulated cells.

| Gene | N13B2-h3VL6 logFC/ Unstim | adj.P.Val | MD707-13 IgG4 #1 logFC/ Unstim | adj.P.Val | 1A11 IgG1 #2 logFC/ Unstim | adj.P.Val |
|---|---|---|---|---|---|---|
| PARP10 | 0.58 | 0.037 | 0.75 | 0.002 | 0.73 | 0.002 |
| RAD54L2 | 0.61 | 0.037 | 0.66 | 0.008 | 0.53 | 0.033 |
| SMG5 | 0.54 | 0.033 | 0.80 | 0.000 | 0.75 | 0.001 |
| TOR3A | 0.73 | 0.028 | 0.62 | 0.028 | 0.57 | 0.040 |
| ADM | −0.88 | 0.005 | −1.01 | 0.000 | −0.02 | 0.967 |
| CES1 | −0.77 | 0.028 | −0.78 | 0.008 | −0.45 | 0.145 |
| SLC31A2 | −0.79 | 0.004 | −0.60 | 0.012 | −0.17 | 0.577 |
| SMPDL3A | −1.11 | 0.009 | −1.12 | 0.002 | −0.56 | 0.149 |
| TREM1 | −0.72 | 0.009 | −0.67 | 0.005 | −0.28 | 0.287 |
| VNN1 | −0.97 | 0.030 | −1.17 | 0.002 | −0.35 | 0.423 |
| FLT1 | −1.01 | 0.028 | −0.66 | 0.101 | −0.80 | 0.039 |
| ABCG1 | 0.39 | 0.339 | 0.70 | 0.028 | 0.62 | 0.047 |
| ANKRD30BL | 0.88 | 0.342 | 1.42 | 0.049 | 1.73 | 0.012 |
| C16orf58 | 0.42 | 0.219 | 0.63 | 0.019 | 0.59 | 0.026 |
| C6orf120 | 0.31 | 0.536 | 1.03 | 0.003 | 0.84 | 0.013 |
| CA2 | −0.33 | 0.450 | −0.70 | 0.033 | −0.73 | 0.022 |
| CCNL2 | 0.51 | 0.178 | 0.75 | 0.012 | 0.59 | 0.049 |
| CD14 | −0.64 | 0.070 | −0.98 | 0.001 | −0.89 | 0.002 |
| CDK16 | 0.64 | 0.118 | 0.96 | 0.004 | 0.80 | 0.014 |
| CHTF18 | 0.67 | 0.174 | 0.87 | 0.030 | 1.13 | 0.004 |
| CLPTM1 | 0.74 | 0.111 | 1.06 | 0.005 | 1.01 | 0.007 |
| CREBZF | 0.50 | 0.116 | 0.72 | 0.006 | 0.67 | 0.008 |
| CREG1 | 0.70 | 0.095 | 0.86 | 0.013 | 0.99 | 0.004 |
| CSF1R | −0.39 | 0.263 | −0.71 | 0.010 | −0.92 | 0.001 |
| DAPK3 | 0.56 | 0.240 | 0.80 | 0.038 | 0.97 | 0.008 |
| DDRGK1 | 0.91 | 0.126 | 1.39 | 0.004 | 1.53 | 0.002 |
| DOHH | 1.40 | 0.061 | 1.45 | 0.020 | 1.69 | 0.006 |
| EMC8 | 0.61 | 0.229 | 1.15 | 0.004 | 1.04 | 0.008 |
| FAM115C | 0.37 | 0.264 | 0.61 | 0.022 | 0.64 | 0.013 |
| FUCA1 | −0.35 | 0.234 | −0.59 | 0.011 | −0.66 | 0.004 |
| GAPT | −0.48 | 0.188 | −0.67 | 0.023 | −0.85 | 0.003 |
| GMIP | 0.55 | 0.076 | 0.78 | 0.002 | 0.70 | 0.005 |
| GMPPB | 0.82 | 0.073 | 0.92 | 0.016 | 0.95 | 0.010 |
| HCG11 | 0.70 | 0.087 | 1.05 | 0.002 | 0.80 | 0.014 |
| HEATR3 | 0.43 | 0.280 | 0.74 | 0.019 | 0.74 | 0.017 |
| HEIH | 0.97 | 0.056 | 1.05 | 0.014 | 0.84 | 0.047 |
| HELZ2 | 0.42 | 0.287 | 0.77 | 0.013 | 0.77 | 0.010 |
| HMG20B | 0.54 | 0.088 | 0.61 | 0.019 | 0.59 | 0.022 |
| HNRNPA0 | 0.58 | 0.165 | 0.74 | 0.028 | 0.90 | 0.006 |
| HPCAL1 | 0.38 | 0.344 | 0.86 | 0.005 | 0.67 | 0.028 |
| KIAA1919 | 0.63 | 0.116 | 0.81 | 0.013 | 0.66 | 0.042 |
| KLHDC2 | 0.54 | 0.149 | 0.71 | 0.019 | 0.62 | 0.040 |
| LTB | 0.45 | 0.248 | 0.92 | 0.003 | 0.82 | 0.007 |
| MAF1 | 0.86 | 0.161 | 1.54 | 0.002 | 1.38 | 0.005 |
| MAFF | 0.54 | 0.249 | 0.81 | 0.029 | 1.19 | 0.001 |
| MAP3K11 | 0.49 | 0.263 | 0.77 | 0.030 | 0.70 | 0.044 |
| MGST1 | −1.05 | 0.089 | −1.24 | 0.015 | −1.06 | 0.036 |
| MIER2 | 0.89 | 0.112 | 0.93 | 0.047 | 1.25 | 0.006 |
| MOB2 | 0.69 | 0.150 | 1.05 | 0.007 | 0.90 | 0.017 |
| PET100 | −0.32 | 0.298 | −0.61 | 0.013 | −0.61 | 0.010 |
| PLK3 | 0.20 | 0.700 | 0.79 | 0.021 | 0.83 | 0.012 |
| POLG | 0.52 | 0.086 | 0.97 | 0.000 | 0.79 | 0.002 |
| PSMD2 | 0.41 | 0.212 | 0.62 | 0.018 | 0.61 | 0.017 |
| RAB13 | −0.50 | 0.089 | −0.73 | 0.002 | −0.62 | 0.009 |
| RASAL3 | 0.74 | 0.067 | 0.92 | 0.006 | 0.72 | 0.028 |
| RELB | 0.22 | 0.633 | 0.63 | 0.046 | 0.69 | 0.022 |
| RGMB | 0.58 | 0.173 | 0.80 | 0.020 | 0.74 | 0.028 |
| RNF10 | 0.56 | 0.095 | 0.67 | 0.016 | 0.66 | 0.014 |
| RNF149 | 0.60 | 0.077 | 0.69 | 0.016 | 0.69 | 0.012 |
| RPL39L | −1.02 | 0.125 | −1.09 | 0.049 | −1.41 | 0.008 |
| RPUSD1 | 0.76 | 0.105 | 0.84 | 0.031 | 1.00 | 0.008 |
| SCARF1 | 0.39 | 0.408 | 0.77 | 0.032 | 1.13 | 0.002 |
| SENP6 | 0.44 | 0.204 | 0.69 | 0.012 | 0.72 | 0.007 |
| SIPA1L3 | −0.01 | 0.992 | 0.71 | 0.021 | 0.74 | 0.013 |
| SLC25A22 | 0.51 | 0.283 | 0.75 | 0.047 | 0.83 | 0.024 |
| SLC38A10 | 0.24 | 0.595 | 0.76 | 0.014 | 0.66 | 0.030 |
| SLC43A2 | 0.66 | 0.068 | 0.63 | 0.040 | 0.99 | 0.001 |
| SPATC1L | 0.96 | 0.180 | 1.17 | 0.044 | 1.22 | 0.031 |
| SPP1 | −0.53 | 0.102 | −0.85 | 0.001 | −0.62 | 0.017 |
| SRP68 | 0.68 | 0.096 | 0.77 | 0.024 | 0.98 | 0.003 |
| TAZ | 0.95 | 0.092 | 1.23 | 0.008 | 1.22 | 0.007 |

TABLE 6-continued

List of genes significantly (FDR 5%) and differentially (fold-change > 1.5) expressed after incubation of human PBMCs (n = 7) with anti-IL7Ra mAbs compared to unstimulated cells.

| | N13B2-h3VL6 | | MD707-13 IgG4 #1 | | 1A11 IgG1 #2 | |
|---|---|---|---|---|---|---|
| Gene | logFC/Unstim | adj.P.Val | logFC/Unstim | adj.P.Val | logFC/Unstim | adj.P.Val |
| TCIRG1 | 0.79 | 0.069 | 1.15 | 0.001 | 1.15 | 0.002 |
| TNFRSF1B | 0.51 | 0.208 | 0.72 | 0.026 | 0.82 | 0.009 |
| TNFRSF4 | 0.23 | 0.751 | 0.97 | 0.034 | 1.15 | 0.009 |
| TNKS | 0.66 | 0.052 | 0.78 | 0.006 | 0.67 | 0.016 |
| TSC22D2 | 0.47 | 0.137 | 0.65 | 0.011 | 0.61 | 0.014 |
| UBA5 | 0.91 | 0.076 | 1.22 | 0.004 | 1.17 | 0.005 |
| USP48 | 0.64 | 0.145 | 0.90 | 0.012 | 0.72 | 0.044 |
| VPS51 | 0.50 | 0.145 | 0.82 | 0.003 | 0.76 | 0.005 |
| ZFAND5 | 0.56 | 0.054 | 0.71 | 0.003 | 0.64 | 0.007 |
| ZNF259 | 0.47 | 0.242 | 0.85 | 0.007 | 0.65 | 0.038 |
| ZNF496 | 0.51 | 0.220 | 0.86 | 0.008 | 0.83 | 0.009 |
| ZNF696 | 0.80 | 0.061 | 1.09 | 0.002 | 0.75 | 0.033 |
| ANXA1 | −0.43 | 0.034 | −0.49 | 0.005 | −0.63 | 0.000 |
| C12orf75 | −0.45 | 0.041 | −0.43 | 0.022 | −0.61 | 0.001 |
| C18orf32 | −0.56 | 0.040 | −0.61 | 0.008 | −0.48 | 0.036 |
| CHMP7 | 0.50 | 0.028 | 0.64 | 0.001 | 0.55 | 0.004 |
| DNAJC3 | −0.49 | 0.004 | −0.62 | 0.000 | −0.36 | 0.013 |
| EVI2B | −0.36 | 0.046 | −0.38 | 0.013 | −0.75 | 0.000 |
| HCST | −0.54 | 0.034 | −0.45 | 0.042 | −0.65 | 0.003 |
| HSBP1 | −0.44 | 0.009 | −0.64 | 0.000 | −0.46 | 0.002 |
| PAPOLA | 0.57 | 0.018 | 0.72 | 0.000 | 0.55 | 0.006 |
| PPBP | −0.55 | 0.018 | −0.65 | 0.001 | −0.50 | 0.010 |
| TIMP1 | −0.52 | 0.019 | −0.65 | 0.001 | −0.57 | 0.002 |
| TLR2 | −0.42 | 0.044 | −0.60 | 0.001 | −0.35 | 0.048 |
| UBE2D2 | 0.49 | 0.040 | 0.74 | 0.000 | 0.49 | 0.013 |
| AGTRAP | −0.52 | 0.040 | −0.66 | 0.002 | −0.42 | 0.051 |
| CXCL16 | −0.55 | 0.034 | −0.60 | 0.006 | −0.38 | 0.091 |
| P2RX4 | −0.48 | 0.034 | −0.60 | 0.002 | −0.06 | 0.846 |
| P2RX7 | −0.72 | 0.018 | −0.54 | 0.039 | 0.32 | 0.258 |
| SLAMF7 | −0.44 | 0.011 | −0.64 | 0.000 | −0.19 | 0.251 |
| SLC2A6 | −0.59 | 0.028 | −0.56 | 0.013 | −0.13 | 0.648 |
| SUGP2 | 0.64 | 0.005 | 0.50 | 0.012 | 0.33 | 0.114 |
| TNFAIP6 | −0.55 | 0.029 | −0.90 | 0.000 | −0.13 | 0.637 |
| TNIP3 | −0.55 | 0.028 | −0.61 | 0.004 | −0.21 | 0.385 |
| CYBA | −0.53 | 0.030 | −0.39 | 0.065 | −0.63 | 0.002 |
| EPG5 | 0.59 | 0.034 | 0.39 | 0.112 | 0.57 | 0.013 |
| RNF135 | −0.57 | 0.043 | −0.33 | 0.209 | −0.64 | 0.006 |
| ALDH1B1 | −0.79 | 0.036 | −0.38 | 0.294 | −0.36 | 0.311 |
| CKS2 | −0.85 | 0.048 | −0.61 | 0.109 | −0.59 | 0.116 |
| ETFDH | −0.71 | 0.003 | −0.36 | 0.090 | −0.40 | 0.054 |
| FPR1 | −0.87 | 0.029 | −0.62 | 0.076 | −0.29 | 0.467 |
| GSTT1 | −0.94 | 0.030 | −0.52 | 0.195 | −0.46 | 0.254 |
| NFYB | −0.61 | 0.025 | −0.42 | 0.075 | −0.14 | 0.633 |
| PREP | 0.72 | 0.030 | 0.48 | 0.102 | 0.48 | 0.092 |
| TGFBI | −0.99 | 0.007 | −0.27 | 0.477 | −0.36 | 0.310 |
| TMEM160 | −0.75 | 0.030 | −0.30 | 0.373 | −0.55 | 0.062 |
| TYMP | −0.75 | 0.040 | −0.38 | 0.278 | −0.17 | 0.687 |
| UBE3D | −0.96 | 0.046 | −0.35 | 0.477 | −0.33 | 0.497 |
| ZNF619 | 0.79 | 0.043 | 0.49 | 0.170 | 0.52 | 0.128 |
| ABCA1 | −0.43 | 0.068 | −0.60 | 0.002 | −0.39 | 0.044 |
| ACTR6 | −0.31 | 0.332 | −0.65 | 0.007 | −0.56 | 0.020 |
| ANXA5 | −0.40 | 0.089 | −0.66 | 0.001 | −0.39 | 0.046 |
| C16orf70 | −0.21 | 0.548 | −0.56 | 0.021 | −0.68 | 0.005 |
| CAND1 | 0.54 | 0.102 | 0.56 | 0.046 | 0.88 | 0.001 |
| CAPG | −0.50 | 0.076 | −0.74 | 0.001 | −0.48 | 0.036 |
| CCDC66 | −0.41 | 0.204 | −0.55 | 0.037 | −0.70 | 0.006 |
| COMMD8 | −0.33 | 0.165 | −0.59 | 0.002 | −0.40 | 0.034 |
| CPD | 0.52 | 0.055 | 0.46 | 0.043 | 0.64 | 0.004 |
| CYB5R1 | −0.25 | 0.327 | −0.51 | 0.011 | −0.72 | 0.000 |
| DUSP6 | −0.45 | 0.129 | −0.61 | 0.013 | −0.48 | 0.049 |
| ENY2 | −0.45 | 0.067 | −0.46 | 0.026 | −0.59 | 0.004 |
| FCER1G | −0.45 | 0.165 | −0.75 | 0.004 | −0.51 | 0.049 |
| FRMD8 | 0.52 | 0.053 | 0.72 | 0.001 | 0.49 | 0.028 |
| GSR | 0.43 | 0.086 | 0.71 | 0.001 | 0.50 | 0.014 |
| KIF1B | 0.45 | 0.092 | 0.59 | 0.007 | 0.57 | 0.008 |
| MEF2D | 0.53 | 0.103 | 0.60 | 0.028 | 0.57 | 0.035 |
| MPZL1 | 0.38 | 0.220 | 0.58 | 0.020 | 0.75 | 0.002 |
| MRPS6 | −0.43 | 0.075 | −0.55 | 0.006 | −0.88 | 0.000 |
| NDUFA5 | −0.25 | 0.247 | −0.60 | 0.000 | −0.36 | 0.037 |
| NDUFB7 | −0.37 | 0.213 | −0.49 | 0.043 | −0.62 | 0.007 |
| NUP153 | 0.34 | 0.228 | 0.57 | 0.009 | 0.62 | 0.005 |

TABLE 6-continued

List of genes significantly (FDR 5%) and differentially (fold-change > 1.5) expressed after incubation of human PBMCs (n = 7) with anti-IL7Ra mAbs compared to unstimulated cells.

| Gene | N13B2-h3VL6 logFC/Unstim | adj.P.Val | MD707-13 IgG4 #1 logFC/Unstim | adj.P.Val | 1A11 IgG1 #2 logFC/Unstim | adj.P.Val |
|---|---|---|---|---|---|---|
| S100A4 | −0.41 | 0.120 | −0.54 | 0.014 | −0.82 | 0.000 |
| S100A8 | −0.38 | 0.266 | −0.56 | 0.043 | −0.77 | 0.004 |
| SERPINA1 | −0.46 | 0.067 | −0.69 | 0.001 | −0.47 | 0.021 |
| SLC17A5 | −0.33 | 0.173 | −0.51 | 0.010 | −0.72 | 0.000 |
| SLC7A7 | −0.47 | 0.076 | −0.68 | 0.002 | −0.52 | 0.016 |
| SNRK-AS1 | 0.59 | 0.079 | 0.57 | 0.042 | 0.59 | 0.031 |
| STAT5A | 0.34 | 0.166 | 0.66 | 0.001 | 0.49 | 0.012 |
| TBXAS1 | −0.27 | 0.390 | −0.49 | 0.043 | −0.64 | 0.007 |
| TFPI2 | −0.52 | 0.079 | −0.65 | 0.008 | −0.49 | 0.042 |
| TMEM184B | 0.22 | 0.545 | 0.63 | 0.013 | 0.55 | 0.027 |
| TYROBP | −0.35 | 0.212 | −0.56 | 0.012 | −0.84 | 0.000 |
| USMG5 | −0.39 | 0.120 | −0.49 | 0.018 | −0.68 | 0.001 |
| USP19 | 0.48 | 0.145 | 0.76 | 0.005 | 0.54 | 0.044 |
| USP38 | 0.44 | 0.105 | 0.49 | 0.029 | 0.61 | 0.006 |
| XYLT2 | 0.27 | 0.329 | 0.60 | 0.005 | 0.57 | 0.006 |
| ACTR5 | 0.56 | 0.137 | 0.74 | 0.018 | 0.53 | 0.093 |
| ADAMDEC1 | −0.88 | 0.095 | −1.24 | 0.004 | −0.63 | 0.176 |
| ARHGAP18 | −0.55 | 0.094 | −0.63 | 0.021 | −0.51 | 0.060 |
| AUH | 1.01 | 0.101 | 1.14 | 0.026 | 0.67 | 0.223 |
| BAG2 | 0.29 | 0.548 | 0.70 | 0.042 | 0.42 | 0.254 |
| BAIAP2 | −0.44 | 0.367 | −0.82 | 0.031 | −0.32 | 0.474 |
| BLOC1S3 | −0.54 | 0.180 | −0.71 | 0.029 | −0.37 | 0.290 |
| C16orf54 | 0.44 | 0.128 | 0.62 | 0.008 | 0.20 | 0.477 |
| C1orf216 | 0.25 | 0.669 | 0.82 | 0.042 | 0.55 | 0.193 |
| C2orf49 | −0.47 | 0.455 | −0.97 | 0.040 | −0.44 | 0.407 |
| C3orf58 | 0.46 | 0.182 | 0.60 | 0.032 | 0.43 | 0.144 |
| CAMK1D | 0.47 | 0.228 | 0.64 | 0.040 | 0.48 | 0.136 |
| CCL2 | −0.33 | 0.522 | −0.86 | 0.019 | 0.52 | 0.186 |
| CCL7 | −0.48 | 0.282 | −0.90 | 0.010 | 0.36 | 0.355 |
| CCRL2 | −0.42 | 0.263 | −0.76 | 0.011 | 0.09 | 0.848 |
| CD33 | −1.08 | 0.261 | −1.61 | 0.039 | −1.28 | 0.103 |
| CD6 | 0.12 | 0.833 | 0.67 | 0.042 | 0.51 | 0.134 |
| CD68 | −0.35 | 0.184 | −0.66 | 0.002 | −0.36 | 0.093 |
| CDC42EP2 | −0.30 | 0.490 | −0.66 | 0.037 | 0.08 | 0.864 |
| CLEC4E | −0.61 | 0.086 | −0.94 | 0.001 | −0.53 | 0.069 |
| CLEC7A | −0.35 | 0.521 | −0.83 | 0.034 | −0.51 | 0.223 |
| CPNE8 | −0.52 | 0.422 | −1.02 | 0.036 | −0.32 | 0.601 |
| CSF3 | 0.03 | 0.959 | −0.63 | 0.030 | 0.30 | 0.353 |
| CTSF | 0.32 | 0.628 | 1.25 | 0.006 | 0.88 | 0.051 |
| DAB2 | −0.62 | 0.089 | −0.67 | 0.029 | −0.49 | 0.119 |
| DFNA5 | −0.63 | 0.080 | −0.89 | 0.002 | −0.33 | 0.311 |
| ECI1 | 0.62 | 0.167 | 0.78 | 0.031 | 0.45 | 0.249 |
| ELAVL1 | 0.56 | 0.120 | 0.74 | 0.013 | 0.51 | 0.091 |
| ERO1L | −0.52 | 0.086 | −0.85 | 0.001 | −0.31 | 0.252 |
| EXOSC4 | −0.51 | 0.130 | −0.69 | 0.013 | −0.23 | 0.491 |
| FAM105A | 0.50 | 0.080 | 0.76 | 0.001 | 0.44 | 0.064 |
| FAM83G | 0.39 | 0.431 | 0.82 | 0.029 | 0.71 | 0.055 |
| FCAR | −0.32 | 0.280 | −0.71 | 0.002 | −0.31 | 0.211 |
| FGR | −0.41 | 0.067 | −0.67 | 0.000 | −0.27 | 0.169 |
| FHL3 | 0.57 | 0.180 | 0.72 | 0.035 | 0.24 | 0.572 |
| FKBP8 | 0.39 | 0.166 | 0.68 | 0.002 | 0.28 | 0.250 |
| FLI1 | 0.63 | 0.053 | 1.03 | 0.000 | 0.51 | 0.065 |
| FPR2 | −0.36 | 0.529 | −0.88 | 0.032 | 0.11 | 0.867 |
| GOS2 | −0.40 | 0.231 | −0.65 | 0.015 | 0.02 | 0.973 |
| GEMIN2 | −0.13 | 0.855 | −0.85 | 0.041 | −0.38 | 0.420 |
| GGH | −0.45 | 0.302 | −0.73 | 0.034 | −0.59 | 0.091 |
| GIMAP1 | 0.39 | 0.256 | 0.69 | 0.012 | 0.47 | 0.097 |
| GIMAP1-GIMAP5 | 1.89 | 0.075 | 1.77 | 0.047 | 0.95 | 0.331 |
| GNG10 | −0.30 | 0.280 | −0.61 | 0.005 | −0.10 | 0.752 |
| GPR137B | −0.51 | 0.376 | −0.90 | 0.044 | −0.31 | 0.566 |
| GPR35 | −0.41 | 0.322 | −0.70 | 0.031 | −0.12 | 0.791 |
| GPR84 | −0.38 | 0.154 | −0.68 | 0.002 | 0.05 | 0.891 |
| GTF2I | 0.85 | 0.101 | 1.11 | 0.009 | 0.75 | 0.082 |
| GZMM | 0.55 | 0.215 | 0.77 | 0.029 | 0.31 | 0.448 |
| HBEGF | −0.57 | 0.080 | −0.76 | 0.004 | 0.02 | 0.970 |
| HECTD3 | 0.61 | 0.107 | 0.66 | 0.038 | 0.38 | 0.267 |
| HLCS | 0.46 | 0.310 | 0.80 | 0.024 | 0.59 | 0.105 |
| IFFO1 | 0.50 | 0.145 | 0.61 | 0.032 | 0.23 | 0.487 |
| IGSF6 | −0.65 | 0.058 | −0.85 | 0.003 | −0.23 | 0.502 |
| IL19 | −0.62 | 0.543 | −1.55 | 0.033 | −0.56 | 0.516 |

TABLE 6-continued

List of genes significantly (FDR 5%) and differentially (fold-change > 1.5) expressed after incubation of human PBMCs (n = 7) with anti-IL7Ra mAbs compared to unstimulated cells.

| Gene | N13B2-h3VL6 | | MD707-13 IgG4 #1 | | 1A11 IgG1 #2 | |
|---|---|---|---|---|---|---|
| | logFC/ Unstim | adj.P.Val | logFC/ Unstim | adj.P.Val | logFC/ Unstim | adj.P.Val |
| IL1R2 | −0.38 | 0.627 | −1.20 | 0.025 | −0.63 | 0.285 |
| IL24 | −0.86 | 0.053 | −0.92 | 0.013 | −0.51 | 0.201 |
| IL6 | −0.43 | 0.196 | −0.68 | 0.012 | 0.14 | 0.701 |
| ILF3-AS1 | −0.50 | 0.263 | −0.76 | 0.035 | −0.26 | 0.542 |
| ISY1-RAB43 | 0.18 | 0.841 | −1.07 | 0.033 | 0.24 | 0.717 |
| JTB | 0.24 | 0.621 | 0.73 | 0.030 | 0.33 | 0.372 |
| KCNA3 | 0.08 | 0.879 | 0.85 | 0.005 | 0.37 | 0.264 |
| KMO | −0.50 | 0.122 | −0.72 | 0.006 | −0.38 | 0.183 |
| LACC1 | −0.40 | 0.071 | −0.65 | 0.000 | −0.27 | 0.171 |
| LILRB3 | −0.31 | 0.410 | −0.67 | 0.017 | 0.12 | 0.763 |
| MET | −0.36 | 0.419 | −0.67 | 0.049 | −0.06 | 0.916 |
| MMP1 | −0.29 | 0.342 | −0.74 | 0.001 | −0.29 | 0.245 |
| MMP19 | −0.34 | 0.254 | −0.59 | 0.013 | −0.32 | 0.204 |
| MTERFD1 | −0.02 | 0.982 | −0.61 | 0.048 | −0.38 | 0.249 |
| NCF1 | −0.48 | 0.214 | −0.85 | 0.006 | −0.39 | 0.241 |
| NCF1C | −0.56 | 0.254 | −1.07 | 0.005 | −0.53 | 0.198 |
| NENF | 0.90 | 0.068 | 0.97 | 0.018 | 0.51 | 0.247 |
| OCEL1 | 0.70 | 0.198 | 1.04 | 0.018 | 0.57 | 0.232 |
| PEX26 | 0.54 | 0.179 | 0.83 | 0.010 | 0.47 | 0.166 |
| PGAM5 | 0.47 | 0.256 | 0.82 | 0.013 | 0.63 | 0.055 |
| PHF1 | 0.08 | 0.883 | 0.65 | 0.043 | 0.38 | 0.270 |
| PIGP | −0.03 | 0.970 | −0.68 | 0.046 | −0.24 | 0.557 |
| PILRA | −0.49 | 0.095 | −0.75 | 0.002 | −0.45 | 0.063 |
| PKIA | 0.57 | 0.256 | 0.86 | 0.034 | 0.54 | 0.211 |
| PLA2G7 | −0.53 | 0.058 | −0.73 | 0.002 | −0.33 | 0.187 |
| PLAUR | −0.32 | 0.229 | −0.68 | 0.001 | −0.21 | 0.363 |
| PMP22 | −0.72 | 0.132 | −1.08 | 0.005 | −0.45 | 0.290 |
| PTAFR | −0.58 | 0.099 | −0.73 | 0.012 | 0.08 | 0.867 |
| QPCT | −0.57 | 0.108 | −0.81 | 0.005 | −0.53 | 0.072 |
| RAB2A | 0.45 | 0.198 | 0.60 | 0.033 | 0.53 | 0.059 |
| RAC1 | 0.90 | 0.065 | 1.13 | 0.005 | 0.76 | 0.063 |
| RALY | 0.39 | 0.234 | 0.60 | 0.023 | 0.44 | 0.107 |
| RANBP10 | 0.14 | 0.738 | 0.59 | 0.026 | 0.31 | 0.293 |
| RASA3 | 0.38 | 0.120 | 0.66 | 0.001 | 0.34 | 0.102 |
| RAVER1 | 0.43 | 0.182 | 0.62 | 0.017 | 0.50 | 0.053 |
| RCN2 | 0.48 | 0.231 | 0.76 | 0.017 | 0.41 | 0.234 |
| RETSAT | 0.48 | 0.231 | 0.65 | 0.047 | 0.59 | 0.065 |
| RSPH3 | −0.13 | 0.841 | −0.95 | 0.008 | −0.29 | 0.497 |
| SEMA4A | −0.53 | 0.057 | −0.69 | 0.003 | −0.04 | 0.911 |
| SEPHS2 | 0.43 | 0.503 | 1.00 | 0.030 | 0.87 | 0.055 |
| SLAMF8 | −0.27 | 0.544 | −0.64 | 0.040 | 0.53 | 0.087 |
| SNAPC1 | −0.34 | 0.325 | −0.64 | 0.016 | −0.30 | 0.300 |
| SUSD3 | 0.53 | 0.101 | 0.59 | 0.027 | 0.41 | 0.136 |
| TAF1A | −0.23 | 0.588 | −0.60 | 0.043 | −0.03 | 0.954 |
| TBC1D17 | 0.37 | 0.330 | 0.65 | 0.029 | 0.38 | 0.227 |
| TBC1D22A | 0.38 | 0.254 | 0.62 | 0.020 | 0.23 | 0.469 |
| TBC1D25 | 0.37 | 0.298 | 0.71 | 0.010 | 0.44 | 0.120 |
| TBL2 | 0.31 | 0.450 | 0.68 | 0.026 | 0.23 | 0.542 |
| TFE3 | 0.23 | 0.552 | 0.61 | 0.027 | 0.41 | 0.159 |
| THBS1 | −0.37 | 0.256 | −0.64 | 0.012 | −0.49 | 0.053 |
| TLR8 | −0.74 | 0.089 | −0.88 | 0.015 | −0.03 | 0.963 |
| TMEM176B | −0.94 | 0.068 | −1.03 | 0.016 | −0.82 | 0.055 |
| TPRKB | −0.46 | 0.212 | −0.88 | 0.003 | −0.48 | 0.120 |
| UBE3A | 0.06 | 0.924 | 0.65 | 0.042 | 0.54 | 0.096 |
| USP21 | 0.37 | 0.272 | 0.75 | 0.004 | 0.27 | 0.363 |
| VAMP4 | −0.31 | 0.375 | −0.61 | 0.024 | −0.40 | 0.163 |
| VNN2 | −0.47 | 0.086 | −0.60 | 0.008 | −0.41 | 0.074 |
| WBP5 | −0.97 | 0.205 | −1.42 | 0.020 | −0.70 | 0.298 |
| XPOT | 0.78 | 0.061 | 0.78 | 0.026 | 0.57 | 0.108 |
| ZDHHC3 | 0.56 | 0.095 | 0.73 | 0.008 | 0.30 | 0.328 |
| ZER1 | 0.58 | 0.161 | 0.78 | 0.019 | 0.36 | 0.333 |
| ZNF589 | 0.27 | 0.504 | 0.73 | 0.012 | 0.25 | 0.474 |
| ZNF71 | 0.55 | 0.101 | 0.65 | 0.020 | 0.23 | 0.487 |
| ZNF792 | 0.70 | 0.108 | 0.95 | 0.008 | 0.67 | 0.063 |
| ABHD14A | −0.24 | 0.527 | 0.00 | 1.000 | −0.62 | 0.018 |
| ACSL1 | 0.07 | 0.872 | −0.08 | 0.823 | 0.62 | 0.014 |
| AGO2 | 0.21 | 0.547 | 0.31 | 0.259 | 0.71 | 0.003 |
| APOBEC3D | 0.20 | 0.673 | 0.12 | 0.801 | 0.68 | 0.034 |
| ARHGAP31 | 0.22 | 0.582 | 0.28 | 0.364 | 0.60 | 0.026 |
| ATF3 | 0.18 | 0.771 | 0.04 | 0.949 | 0.89 | 0.017 |
| B3GNT5 | 0.11 | 0.855 | −0.01 | 0.985 | 0.81 | 0.013 |

TABLE 6-continued

List of genes significantly (FDR 5%) and differentially (fold-change > 1.5) expressed after incubation of human PBMCs (n = 7) with anti-IL7Ra mAbs compared to unstimulated cells.

| Gene | N13B2-h3VL6 | | MD707-13 IgG4 #1 | | 1A11 IgG1 #2 | |
|---|---|---|---|---|---|---|
| | logFC/ Unstim | adj.P.Val | logFC/ Unstim | adj.P.Val | logFC/ Unstim | adj.P.Val |
| BACH2 | 0.26 | 0.352 | 0.25 | 0.296 | 0.71 | 0.001 |
| C19orf43 | −0.57 | 0.055 | −0.30 | 0.285 | −0.59 | 0.014 |
| C9orf69 | 0.34 | 0.319 | 0.40 | 0.153 | 0.64 | 0.012 |
| CCL4 | −0.15 | 0.757 | −0.39 | 0.248 | 0.94 | 0.002 |
| CCL8 | −0.28 | 0.813 | −0.94 | 0.214 | 2.02 | 0.003 |
| CCR2 | −0.56 | 0.174 | −0.32 | 0.412 | −1.00 | 0.002 |
| CD160 | −0.64 | 0.288 | −0.74 | 0.143 | 2.02 | 0.000 |
| CD274 | −0.28 | 0.494 | −0.36 | 0.285 | 0.78 | 0.008 |
| CD36 | −0.77 | 0.172 | −0.72 | 0.129 | −1.26 | 0.005 |
| CD52 | −0.08 | 0.769 | −0.25 | 0.155 | −0.61 | 0.000 |
| CD69 | 0.02 | 0.974 | −0.08 | 0.770 | 0.82 | 0.000 |
| CD72 | −0.30 | 0.499 | −0.29 | 0.431 | 0.65 | 0.038 |
| CHKA | −0.41 | 0.410 | −0.56 | 0.156 | −0.76 | 0.039 |
| CLIC3 | 0.05 | 0.939 | −0.05 | 0.913 | −0.67 | 0.041 |
| COMMD3-BMI1 | 0.34 | 0.655 | 0.21 | 0.771 | −1.41 | 0.005 |
| COX17 | −0.21 | 0.616 | −0.45 | 0.133 | −0.67 | 0.015 |
| CRTAM | −0.39 | 0.388 | −0.39 | 0.310 | 1.05 | 0.002 |
| CSF2 | 0.11 | 0.939 | 0.79 | 0.337 | 1.61 | 0.024 |
| CSF2RB | 0.04 | 0.930 | 0.01 | 0.989 | 0.73 | 0.004 |
| CX3CR1 | −0.19 | 0.662 | −0.24 | 0.493 | −0.64 | 0.023 |
| CXCL10 | −0.55 | 0.511 | −0.36 | 0.648 | 1.58 | 0.007 |
| CXCL9 | −0.32 | 0.687 | −0.05 | 0.956 | 1.61 | 0.002 |
| DUSPI | 0.85 | 0.133 | 0.82 | 0.088 | 0.93 | 0.043 |
| DVL2 | 0.54 | 0.143 | 0.58 | 0.058 | 0.61 | 0.040 |
| EGR2 | −0.67 | 0.094 | −0.45 | 0.210 | 0.85 | 0.008 |
| EIF4EBP1 | −0.46 | 0.260 | −0.15 | 0.737 | −0.81 | 0.010 |
| EPSTI1 | 0.09 | 0.874 | 0.16 | 0.728 | 0.75 | 0.021 |
| FAM91A1 | 0.35 | 0.338 | 0.50 | 0.083 | 0.59 | 0.034 |
| FASLG | 0.05 | 0.933 | 0.06 | 0.881 | 0.76 | 0.007 |
| FBXO30 | 0.27 | 0.586 | 0.63 | 0.077 | 0.76 | 0.024 |
| FGFBP2 | −0.16 | 0.647 | −0.23 | 0.384 | −0.77 | 0.001 |
| FUS | 0.30 | 0.429 | 0.37 | 0.238 | 0.61 | 0.029 |
| GBP1 | −0.22 | 0.716 | −0.34 | 0.475 | 1.07 | 0.005 |
| GBP1P1 | −0.19 | 0.820 | −0.02 | 0.979 | 1.11 | 0.019 |
| GBP2 | 0.04 | 0.924 | 0.02 | 0.956 | 0.61 | 0.004 |
| GBP4 | 0.00 | 0.997 | 0.08 | 0.823 | 0.74 | 0.002 |
| GBP5 | 0.00 | 1.000 | 0.06 | 0.921 | 1.14 | 0.002 |
| GCHFR | −0.03 | 0.952 | −0.16 | 0.574 | −0.64 | 0.004 |
| GIMAP8 | 0.37 | 0.298 | 0.49 | 0.092 | 0.59 | 0.035 |
| GZMA | −0.28 | 0.298 | −0.29 | 0.194 | −0.61 | 0.003 |
| GZMB | 0.05 | 0.916 | −0.08 | 0.829 | 0.71 | 0.002 |
| GZMH | −0.23 | 0.512 | −0.36 | 0.181 | −0.68 | 0.005 |
| HAVCR2 | 0.07 | 0.858 | −0.19 | 0.435 | 0.66 | 0.001 |
| HIST1H2BK | −0.29 | 0.391 | −0.47 | 0.076 | −0.71 | 0.005 |
| HIVEPI | 0.36 | 0.213 | 0.09 | 0.783 | 0.65 | 0.005 |
| HSPBP1 | 0.53 | 0.153 | 0.49 | 0.120 | 0.78 | 0.007 |
| HSPH1 | 0.40 | 0.414 | 0.71 | 0.056 | 0.72 | 0.046 |
| IFNG | 0.32 | 0.706 | −0.32 | 0.654 | 1.21 | 0.024 |
| IGF2R | 0.15 | 0.664 | 0.37 | 0.119 | 0.66 | 0.003 |
| IKZF2 | 0.20 | 0.664 | 0.42 | 0.212 | 0.61 | 0.049 |
| IL21R-AS1 | 0.16 | 0.635 | 0.34 | 0.172 | 0.61 | 0.007 |
| INADL | 0.56 | 0.070 | 0.45 | 0.088 | 0.59 | 0.018 |
| INHBA | −0.08 | 0.885 | −0.24 | 0.549 | 0.89 | 0.005 |
| INIP | −0.50 | 0.067 | −0.38 | 0.111 | −0.59 | 0.008 |
| INTS3 | 0.55 | 0.092 | 0.49 | 0.079 | 0.67 | 0.010 |
| IRF1 | 0.01 | 0.996 | 0.13 | 0.727 | 0.68 | 0.013 |
| IRF4 | 0.36 | 0.256 | 0.41 | 0.113 | 1.03 | 0.000 |
| IRF8 | −0.09 | 0.790 | 0.01 | 0.982 | 0.71 | 0.000 |
| IRG1 | −0.36 | 0.567 | −0.45 | 0.380 | 1.41 | 0.002 |
| ISOC2 | 0.30 | 0.564 | 0.07 | 0.898 | 0.74 | 0.036 |
| JAK2 | 0.63 | 0.087 | 0.53 | 0.091 | 0.98 | 0.001 |
| JUN | 0.06 | 0.880 | 0.23 | 0.400 | 0.76 | 0.002 |
| KCNK6 | 0.37 | 0.503 | 0.60 | 0.144 | 0.80 | 0.040 |
| KDM6B | −0.05 | 0.911 | 0.19 | 0.527 | 0.66 | 0.006 |
| KHK | −0.81 | 0.070 | −0.17 | 0.733 | −0.73 | 0.047 |
| KIR2DL4 | −0.26 | 0.656 | −0.39 | 0.402 | 1.02 | 0.008 |
| KLRB1 | −0.13 | 0.622 | −0.26 | 0.178 | −0.82 | 0.000 |
| LGALS1 | −0.42 | 0.178 | −0.49 | 0.052 | −0.69 | 0.005 |
| LIMK2 | −0.08 | 0.879 | −0.01 | 0.976 | 0.79 | 0.006 |
| LMNB1 | 0.13 | 0.793 | 0.30 | 0.418 | 0.72 | 0.018 |

TABLE 6-continued

List of genes significantly (FDR 5%) and differentially (fold-change > 1.5) expressed after incubation of human PBMCs (n = 7) with anti-IL7Ra mAbs compared to unstimulated cells.

| Gene | N13B2-h3VL6 logFC/Unstim | adj.P.Val | MD707-13 IgG4 #1 logFC/Unstim | adj.P.Val | 1A11 IgG1 #2 logFC/Unstim | adj.P.Val |
|---|---|---|---|---|---|---|
| LOC729013 | −0.42 | 0.503 | −0.39 | 0.469 | −0.93 | 0.035 |
| LRCH4 | 0.72 | 0.170 | 0.74 | 0.087 | 0.89 | 0.033 |
| LST1 | −0.45 | 0.432 | −0.83 | 0.055 | −1.03 | 0.013 |
| MAP3K13 | −0.09 | 0.837 | −0.38 | 0.125 | −0.64 | 0.006 |
| MB21D1 | 0.00 | 1.000 | 0.15 | 0.701 | 0.76 | 0.009 |
| MFGE8 | 0.08 | 0.941 | 0.21 | 0.792 | −1.17 | 0.034 |
| MPPE1 | −0.31 | 0.477 | −0.43 | 0.220 | −0.77 | 0.013 |
| NAB2 | 0.25 | 0.731 | 0.55 | 0.278 | 1.23 | 0.006 |
| NDUFAF6 | −0.27 | 0.557 | −0.54 | 0.115 | −0.65 | 0.044 |
| NFKBIB | 0.08 | 0.881 | 0.21 | 0.576 | 0.60 | 0.043 |
| NOP14 | 0.14 | 0.821 | 0.55 | 0.164 | 0.80 | 0.028 |
| NR4A1 | 0.12 | 0.777 | 0.06 | 0.871 | 0.95 | 0.000 |
| NR4A2 | −0.09 | 0.841 | −0.25 | 0.373 | 0.75 | 0.002 |
| OSBPL5 | −0.55 | 0.152 | −0.21 | 0.581 | −0.62 | 0.046 |
| PAGR1 | 0.48 | 0.159 | 0.54 | 0.051 | 0.64 | 0.016 |
| PIM3 | 0.05 | 0.930 | 0.42 | 0.181 | 0.59 | 0.040 |
| PLEK | −0.08 | 0.853 | −0.17 | 0.579 | 0.82 | 0.001 |
| PML | 0.51 | 0.168 | 0.56 | 0.067 | 0.62 | 0.036 |
| PPP1R15B | 0.27 | 0.302 | 0.32 | 0.143 | 0.60 | 0.003 |
| PTGES2 | −0.39 | 0.545 | −0.64 | 0.189 | −1.00 | 0.026 |
| PTGS2 | 0.12 | 0.854 | −0.02 | 0.971 | 0.79 | 0.022 |
| PYCARD | −0.16 | 0.703 | −0.21 | 0.550 | −0.60 | 0.032 |
| RAB20 | −0.28 | 0.509 | −0.34 | 0.324 | 0.61 | 0.045 |
| RGS16 | −0.16 | 0.809 | −0.07 | 0.901 | 1.09 | 0.004 |
| RNF19A | 0.22 | 0.457 | 0.26 | 0.282 | 0.67 | 0.002 |
| RPL21 | −0.54 | 0.132 | −0.10 | 0.809 | −0.84 | 0.004 |
| RPL34 | −0.07 | 0.837 | −0.10 | 0.709 | −0.59 | 0.003 |
| RPS29 | −0.02 | 0.975 | −0.06 | 0.878 | −0.60 | 0.024 |
| SBNO2 | 0.14 | 0.758 | 0.23 | 0.515 | 0.59 | 0.044 |
| SERPINE2 | −0.19 | 0.655 | 0.02 | 0.957 | 0.63 | 0.026 |
| SH2D1B | −0.11 | 0.749 | −0.09 | 0.742 | 0.94 | 0.000 |
| SH3BGRL3 | −0.28 | 0.207 | −0.26 | 0.180 | −0.66 | 0.000 |
| SLC25A20 | −0.14 | 0.731 | −0.33 | 0.257 | −0.59 | 0.024 |
| SLC7A5 | 0.33 | 0.355 | 0.21 | 0.530 | 0.0 | 0.024 |
| SLMO2-ATP5E | −0.30 | 0.893 | −0.82 | 0.594 | −2.45 | 0.042 |
| SMG6 | 0.30 | 0.410 | 0.45 | 0.121 | 0.62 | 0.021 |
| SMIM11 | −0.40 | 0.417 | −0.43 | 0.299 | −0.74 | 0.045 |
| SMIM14 | −0.32 | 0.165 | −0.36 | 0.057 | −0.68 | 0.000 |
| SNHG8 | −0.25 | 0.666 | −0.37 | 0.400 | −0.80 | 0.034 |
| SPRY2 | −0.16 | 0.880 | −0.46 | 0.531 | 1.37 | 0.018 |
| SRC | 0.25 | 0.549 | 0.32 | 0.341 | 0.59 | 0.042 |
| SREBF1 | 0.41 | 0.509 | 0.58 | 0.233 | 0.93 | 0.034 |
| STARD4 | 0.21 | 0.583 | 0.33 | 0.268 | 0.83 | 0.002 |
| STAT1 | 0.20 | 0.582 | 0.23 | 0.428 | 0.64 | 0.008 |
| SUMF1 | −0.17 | 0.683 | −0.37 | 0.222 | −0.64 | 0.017 |
| TAGAP | 0.03 | 0.937 | 0.08 | 0.793 | 1.06 | 0.000 |
| TESK1 | −0.06 | 0.921 | 0.18 | 0.645 | 0.63 | 0.038 |
| TMEM165 | 0.42 | 0.303 | 0.57 | 0.083 | 0.65 | 0.038 |
| TNF | −0.33 | 0.261 | −0.32 | 0.206 | 0.61 | 0.007 |
| TNFRSF10A | 0.34 | 0.619 | 0.63 | 0.215 | 0.93 | 0.044 |
| TNFRSF9 | 0.02 | 0.976 | −0.09 | 0.807 | 1.08 | 0.000 |
| TP53I13 | 0.53 | 0.210 | 0.62 | 0.073 | 0.84 | 0.010 |
| TYSND1 | −0.24 | 0.590 | −0.10 | 0.818 | −0.70 | 0.018 |
| UBE2D1 | 0.63 | 0.111 | 0.62 | 0.066 | 0.91 | 0.005 |
| XCL1 | −0.07 | 0.941 | 0.02 | 0.979 | 2.19 | 0.000 |
| XCL2 | −0.25 | 0.805 | 0.77 | 0.257 | 2.83 | 0.000 |
| ZNF326 | −0.37 | 0.344 | −0.53 | 0.088 | −0.60 | 0.044 |

Venn diagram (FIG. 11C) analysis identified 61 common differentially expressed genes with the three mAbs without any particular GoMiner gene ontology enrichment. Despite 61 common genes, the antibody of the invention induces only 31 significant gene modifications without gene ontology enrichment. In contrast, the two antibodies of prior art induce an important transcriptional modification of human PBMCs transcriptome, with 245 differentially expressed genes induced by the site-1 IgG4 #1 mAb and 237 differentially expressed genes induced by the site-1 IgG1 #2 mAb. 78 differentially expressed genes were common between these two site-1 mAbs, but these genes are not differentially expressed when the PBMCs are stimulated with N13B2-hVL6.

Principal Component Analysis (PCA) of the IL-7 signature shows that the differentially expressed genes induced by the antibodies of the prior art are strongly different from the differentially expressed genes induced by IL-7. GoMiner gene ontology enrichment suggests that both antibodies of the prior art modify biological PBMCs functions such as leukocyte activation, proliferation, migration, chemotaxis, cytokine secretion and inflammatory responses associated with the MAPK/ERK pathway.

Among the 334 genes differentially expressed with IL7 compared to the control condition, 93 genes were differentially expressed with a high fold-change (>2) and were separated into 3 distinct clusters by heat-map analysis (FIG. 11A). The first cluster of downregulated genes assessed by gene ontology enrichment were mainly implicated in leukocyte differentiation and apoptosis, a second cluster of highly upregulated genes were associated with leukocyte adhesion, differentiation and activation, and a third cluster of upregulated gene had mixed gene ontology. Interestingly, all tested mAbs (both site-1 or site-1/2b) exhibited similar effects by preventing cluster-1 and cluster-2 modification but without impact on cluster-3 (FIG. 11B).

Altogether, transcriptional analyses confirmed that despite site-1 and site-1/2b anti-human IL-7Rα mAbs shared similar antagonist properties, the two site-1 mAbs described in the state of the art induced significant transcriptional modifications of human PBMCs compatible with T-cell activation and inflammatory responses induced by the MAPK/ERK pathway.

The site-1/2b anti-human IL-7Rα mAb of the invention, i.e. N13B2-hVL6, induced less transcriptional modification of human PBMCs compared to the two site-1 mAbs described in the state of the art.

The lack of specific and "antagonist-only" anti-IL-7Rα mAbs for larger species has prevented verification of this effect in primates or humans. The inventors found that the agonist/antagonist properties of anti-IL-7Rα mAbs depends on the specific epitope targeted, since antibodies of the state of the art binding the site-1 IL-7 interaction domain appear to have both agonist/antagonist properties whereas the antibody of the invention binding the dimerization domain of IL-7Rα/γc (site 2b) display strict antagonist activity. The inventors suggest that the antibody of the invention could perturb IL-7Rα/γc dimerization required for receptor internalization and signaling. "Antagonist-only" antibodies against the IL-7R prevented long-term memory T-cell-mediated skin inflammation in primates, even after chronic antigen stimulation, without inducing lymphopenia or polyclonal T-cell functional or metabolic deficiencies.

IL-7 has been shown to induce proliferative and anti-apoptotic signals through IL-7R signaling mainly by activating the JAK/STAT pathway. IL-7R signaling is also believed to involve the PI3K/AKT pathway, but this has been observed in transformed immortalized cell lines or primary thymocytes and these signals were not detectable in peripheral naïve or memory human T lymphocytes (Watanabe, J. Exp. Med, 1998). Several reports have also suggested that IL-7R signaling could amplify ERK phosphorylation either in T lymphocytes or pro-B cell subsets (Deshpande P. I. Immunol, 2013; Fleming H E and Paige C J, Immunity, 2001). The role of these pathways in IL-7R signaling in mature and human T cells is less clear. Using primary freshly isolated human PBMCs (mostly composed of T and B lymphocytes, monocytes and NK cells) from healthy volunteers stimulated with a high concentration of recombinant human IL-7 (5000 pg/ml, while the concentration in sera is ~5 pg/ml in non-lymphopenic conditions Wong H-L, Cancer Epidemiol Biomarkers Prev, 2008)), the inventors confirmed that IL-7 induced reproducible STAT5 phosphorylation. PI3K signal activation was more variable, and they did not observe any ERK phosphorylation. While all anti-IL7Ra mAbs used in this study were potent inhibitors of IL-7-induced pSTAT5 and displayed similar transcriptional antagonist properties, we found that two site-1 mAbs of the state of the art induced PI3K/ERK agonist signals and important transcriptional modifications associated with T-cell activation and inflammatory responses induced by the MAPK/ERK pathway. These opposing dual agonist/antagonist properties of some mAbs are not unique since other targets such as IL-4, IL-6R, IL-15, CD28, CD38, CD40, or HER2 demonstrated similar activities after receptor endocytosis/internalization.

The heterodimerization of this site 2b with TSLPR has also been recently confirmed and demonstrated to be poised for receptor signaling as already predicted for IL-7Rα and the γ-chain (Verstraete K., Nature Communications, 2017). Interestingly, the predicted heterodimerization site between IL-7Rα/γ-chain and IL-7Rα/TSLPR is overlapping suggesting a shared heterodimerization-mediated signaling mechanism between both receptors.

We found that the in vitro pSTAT5 inhibition assay was not predictive of anti-IL-7R antibody efficacy in vivo. In a previous report, another anti-IL7Ra mAb prevented in vitro and ex vivo IL-7-induced pSTAT5 in primates but did not protect from brain inflammation in an experimental autoimmune encephalitis (EAE) marmoset model (Dunham J., J. Neuroimmune.Pharmacol, 2016).

IL-7 has been well-described in maintaining the pool of peripheral naïve and memory T lymphocytes in mice. In primates however, the importance of IL-7 in maintaining peripheral T-cell homeostasis might therefore be less evident and/or redundant mechanisms might explain the difference between species.

These data showed that antagonist properties of anti-IL-7Rα mAbs and in-vivo efficacy are not only related to the prevention of IL-7 binding and pSTAT5 inhibition. These data showed that the antibody of the invention also targeting the receptor heterodimerization site (site 2b), is "antagonist-only" and result in a higher efficacy of inhibitory T cell responses in vivo.

Targeting IL7R with "antagonist-only" antibodies has the potential to regulate antigen-specific memory T cell survival and accumulation, and therefore might promote the prevention of long-term relapse in autoimmune and inflammatory diseases.

REFERENCES

Abraham, C. & Cho, J. H. Inflammatory Bowel Disease. New England Journal of Medicine 361, 2066-2078 (2009).
Adams, D. H. & Eksteen, B. Aberrant homing of mucosal T cells and extra-intestinal manifestations of inflammatory bowel disease. Nat. Rev. Immunol. 6, 244-251 (2006).
Agace, W. W. Tissue-tropic effector T cells: generation and targeting opportunities. Nat. Rev. Immunol. 6, 682-692 (2006).
Albuquerque A S, Cortesão C S, Foxall R B, Soares R S, Victorino R M, Sousa A E. Rate of increase in circulating IL-7 and loss of IL-7Ralpha expression differ in HIV-1 and HIV-2 infections: two lymphopenic diseases with similar hyperimmune activation but distinct outcomes. J Immunol. 2007 Mar. 1; 178(5):3252-9. PubMed PMID: 17312174.
Baumgart, D. C. & Sandborn, W. J. Crohn's disease. Lancet 380, 1590-1605 (2012).
Broux, B., Hellings, N., Venken, K., Rummens, J.-L., Hensen, K., Van Wijmeersch, B., and Stinissen, P. (2010). Haplotype 4 of the multiple sclerosis-associated interleukin-7 receptor alpha gene influences the frequency of recent thymic emigrants. Genes Immun. 11, 326-333.

Chothia, C., and Lesk, A. M. (1987). Canonical structures for the hypervariable regions of immunoglobulins. J. Mol. Biol. 196, 901-917.

Chothia C, Lesk A M, Gherardi E, Tomlinson I M, Walter G, Marks J D, Llewelyn M B, Winter G. Structural repertoire of the human V H segments. J Mol Biol. 1992 Oct. 5; 227(3):799-817.

Clark L A, Demarest S J, Eldredge J, Jarpe M B, Li Y, Simon K, van Vlijmen H W. Influence of canonical structure determining residues on antibody affinity and stability. J Struct Biol. 2014 February; 185(2):223-7. doi: 10.1016/j.jsb.2013.08.009. PubMed PMID: 23994046

Danese, S. & Fiocchi, C. Ulcerative colitis. N. Engl. J. Med. 365, 1713-1725 (2011).

Denucci, C. C., Mitchell, J. S., and Shimizu, Y. (2009). Integrin function in T-cell homing to lymphoid and non-lymphoid sites: getting there and staying there. Crit. Rev. Immunol. 29, 87-109.

Feagan, B. G. et al. Vedolizumab as Induction and Maintenance Therapy for Ulcerative Colitis. New England Journal of Medicine 369, 699-710 (2013).

Deshpande, P., Cavanagh, M. M., Le Saux, S., Singh, K., Weyand, C. M., and Goronzy, J. J. (2013). IL-7— and IL-15— mediated TCR sensitization enables T cell responses to self-antigens. J. Immunol. Baltim. Md 1950 190, 1416-1423.

Dunham, J., Lee, L.-F., Driel, N. van, Laman, J. D., Ni, I., Zhai, W., Tu, G.-H., Lin, J. C., Bauer, J., Hart, B. A. 't, et al. (2016). Blockade of CD127 Exerts a Dichotomous Clinical Effect in Marmoset Experimental Autoimmune Encephalomyelitis. J. Neuroimmune Pharmacol. 11, 73-83.

Fleming, H. E., and Paige, C. J. (2001). Pre-B Cell Receptor Signaling Mediates Selective Response to IL-7 at the Pro-B to Pre-B Cell Transition via an ERK/MAP Kinase-Dependent Pathway. Immunity 15, 521-531.

Gorfu, G., Rivera-Nieves, J., and Ley, K. (2009). Role of beta7 integrins in intestinal lymphocyte homing and retention. Curr. Mol. Med. 9, 836-850.

Haas, J., Korporal, M., Schwarz, A., Balint, B., and Wildemann, B. (2011). The interleukin-7 receptor a chain contributes to altered homeostasis of regulatory T cells in multiple sclerosis. Eur. J. Immunol. 41, 845-853.

Haudebourg, T., Poirier, N., and Vanhove, B. (2009). Depleting T-cell subpopulations in organ transplantation. Transpl. Int. Off. J. Eur. Soc. Organ Transplant. 22, 509-518.

He, R., and Geha, R. S. (2010). Thymic stromal lymphopoietin. Ann. N. Y. Acad. Sci. 1183, 13-24.

Henriques, C. M., Rino, J., Nibbs, R. J., Graham, G. J., and Barata, J. T. (2010). IL-7 induces rapid clathrin-mediated internalization and JAK3-dependent degradation of IL-7Ralpha in T cells. Blood 115, 3269-3277.

Kabat, E. A., Wu, T. T., Reid-Miller, M., Perry, H. M. and Gottesman, K. S. (1992) Sequences of Proteins of Immunological Interest (DIANE publishing, 1992).

Kern, B., Kraynov, E., Lee, L.-F., Ray, R. (2013). Receptor occupancy and internalization of an anti-IL-7 receptor antibody. Cytokine 63, 276-277.

Kern B, Li W, Bono C, Lee L F, Kraynov E. Receptor occupancy and blocking of STAT5 signaling by an anti-IL-7 receptor a antibody in cynomolgus monkeys. Cytometry B Clin Cytom. 2016 March; 90(2):191-8.

Khor, B., Gardet, A. & Xavier, R. J. Genetics and pathogenesis of inflammatory bowel disease. Nature 474, 307-317 (2011).

Lei, L., Zhang, Y., Yao, W., Kaplan, M. H., and Zhou, B. (2011). Thymic Stromal Lymphopoietin Interferes with Airway Tolerance by Suppressing the Generation of Antigen-Specific Regulatory T Cells. J. Immunol. 186, 2254-2261.

Mazzucchelli, R., Hixon, J. A., Spolski, R., Chen, X., Li, W. Q., Hall, V. L., Willette-Brown, J., Hurwitz, A. A., Leonard, W. J., and Durum, S. K. (2008). Development of regulatory T cells requires IL-7Ralpha stimulation by IL-7 or TSLP. Blood 112, 3283-3292.

McElroy C A, Dohm J A, Walsh S T. Structural and biophysical studies of the human IL-7/IL-7Ralpha complex. Structure. 2009 Jan. 14; 17(1):54-65. doi: 10.1016/j.str.2008.10.019.

McElroy C A, Holland P J, Zhao P, Lim J M, Wells L, Eisenstein E, Walsh S T. Structural reorganization of the interleukin-7 signaling complex. Proc Natl Acad Sci USA. 2012 Feb. 14; 109(7):2503-8. doi: 10.1073/pnas.1116582109

Michel, L., Berthelot, L., Pettré, S., Wiertlewski, S., Lefrère, F., Braudeau, C., Brouard, S., Soulillou, J.-P., and Laplaud, D.-A. (2008). Patients with relapsing-remitting multiple sclerosis have normal Treg function when cells expressing IL-7 receptor alpha-chain are excluded from the analysis. J. Clin. Invest. 118, 3411-3419.

Planell N, Lozano J J, Mora-Buch R, Masamunt M C, Jimeno M, Ordás I, Esteller M, Ricart E, Piqué J M, Panés J, Salas A. Transcriptional analysis of the intestinal mucosa of patients with ulcerative colitis in remission reveals lasting epithelial cell alterations. Gut. 2013 July; 62(7):967-76. doi: 10.1136/gutjnl-2012-303333

Racapé, M., Vanhove, B., Soulillou, J.-P., and Brouard, S. (2009). Interleukin 7 receptor alpha as a potential therapeutic target in transplantation. Arch. Immunol. Ther. Exp. (Warsz.) 57, 253-261.

Reche P A, Soumelis V, Gorman D M, Clifford T, Liu Mr, Travis M, Zurawski S M, Johnston J, Liu Y J, Spits H, de Waal Malefyt R, Kastelein R A, Bazan J F. Human thymic stromal lymphopoietin preferentially stimulates myeloid cells. J Immunol. 2001 Jul. 1; 167(1):336-43

Roan, F., Bell, B. D., Stoklasek, T. A., Kitajima, M., Han, H., and Ziegler, S. F. (2012). The multiple facets of thymic stromal lymphopoietin (TSLP) during allergic inflammation and beyond. J. Leukoc. Biol. 91, 877-886.

Rochman, Y., Kashyap, M., Robinson, G. W., Sakamoto, K., Gomez-Rodriguez, J., Wagner, K.-U., and Leonard, W. J. (2010). Thymic stromal lymphopoietin-mediated STAT5 phosphorylation via kinases JAK1 and JAK2 reveals a key difference from IL-7-induced signaling. Proc. Natl. Acad. Sci. U.S.A 107, 19455-19460.

Sandborn, W. J. et al. Vedolizumab as Induction and Maintenance Therapy for Crohn's Disease. New England Journal of Medicine 369, 711-721 (2013).

Shochat C, Tal N, Bandapalli O R, Palmi C, Ganmore I, to Kronnie G, Cario G, Cazzaniga G, Kulozik A E, Stanulla M, Schrappe M, Biondi A, Basso G, Bercovich D, Muckenthaler M U, Izraeli S. Gain-of-function mutations in interleukin-7 receptor-α (IL7R) in childhood acute lymphoblastic leukemias. J Exp Med. 2011 May 9;208(5): 901-8. doi: 10.1084/jem.20110580. Erratum in: J Exp Med. 2011 May 9; 208(5):preceding 901. J Exp Med. 2011 Jun. 6; 208(6):1333

Taylor, B. C., Zaph, C., Troy, A. E., Du, Y., Guild, K. J., Comeau, M. R., and Artis, D. (2009). TSLP regulates intestinal immunity and inflammation in mouse models of helminth infection and colitis. J. Exp. Med. 206, 655-667.

Van Bodegom, D., Zhong, J., Kopp, N., Dutta, C., Kim, M.-S., Bird, L., Weigert, O., Tyner, J., Pandey, A., Yoda, A., et al. (2012). Differences in signaling through the B-cell leukemia oncoprotein CRLF2 in response to TSLP and through mutant JAK2. Blood 120, 2853-2863.

Verstraete, K., Peelman, F., Braun, H., Lopez, J., Van Rompaey, D., Dansercoer, A., Vandenberghe, I., Pauwels, K., Tavernier, J., Lambrecht, B. N., et al. (2017). Structure and antagonism of the receptor complex mediated by human TSLP in allergy and asthma. Nat. Commun. 8.

Walsh S T. Structural insights into the common γ-chain family of cytokines and receptors from the interleukin-7 pathway. Immunol Rev. 2012 November; 250(1):303-16

Watanabe, M., Ueno, Y., Yajima, T., Okamoto, S., Hayashi, T., Yamazaki, M., Iwao, Y., Ishii, H., Habu, S., Uehira, M., et al. (1998). Interleukin 7 transgenic mice develop chronic colitis with decreased interleukin 7 protein accumulation in the colonic mucosa. J. Exp. Med. 187, 389-402.

Watanabe, N., Wang, Y.-H., Lee, H. K., Ito, T., Wang, Y.-H., Cao, W., and Liu, Y.-J. (2005a). Hassall's corpuscles instruct dendritic cells to induce CD4+CD25+ regulatory T cells in human thymus. Nature 436, 1181-1185.

Wong, H.-L., Pfeiffer, R. M., Fears, T. R., Vermeulen, R., Ji, S., and Rabkin, C. S. (2008). Reproducibility Ying, S., O'Connor, B., Ratoff, J., Meng, Q., Fang, C., Cousins, D., Zhang, G., Gu, S., Gao, Z., Shamji, B., et al. (2008). Expression and cellular provenance of thymic stromal lymphopoietin and chemokines in patients with severe asthma and chronic obstructive pulmonary disease. J. Immunol. Baltim. Md 1950 181, 2790-2798.

Zhi, K., Li, M., Zhang, X., Gao, Z., Bai, J., Wu, Y., Zhou, S., Li, M., and Qu, L. (2014). α4β7 Integrin (LPAM-1) is upregulated at atherosclerotic lesions and is involved in atherosclerosis progression. Cell. Physiol. Biochem. Int. J. Exp. Cell. Physiol. Biochem. Pharmacol. 33, 1876-1887

Zhong, J., Sharma, J., Raju, R., Palapetta, S. M., Prasad, T. S. K., Huang, T.-C., Yoda, A., Tyner, J. W., van Bodegom, D., Weinstock, D. M., et al. (2014). TSLP signaling pathway map: a platform for analysis of TSLP-mediated signaling. Database J. Biol. Databases Curation 2014, bau007.

What is claimed is:

1. A method of inhibiting inflammation associated with the interleukin-7 (IL-7) signaling pathway, the method comprising administering an effective amount of a composition comprising an anti-human CD127 agent to a patient in need thereof, wherein said anti-human CD127 agent comprises an antibody or an antigen-binding fragment thereof comprising:
    an antibody light chain comprising or an antibody light chain variable domain consisting of a sequence selected from the group consisting of SEQ ID NO: 9, SEQ ID NO: 10, SEQ ID NO: 11, and SEQ ID NO: 12; and
    an antibody heavy chain comprising or an antibody heavy chain variable domain consisting of the sequence set forth in SEQ ID NO: 7;
    wherein said antibody or an antigen binding fragment thereof specifically binds to CD127.

2. The method of inhibiting inflammation according to claim 1, wherein the inflammation associated with the interleukin-7 (IL-7) signaling pathway is associated with a disease selected from the group consisting of autoimmune diseases, allergic diseases, cancer, diseases related to transplantation, organ or tissue transplant rejection, respiratory diseases, and chronic viral infection.

3. The method of inhibiting inflammation according to claim 1, wherein said antibody is a humanized monoclonal antibody.

4. The method of inhibiting inflammation according to claim 1, wherein the antibody light chain comprises or the antibody light chain variable domain consists of SEQ ID NO: 12.

5. The method of inhibiting inflammation according to claim 1, wherein the human CD127 agent antagonizes interleukin-7 receptor (IL-7R) signaling induced by interleukin-7 (IL7).

6. The method of inhibiting inflammation according to claim 1, wherein said antibody or antigen-binding fragment thereof is an antagonist of interleukin-7 receptor (IL-7R) signaling induced by interleukin-7 (IL-7) and which does not induce the activation of the phosphatidylinositol 3-kinase and/or of the extracellular signal-regulated kinase (ERK) signaling pathway.

7. The method of inhibiting inflammation according to claim 1, wherein said antibody or antigen-binding fragment thereof recognizes an epitope comprising a sequence taken from the 2b site of CD127 and/or disrupts the binding of CD127 to the γc common chain of cytokine receptors.

8. The method of inhibiting inflammation according to claim 1, wherein said antibody or antigen-binding fragment thereof does not induce the internalization of CD127 and/or inhibits IL7-induced internalization of CD127.

9. The method of inhibiting inflammation according to claim 1, wherein said antibody or antigen-binding fragment thereof does not increase the maturation of dendritic cells induced by Thymic Stromal Lymphopoietin (TSLP).

10. The method of inhibiting inflammation according to claim 1, wherein said antibody or antigen-binding fragment thereof has a long-lasting effect on immune response at least 12 months after administration of said antibody or an antigen-binding fragment thereof and/or a fast effect on immune response within a week after administration of said antibody or an antigen-binding fragment thereof.

11. The method of inhibiting inflammation according to claim 1, wherein said antibody or antigen-binding fragment thereof specifically binds to human CD127 with an affinity constant $K_D$ lower than $5\times10^{-9}$ M as determined by biosensor analysis.

12. The method of inhibiting inflammation according to claim 1, wherein said antibody or an antigen-binding fragment thereof specifically binds to human CD127.

13. The method of inhibiting inflammation according to claim 1, wherein the antibody light chain comprises a constant domain and wherein the constant domain is a humanized kappa light chain constant domain.

14. The method of inhibiting inflammation according to claim 13, wherein the light chain constant domain consists of the sequence of SEQ ID NO: 27 or SEQ ID NO: 28.

15. The method of inhibiting inflammation according to claim 3, wherein the antibody heavy chain comprises a heavy chain constant domain and wherein the heavy chain constant domain is a humanized IgG1, IgG2, IgG3, or IgG4 heavy chain constant domain.

16. The method of inhibiting inflammation according to claim 15, wherein the antibody heavy chain constant domain consists of the sequence of SEQ ID NO: 26.

17. The method of inhibiting inflammation according to claim 7, wherein the antibody recognizes an epitope comprising at least the third beta sheet of the site 2b of CD127.

\* \* \* \* \*